US008129344B2

(12) United States Patent
Dzau et al.

(10) Patent No.: US 8,129,344 B2
(45) Date of Patent: *Mar. 6, 2012

(54) METHOD OF REDUCING CELL DEATH BY ADMINISTERING A SFRP POLYPEPTIDE

(75) Inventors: Victor Dzau, Durham, NC (US); Maria Mirotsou, Dresden (DE)

(73) Assignees: Duke University, Durham, NC (US); The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/008,583

(22) Filed: Jan. 11, 2008

(65) Prior Publication Data

US 2008/0176207 A1 Jul. 24, 2008

(51) Int. Cl.
*A61K 38/17* (2006.01)
*C07K 14/435* (2006.01)

(52) U.S. Cl. ............... 514/18.9; 424/185.1; 530/350
(58) Field of Classification Search ............ None
See application file for complete search history.

(56) References Cited

U.S. PATENT DOCUMENTS

| 6,433,155 B1 | 8/2002 | Umansky et al. |
| 2004/0171559 A1 | 9/2004 | Weissman et al. |

FOREIGN PATENT DOCUMENTS

| WO | WO 03/062376 A2 | 7/2003 |
| WO | WO 2004/044142 A2 | 5/2004 |
| WO | WO 2004/087874 A2 | 10/2004 |

OTHER PUBLICATIONS

Mirotsou et al. Secreted frizzled related protein 2 (Sfrp-2) is the key Akt-mesenchymal stem cell-released paracrine factor mediating myocardial survival and repair. Proc Natl Acad Sci USA 104(5): 1643-1649, 2007.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Jacobsen et al. Cell Cultures of Adult Cardiomyocytes as Models of the Myocardium. J Molec Cell Cardiol 18: 661-678, 1986.*
Schluter et al. "Isolation and Culture of Adult Ventricular Cardiomyocytes" in Practical Methods in Cardiovascular Research. Berlin-Heidelberg: Springer-Verlag (2005), pp. 557-567.*
Zhang et al. Secreted frizzled related protein 2 protects cells from apoptosis by blocking the effect of canonical Wnt3a. J Moec Cell CArdiol 46: 370-377, 2009.*
Alvarez-Dolado et al. *Nature*, 425:968-973 (2003).
Barandon et al. *Circulation*, 108:2282-2289 (2003).
Beltrami et al. *Cell*, 114:763-776 (2003).
Bergmann et al. *J. Mol. Cell. Cardiol.*, 37:681-690 (2004).
Caplice et al. *Nat. Clin. Pract. Cardiovasc. Med.*, 1(2):90-95 (2004).
Dimmeler et al. *J. Clin. Invest.*, 115(3):572-583 (2005).
Fazel et al. *J. Clin. Invest.*, 116(7):1865-1877 (2006).
Gnecchi et al. *Nat. Med.*, 11(4):367-368 (2005).
Guo et al. *Circulation*, Abstract only, 114(18):515, Supplement II (Oct. 31, 2006).
Jones et al. *BioEssays*, 24:811-820 (2002).
Kawano et al. *J. Cell Sci.*, 116(13):2627-2634 (2003).
Kinnaird et al. *Circ. Res.*, 95:354-363 (2004).
Lee et al. *J. Biol. Chem.*, 279(15):14602-14609 (2004).
Li et al. *Genome Biol.*, 2(8):0032.1-0032.11 (2001).
Logan et al. *Annu. Rev. Cell Dev. Biol.*, 20 :781-810 (2004).
Mangi et al. *Nat. Med.*, 9(9):1195-1201 (2003).
Manji et al. *J. Clin. Psychiatry*, 61(Suppl. 9):82-96 (2000).
Melo et al. *Circulation*, 109:2386-2393 (2004).
Mercer et al. *EMBO J.*, 19(14):3597-3607 (2000).
Mirotsou et al. *Circulation*, Abstract only, 112(17):660, Supplement (Nov. 17, 2005).
Moon et al. *Science*, 296:1644-1646 (2002).
Nakamura et al. *Proc. Natl. Acad. Sci. USA*, 100(10):5834-5839 (2003).
Pandur et al. *Nature*, 418:636-641 (2002).
Schneider et al. *Genes Dev.*, 15:304-315 (2001).
Schumann et al. *Cardiovasc. Res.*, 45:720-728 (2000).
Uren et al. *J. Biol. Chem.*, 275(6):4374-4382 (2000).
Van Gijn et al. *Cardiovasc. Res.*, 55:16-24 (2002).
Wang et al. *Cancer Res.*, 65(19):8604-8607 (2005).
Xu et al. *Nat. Med.*, 3(9):997-1004 (1997).
GenBank Accession No. BC036503, Oct. 2003.
Han et al., "Secreted Frizzled-related Protein 1 (SFRP1) Protects Fibroblasts from Ceraminde-induced Apoptosis", *J. Biol. Chem.*, 279(4):2832-2840 (2004).
Database EBI, "Protein Factor Discovery Related Isolated Human Polypeptide", Tang et al., XP-002494344, Abstract only, Genbank Accession No. ADS 98181, Dec. 30, 2004.
"SARP-1 may have Cardiovascular Uses." *Appl. Genetics News.* (1999).
Van Gijn et al. "Overexpression of Components of the Frizzled-Dishevelled Cascade Results in Apoptotic Cell Death, Mediated by Beta-Catenin." *Exp. Cell Res.* 265.15(Apr. 2001):46-53.

* cited by examiner

*Primary Examiner* — Bridget E Bunner
(74) *Attorney, Agent, or Firm* — Mintz, Levin, Cohn, Ferris, Glovsky and Popeo, P.C.; Ingrid A. Beattie

(57) ABSTRACT

A purified paracrine factor of a mesenchymal stem cell, such as a Secreted frizzled related protein (Sfrp) is useful to reduce cell death an/or tissue injury associated with ischemic conditions.

4 Claims, 11 Drawing Sheets a The effect of Sfrp2 on caspase activities b The effect of Sfrp2 on rat adult cardiomyocytes c The images of adult rat cardiomyocytes treated with Sfrp2 a Genes up-regulated by Sfrp2 under hypoxia (Superarray)

b The effect of Sfrp2 on mRNA levels of Birc1b (RT-PCR)

c Beta-catenin levels upregulated by Sfrp2

His-h12 protein phosphorylates/activates Akt$^{Thr308}$ in cardiomyocytes at 30 min Phosphorylation of GSK-3β in cardiomyocytes at 30 min Total Akt expression in cardiomyocytes Expression of β-tublin in cardiomyocytes as loading control Inhibiton of cytochrome C release into cytosolic compartment by His-h12 protein during cardiomyocyte apoptosis Stablizition of Mitochondrial Bcl-2 protein level by His-h12 protein during cardiomyocyte apoptosis

METHOD OF REDUCING CELL DEATH BY ADMINISTERING A SFRP POLYPEPTIDE

STATEMENT AS TO FEDERALLY SPONSORED RESEARCH

This invention was made with U.S. government support under National Institutes of Health grant number HL073219. The government has certain rights in the invention.

RELATED APPLICATIONS

This application claims priority to provisional patent application Ser. No. 60/710,028, filed on Aug. 19, 2005 and provisional patent application Ser. No. 60/711,287, filed on Aug. 25, 2005, the entire contents of each being hereby incorporated by reference.

FIELD OF THE INVENTION

The invention relates to cardiac disorders.

BACKGROUND OF THE INVENTION

Patient mortality and morbidity is increased by cell/tissue damage or death resulting from acute and chronic injury or disease of the heart muscle, such as myocardial infarction, cardiac failure, stroke, degenerative neurological disease, spinal injury, musculoskeletal diseases, hypertension, and diabetes.

SUMMARY OF THE INVENTION

The invention is based upon the surprising discovery that paracrine factors secreted from mesenchymal stem cells (MSC) confer a therapeutic benefit to bodily tissues. Thus, stem cells serve as a factory of biologic products that are purified and administered to subjects.

The paracrine factors are useful in cellular and tissue protection, repair, and regeneration. Mesenchymal stem cells or progenitor cells that secrete cytoprotective paracrine factors preferably comprise an Akt gene (Akt-MSC). One or more secreted compounds (e.g., and isolated compound or a mixture of secreted compounds such as a MSC culture supernatant) confers a clinical benefit to a variety of injured, compromised, or disease tissues.

A method of reducing cell death or enhancing tissue repair is carried out by contacting an injured or diseased tissue with a composition comprising a paracrine factor of a mesenchymal stem cell (MSC). The composition is administered to healthy tissue that is determined to be at high risk of injury or to injured tissue following the occurrence of an injury. Preferably, the factor is a Secreted frizzled related protein (Sfrp). Optionally, the composition contains one or more paracrine factors, e.g., two, three, five, ten or more factors. The factors provide cell reparative benefits in a synergistic manner. For example, the composition contains one or more Sfrp, e.g., Sfrp-1, Sfrp-2, and Sfrp-3. In one embodiment, Sfrp-1 comprises an amino acid sequence of SEQ ID NO:5, a mature processed form of SEQ ID NO:5, or a fragment thereof; in another embodiment, Sfrp-2 comprises an amino acid sequence of SEQ ID NO:7, a mature processed form of SEQ ID NO:7, or a fragment thereof; and in yet another embodiment, Sfrp-3 comprises an amino acid sequence of SEQ ID NO:9, a mature processed form of SEQ ID NO:9, or a fragment thereof. The amount of apoptotic cell death is reduced in the presence of a paracrine factor such as an Sfrp compared to in its absence.

Cytoprotective and cell reparative effects are conferred to many types of bodily tissues such as cardiac tissue. For example, in the case of a myocardial infarction, cardiac infarct size is reduced following contact of myocardial tissue with the paracrine factor.

Factors derived from Akt-MSCs, which have been genetically altered to contain a recombinant Akt gene sequence, confer a therapeutic benefit at each stage of a hypoxic cardiac event (early, middle, and late stage). Early on, factors confer a cell protective effect, followed by inotropy, angiogenesis, and cardiac remodeling.

The invention also features methods of inhibiting cell damage, inducing or enhancing cell repair or regeneration or inhibiting an ischemic or reperfusion related injury in a subject. Cell damage or injury is inhibited by administering to the subject or contacting a cell with a composition containing a purified cytoprotective compound such as a substantially pure polypeptide, or a mixture of substantially pure polypeptides such as the Sfrp proteins described above. Other purified proteins, e.g., h1, h5, h8, h12, and h13 are also useful to prevent or reduce cell damage. Accordinglhy, a method of reducing cell death is carried out by contacting an injured or diseased tissue with a composition comprising a purified paracrine factor of a mesenchymal stem cell selected from the group consisting of h1, h5, h8, h12 and h13 or fragment thereof. For example, h12 comprises a fragment of SEQ ID NO:17.

Similarly, cell repair or regeneration is induced by administering to the subject or contacting a cell with a composition containing a purified cytoprotective compound. Polypeptides or other compounds described herein are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylaminde gel electrophoresis, or HPLC analysis. The polypeptide is purified from MSC culture media or recombinantly produced.

Cell or tissue damage is defined by a loss or diminution of cell function. Such loss or decrease in function leads to eventual cell death. The cell is a cardiac cell such as a cardiomyocyte, a kidney cell, a liver cell, a neurological (e.g., brain, spinal cord) cell, or a pancreatic cell. For example, a loss of cardiomyocyte function results in the loss of the contractile function of the cell. Cardiomyocytes that have lost their ability to contract form round cells rather that rod shaped cells when cultured. Ischemia causes irreversible cellular/tissue damage and cell death. Reperfusion exacerbates ischemic damage by activating inflammatory response and oxidative stress. Oxidative stress modifies membrane lipids, proteins and nucleic acids resulting in cellular/tissue damage or death, and depression of cardiac, endothelial and kidney function.

Also included in the invention are methods of regenerating an injured myocardial tissue by administered to the tissue a composition containing a cytoprotective compound. The cardiac muscle has been damaged by disease, such as a myocardial infarction. By regenerating an injured myocardial tissue is meant restoring ventricular function and/or decreasing infarct size. Ventricular function is measured by methods known in the art such as radionuclide angiography.

A cytoprotective compound is a compound, which is capable of inhibiting cell damage such as oxidative-stress induced cell death or apoptosis. In addition to Sfrps, cytoprotective compounds include for example adipsin, adrenomedullin, chemokine (C—C motif) ligand 2, cysteine rich protein 61, lysyl oxidase-like 2, or serine proteinase inhibitor.

The composition is administered to the subject prior to, at the time of, or shortly after (1, 5, 10, 15, 30, 60 minutes; 1.5, 2, 4, 6, 12, 18, 24, 48 hours) identification of cell damage or identification of a symptom of ischemia or reperfusion injury. For example the composition is administered to a subject prior to a cardiac event or ischemic-reperfusion injury. Such a subject is a risk candidate for an ischemic event or condition. Symptoms of a cardiac event include for example, chest pain, arm pain, fatigue and shortness of breath. For example, the composition is administered at the onset of symptoms, e.g., chest pain, associated with a cardiac event such as a myocardial infarction. The composition is administered systemically or locally. For example, the composition is administered directly, i.e., by myocardial injection to the cardiac tissue, or systemically, e.g., interperitoneally, orally, intravenously. In another example, administration of the composition is carried out by infusion into a coronary artery. Slow-release formulations, e.g., a dermal patch, in which diffusion of the composition from an excipient such as a polymeric carrier mediates drug delivery are also within the invention. Optionally, the subject is further administered VEGF or thyrosin beta 4.

The composition is administered at a dose sufficient to inhibit apoptotic death or oxidative stress-induced cell death. To determine whether the composition inhibits oxidative-stress induced cell death, the composition is tested by incubating the composition with a primary or immortalized cell such as a cardiomyocyte. A state of oxidative stress of the cells is induced (e.g., by incubating cells with $H_2O_2$), and cell viability is measured using standard methods. As a control, the cells are incubated in the absence of the composition and then a state of oxidative stress is induced. A decrease in cell death (or an increase in the number of viable cells) in the compound treated sample indicates that the composition inhibits oxidative-stress induced cell death. Alternatively, an increase in cell death (or an decrease in the number of viable cells) in the compound treated sample indicates that the composition does not inhibit oxidative-stress induced cell death. The test is repeated using different doses of the composition to determine the dose range in which the composition functions to inhibit oxidative-stress induced cell death.

A subject to be treated is suffering from or at risk of developing a condition characterized by aberrant cell damage such as oxidative-stress induced cell death (e.g., apoptotic cell death) or an ischemic or reperfusion related injury. A subject suffering from or at risk of developing such a condition is identified by the detection of a known risk factor, e.g., gender, age, high blood pressure, obesity, diabetes, prior history of smoking, stress, genetic or familial predisposition, attributed to the particular disorder, or previous cardiac event such as myocardial infarction or stroke.

Conditions characterized by aberrant cell damage or death include cardiac disorders (acute or chronic) such as stroke, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, renal failure, kidney ischemia, ischemic hepatitis, hepatic vein thrombosis, cirrhosis, portal vein thrombosis, pancreatitis, ischemic colitis, or myocardial hypertrophy. Cardiac repair or regeneration is evaluated by detecting an improvement of symptoms such as chest pain or shortness of breath as well as by evaluation of heart function by standard methods such as cardiac magnetic resonance, echocardiography, and/or ventricular angiography.

Also within the invention is a cell culture or preservation media containing purified Sfrp2 and a method of maintaining inhibiting stem cell differentiation, e.g., inhibiting myogenesis, by contacting a population of isolated stem cells with purified Sfrp2. Isolated stem cells are selected from the group consisting of embryonic stem cells, mesenchymal stem cells, and hematopoetic stem cells. Stem cells are isolated from the tissue of origin by fractionation by cell surface markers or other distinguishing characteristics. Preferably, a population of isolated cells is at least 85% stem cells. More preferably, the population is 90, 95, 98, 99, 100% stem cells.

This factor is involved in the maintenance and self renewal of tissue specific and embryonic stem cells. For example, differentiation of stem cells, e.g., embryonic stem cells, is inhibited by Sfrp2. Myogenesis is inhibited by contacting stem cells with Sfrp2. In another example, bone marrow-derived hematopoetic stem are maintained in a stem cell state by contacting the cells with purified Sfrp2. Preservation of stem cells in this manner is useful in transport and storage of stem cells prior to transplantation into a subject for therapeutic purposes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A shows levels of Sfrp1, Sfrp2 and Sfrp3 expression as estimated by microarray analysis and shows a nearly 10 fold upregulation of Sfrp2 in Akt-MSC compared to GFP-MSC. FIG. 1B shows a quantitative real-time RT-PCR validation of mRNA expression levels that demonstrates a 100 fold upregulation of Sfrp2 gene expression in Akt-MSC compared to GFP-MSC.

FIG. 5A is a photograph of an electrophoretic gel showing that Wnt3a mRNA expression as detected by RT-PCR is increased in hypoxic cardiomyocytes while expression of Wnt5 remains unchanged. The data indicate that hypoxic cardiomyocytes upregulate Wnt3a expression and that Sfrp2 blocks pro-apototic effects of Wnt3a.

FIG. 5B is a bar graph showing that Wnt3a (3 nM) increases caspase activity of cardiomyocytes undergoing hypoxia/reoxygenation injury; Sfrp2 at a similar concentration significantly attenuates Wnt3a induced caspase activity (*vs. normoxia, $p<0.05$; **vs. wnt+hypoxia/reoxygenation, $p<0.05$, n=6/group).

DETAILED DESCRIPTION

Figure 1:
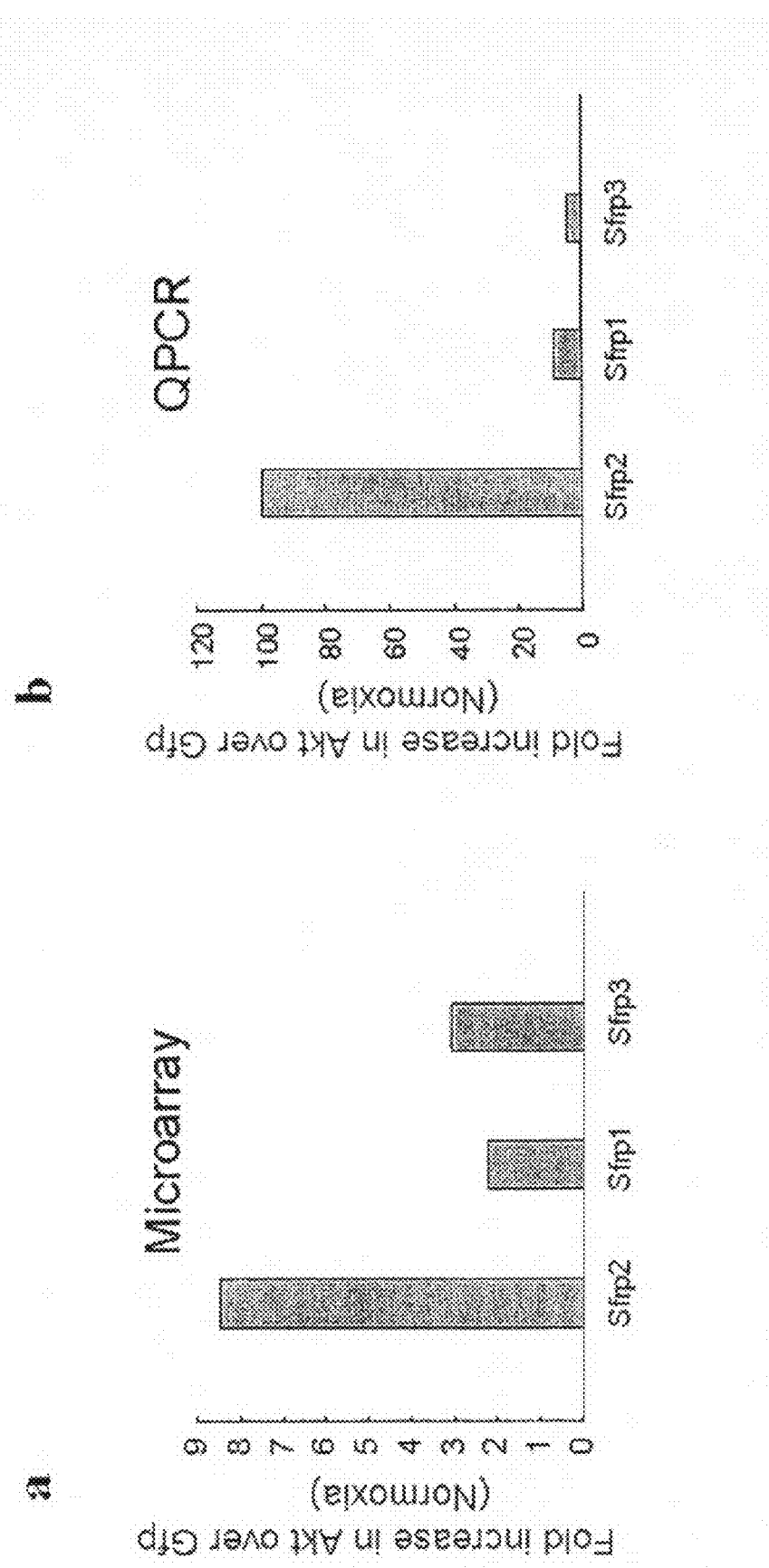
FIGS. 1A and 1B are bar graphs showing that Sfrps are expressed in mesenchymal stem cells.

The present invention is based upon the unexpected discovery of that MSC-secreted products confer a therapeutic benefit to injured or compromised tissues. Disclosed herein is a Akt-MSC mediated paracrine mechanism of organ protection and repair. More particularly, the invention provides purified polypeptides such as Srfps isolated from Akt-MSCs or recombinantly or synthetically produced and methods of using these polypeptides to prevent or reduce myocardial damage and ventricular dysfunction.

Akt Genes

Akt-MSCs are produced by introducing (e.g., by retrovirus-mediated transduction) into mesenchymal stem cells isolated from the bone marrow an Akt coding sequence or fragment, e.g., Akt-1, Ak-2 or Akt-3. The Akt nucleic acid is human, mouse, or rat.

Exemplary human Akt-1 polypeptides include GenBank Accession numbers NP_005154 and AAH00479. Exemplary human Akt-2 polypeptides includes for example GenBank Accession numbers P31751 and NP_001617. Exemplary human Akt-3 polypeptides includes for example GenBank Accession numbers Q9Y243 and NP_005456. Exemplary nucleic acids encoding Akt include human Akt-1 available at GENBANK™ Accession No. NM_005163 (SEQ ID NO:1), human Akt-2 available at GENBANK™ Accession No. NM_001626 (SEQ ID NO:2) and human Akt-3 available at GENBANK™ Accession No. AJ245709 (SEQ ID NO:3) (all of which are hereby incorporated by reference)or nucleic acids encoding the human Akt polypeptides described above. mRNA sequences and the corresponding coding region for human Akt are shown below.

```
Akt-1 mRNA
                                                        (SEQ ID NO: 1)
   1 atcctgggac agggcacagg gccatctgtc accaggggct tagggaaggc cgagccagcc 61 tgggtcaaag aagtcaaagg ggctgcctgg aggaggcagc ctgtcagctg gtgcatcaga 121 ggctgtggcc aggccagctg ggctcgggga gcgccagcct gagaggagcg cgtgagcgtc 181 gcgggagcct cgggcaccat gagcgacgtg gctattgtga aggagggttg gctgcacaaa 241 cgagggagt acatcaagac ctggcggcca cgctacttcc tcctcaagaa tgatggcacc 301 ttcattggct acaaggagcg gccgcaggat gtggaccaac gtgaggctcc cctcaacaac 361 ttctctgtgg cgcagtgcca gctgatgaag acggagcggc cccggcccaa caccttcatc 421 atccgctgcc tgcagtggac cactgtcatc gaacgcacct tccatgtgga gactcctgag 481 gagcgggagg agtggacaac cgccatccag actgtggctg acggcctcaa gaagcaggag
```

-continued

```
 541 gaggaggaga tggacttccg gtcgggctca cccagtgaca actcaggggc tgaagagatg
 601 gaggtgtccc tggccaagcc caagcaccgc gtgaccatga acgagtttga gtacctgaag
 661 ctgctgggca agggcacttt cggcaaggtg atcctggtga aggagaaggc cacaggccgc
 721 tactacgcca tgaagatcct caagaaggaa gtcatcgtgg ccaaggacga ggtggcccac
 781 acactcaccg agaaccgcgt cctgcagaac tccaggcacc ccttcctcac agccctgaag
 841 tactcttttcc agacccacga ccgcctctgc tttgtcatgg agtacgccaa cggggggcgag
 901 ctgttcttcc acctgtcccg ggaacgtgtg ttctccgagg accgggcccg cttctatggc
 961 gctgagattg tgtcagccct ggactacctg cactcggaga gaacgtggt gtaccgggac
1021 ctcaagctgg agaacctcat gctggacaag gacgggcaca ttaagatcac agacttcggg
1081 ctgtgcaagg aggggatcaa ggacggtgcc accatgaaga ccttttgcgg cacacctgag
1141 tacctggccc ccgaggtgct ggaggacaat gactacggcc gtgcagtgga ctggtggggg
1201 ctgggcgtgg tcatgtacga gatgatgtgc ggtcgcctgc ccttctacaa ccaggaccat
1261 gagaagcttt ttgagctcat cctcatggag gagatccgct cccgcgcac gcttggtccc
1321 gaggccaagt ccttgctttc agggctgctc aagaaggacc ccaagcagag gcttggcggg
1381 ggctccgagg acgccaagga gatcatgcag catcgcttct tgccggtat cgtgtggcag
1441 cacgtgtacg agaagaagct cagcccaccc ttcaagcccc aggtcacgtc ggagactgac
1501 accaggtatt ttgatgagga gttcacggcc cagatgatca ccatcacacc acctgaccaa
1561 gatgacagca tggagtgtgt ggacagcgag cgcaggcccc acttcccca gttctcctac
1621 tcggccagca gcacggcctg aggcggcggt ggactgcgct ggacgatagc ttggagggat
1681 ggagaggcgg cctcgtgcca tgatctgtat ttaatggttt ttatttctcg ggtgcatttg
1741 agagaagcca cgctgtcctc tcgagcccag atggaaagac gttttttgtgc tgtgggcagc
1801 accctccccc gcagcggggt agggaagaaa actatcctgc gggttttaat ttatttcatc
1861 cagtttgttc tccgggtgtg gcctcagccc tcagaacaat ccgattcacg tagggaaatg
1921 ttaaggactt ctacagctat gcgcaatgtg gcattggggg gccgggcagg tcctgcccat
1981 gtgtcccctc actctgtcag ccagccgccc tgggctgtct gtcaccagct atctgtcatc
2041 tctctggggc cctgggcctc agttcaacct ggtggcacca gatgcaacct cactatggta
2101 tgctggccag caccctctcc tggggggtggc aggcacacag cagcccccca gcactaaggc
2161 cgtgtctctg aggacgtcat cggaggctgg gcccctggga tgggaccagg gatgggggat
2221 gggccagggt ttacccagtg ggacagagga gcaaggttta aatttgttat tgtgtattat
2281 gttgttcaaa tgcattttgg gggtttttaa tctttgtgac aggaaagccc tccccttcc
2341 ccttctgtgt cacagttctt ggtgactgtc ccaccggagc ctcccctca gatgatctct
2401 ccacggtagc acttgacctt ttcgacgctt aacctttccg ctgtcgcccc aggccctccc
2461 tgactccctg tggggggtggc catccctggg ccctccacg cctcctggcc agacgctgcc
2521 gctgccgctg caccacggcg ttttttttaca acattcaact ttagtatttt tactattata
2581 atataatatg gaaccttccc tccaaattct
```

Coding sequence = nucleotide 199-1641.

Akt-2 mRNA (SEQ ID NO: 2)

```
   1 gaattccagc ggcggcgccg ttgccgctgc cgggaaacac aaggaaaggg aaccagcgca
  61 gcgtggcgat gggcggggggt agagccccgc cggagaggct gggcggctgc cggtgacaga
 121 ctgtgccctc tccacggtgc ctcctgcatg tcctgctgcc ctgagctgtc ccagctaggg
 181 tgacagcgta ccacgctgcc accatgaatg aggtgtctgt catcaaagaa ggctggctcc
```

-continued

```
 241 acaagcgtgg tgaatacatc aagacctgga ggccacggta cttcctgctg aagagcgacg
 301 gctccttcat tgggtacaag gagagggccccg aggcccctga tcagactcta ccccccttaa
 361 acaacttctc cgtagcagaa tgccagctga tgaagaccga gaggccgcga cccaacacct
 421 ttgtcatacg ctgcctgcag tggaccacag tcatcgagag gaccttccac gtggattctc
 481 cagacgagag ggaggagtgg atgcgggcca tccagatggt cgccaacagc ctcaagcagc
 541 gggccccagg cgaggacccc atggactaca gtgtggctc ccccagtgac tcctccacga
 601 ctgaggagat ggaagtggcg gtcagcaagg cacgggctaa agtgaccatg aatgacttcg
 661 actatctcaa actccttggc aagggaacct ttggcaaagt catcctggtg cgggagaagg
 721 ccactggccg ctactacgcc atgaagatcc tgcgaaagga agtcatcatt gccaaggatg
 781 aagtcgctca cacagtcacc gagagccggg tcctccagaa caccaggcac ccgttcctca
 841 ctgcgctgaa gtatgccttc cagacccacg accgcctgtg ctttgtgatg gagtatgcca
 901 acggggggtga gctgttcttc cacctgtccc gggagcgtgt cttcacagag gagcgggccc
 961 ggttttatgg tgcagagatt gtctcggctc ttgagtactt gcactcgcgg gacgtggtat
1021 accgcgacat caagctggaa aacctcatgc tggacaaaga tggccacatc aagatcactg
1081 actttggcct ctgcaaagag ggcatcagtg acggggccac catgaaaacc ttctgtggga
1141 ccccggagta cctggcgcct gaggtgctgg aggacaatga ctatggccgg ccgtggact
1201 ggtgggggct gggtgtggtc atgtacgaga tgatgtgcgg ccgcctgccc ttctacaacc
1261 aggaccacga gcgcctcttc gagctcatcc tcatggaaga gatccgcttc ccgcgcacgc
1321 tcagccccga ggccaagtcc ctgcttgctg ggctgcttaa gaaggacccc aagcagaggc
1381 ttggtggggg gcccagcgat gccaaggagg tcatggagca ggttcttc ctcagcatca
1441 actggcagga cgtggtccag aagaagctcc tgccaccctt caaacctcag gtcacgtccg
1501 aggtcgacac aagtacttc gatgatgaat ttaccgccca gtccatcaca atcacacccc
1561 ctgaccgcta tgacagcctg ggcttactgg agctggacca gcggacccac ttcccccagt
1621 tctcctactc ggccagcatc cgcgagtgag cagtctgccc acgcagagga cgcacgctcg
1681 ctgccatcac cgctgggtgg ttttttaccc ctgcc
Coding sequence = nucleotide 204-1649.
Akt-3 mRNA
                                                               (SEQ ID NO: 3)
   1 gggagtcatc atgagcgatg ttaccattgt gaaagaaggt tgggttcaga agaggggaga
  61 atatataaaa aactggaggc caagatactt ccttttgaag acagatggct cattcatagg
 121 atataaagag aaacctcaag atgtggattt accttatccc ctcaacaact tttcagtggc
 181 aaaatgccag ttaatgaaaa cagaacgacc aaagccaaac acatttataa tcagatgtct
 241 ccagtggact actgttatag agaacatt tcatgtagat actccagagg aaagggaaga
 301 atggacagaa gctatccagg ctgtagcaga cagactgcag aggcaagaag aggagagaat
 361 gaattgtagt ccaacttcac aaattgataa tataggagag aagagatgg atgcctctac
 421 aacccatcat aaaagaaaga caatgaatga ttttgactat ttgaaactac taggtaaagg
 481 cacttttggg aaagttattt tggttcgaga aaggcaagt ggaaatact atgctatgaa
 541 gattctgaag aaagaagtca ttattgcaaa ggatgaagtg gcacacactc taactgaaag
 601 cagagtatta agaacactag acatcccctt tttaacatcc ttgaaatatt ccttccagac
 661 aaaagaccgt tgtgttttg tgatggaata tgttaatggg ggcgagctgt ttttccattt
 721 gtcgagagag cgggtgttct ctgaggaccg cacacgtttc tatggtgcag aaattgtctc
```

```
 781 tgccttggac tatctacatt ccggaaagat tgtgtaccgt gatctcaagt tggagaatct 841 aatgctggac aaagatggcc acataaaaat tacagatttt ggactttgca aagaagggat 901 cacagatgca gccaccatga agacattctg tggcactcca gaatatctgg caccagaggt 961 gttagaagat aatgactatg gccgagcagt agactggtgg ggcctagggg ttgtcatgta 1021 tgaaatgatg tgtgggaggt tacctttcta caaccaggac catgagaaac tttttgaatt 1081 aatattaatg gaagacatta aatttcctcg aacactctct tcagatgcaa aatcattgct 1141 ttcagggctc ttgataaagg atccaaataa acgccttggt ggaggaccag atgatgcaaa 1201 agaaattatg agacacagtt tcttctctgg agtaaactgg caagatgtat atgataaaaa 1261 gcttgtacct ccttttaaac ctcaagtaac atctgagaca gatactagat attttgatga 1321 agaatttaca gctcagacta ttacaataac accacctgaa aaatatgatg aggatggtat 1381 ggactgcatg gacaatgaga ggcggccgca tttccctcaa ttttcctact ctgcaagtgg 1441 acgagaataa gtctctttca ttctgctact tcactgtcat cttcaattta ttactgaaaa 1501 tgattcctgg acatcaccag tcctagctct tacacatagc aggggca
Coding sequence = nucleotide 11-1450
```

Intramyocardial transplantation of adult stem cells has been proposed as a therapy to repair and regenerate damaged myocardium and to restore cardiac function after acute myocardial infarction (MI). Given their multipotency, low immunogenicity, amenability to ex vivo expansion and genetic modification, autologous bone marrow derived MSCs are suitable for this purpose. Injection of MSCs reduces post-infarction ventricular remodeling and in some cases improves left ventricular function. However prior to the invention, mechanism(s) underlying these therapeutic effects have not been clearly defined. In situ differentiation of the transplanted MSCs into cardiomyocytes and other constituent cardiac cell types has been suggested. Intramyocardial transplantation of MSCs transduced with a retroviral vector overexpressing the survival gene Akt markedly improves the therapeutic efficacy of MSCs in preventing ventricular remodeling and restoring cardiac function.

The data described herein shows that therapeutic effects seen with the administration of cells occur in less than 72 hours after infarction. These early dramatic effects cannot be readily attributed to myocardial regeneration or neoangiogenesis, but rather indicate that Akt-MSCs release biologically active factors that exert paracrine actions on the ischemic cardiomyocytes. Under hypoxic stimulation, genetically-modified bone marrow derived MSCs overexpressing the Akt gene release paracrine factors that exert cytoprotective effects on isolated cardiomyocytes. Intramyocardial injection of these substances reduces infarct size, prevents left ventricular dysfunction, and decreases in the number of apoptotic cardiomyocytes in vivo. In addition, no increase in microvessel density was observed in is the treated groups compared to controls 72 hours after the injection of the conditioned medium Thus, a significant portion of the salutary effects of Akt-MSCs transplantation is attributable to protection and functional recovery of ischemic myocardium, instead of, or in addition to, de novo cardiac repair and regeneration. The ability of bone marrow derived MSCs, especially Akt-MSCs, to produce factor(s) capable of protecting cardiomyocytes from cell death has not been previously demonstrated.

Secreted Frizzled-Related Proteins

The GENBANK™ Accession numbers of human Sfrps include BCO36503 (Sfrp1), BC008666 (Sfrp2), and NM001463 (Sfrp3), hereby incorporated by reference. The amino acid sequence of exemplary Sfrp polypeptides and nucleotides encoding the polypeptides (coding sequences) are described below. The Sfrp polypeptides, mature processed forms, and/or fragments thereof are used in the cardioprotective and repair methods described herein.

```
Human SFRP1 mRNA sequence
                                                          (SEQ ID NO: 4)
   1 cctgcagcct ccggagtcag tgccgcgcgc ccgccgcccc gcgccttcct gctcgccgca 61 cctccgggag ccggggcgca cccagcccgc agcgccgcct ccccgcccgc gccgcctccg 121 accgcaggcc gagggccgcc actgccgggg gggaccgggc agcagcttgc ggccgcggag 181 ccgggcaacg ctggggactg cgccttttgt ccccggaggt ccctggaagt ttgcggcagg 241 acgcgcgcgg ggaggcggcg gaggcagccc cgacgtcgcg gagaacaggg cgcagagccg 301 gcatgggcat cgggcgcagc gagggggggcc gccgcgggc agccctgggc gtgctgctgg 361 cgctgggcgc ggcgcttctg gccgtgggct cggccagcga gtacgactac gtgagcttcc 421 agtcggacat cggcccgtac cagagcgggc gcttctacac caagccacct cagtgcgtgg 481 acatccccgc ggacctgcgg ctgtgccaca acgtgggcta caagaagatg gtgctgccca
```

-continued

```
 541 acctgctgga gcacgagacc atggcggagg tgaagcagca ggccagcagc tgggtgcccc
 601 tgctcaacaa gaactgccac gccggcaccc aggtcttcct ctgctcgctc ttcgcgcccg
 661 tctgcctgga ccggcccatc tacccgtgtc gctggctctg cgaggccgtg cgcgactcgt
 721 gcgagccggt catgcagttc ttcggcttct actggcccga gatgcttaag tgtgacaagt
 781 tccccgaggg ggacgtctgc atcgccatga cgccgcccaa tgccaccgaa gcctccaagc
 841 cccaaggcac aacggtgtgt cctccctgtg caacgagtt gaaatctgag gccatcattg
 901 aacatctctg tgccagcgag tttgcactga ggatgaaaat aaaagaagtg aaaaagaaa
 961 atggcgacaa gaagattgtc cccaagaaga agaagcccct gaagttgggg cccatcaaga
1021 agaaggacct gaagaagctt gtgctgtacc tgaagaatgg ggctgactgt ccctgccacc
1081 agctggacaa cctcagccac cacttcctca tcatgggccg caaggtgaag agccagtact
1141 tgctgacggc catccacaag tgggacaaga aaacaaggga gttcaaaaac ttcatgaaga
1201 aaatgaaaaa ccatgagtgc cccacctttc agtccgtgtt taagtgattc tcccgggggc
1261 agggtgggga gggagcctcg ggtggggtgg gagcggggg gacagtgccc cgggaacccg
1321 gtgggtcaca cacgcact gcgcctgtca gtagtggaca ttgtaatcca gtcggcttgt
1381 tcttgcagca ttcccgctcc cttccctcca tagccacgct ccaaaccccca gggtagccat
1441 ggccgggtaa agcaagggcc atttagatta ggaaggtttt taagatccgc aatgtggagc
1501 agcagccact gcacaggagg aggtgacaaa ccatttccaa cagcaacaca gccactaaaa
1561 cacaaaaagg gggattgggc ggaaagtgag agccagcagc aaaaactaca ttttgcaact
1621 tgttggtgtg gatctattgg ctgatctatg cctttcaact agaaaattct aatgattggc
1681 aagtcacgtt gttttcaggt ccagagtagt ttcttttctgt ctgctttaaa tggaaacaga
1741 ctcataccac acttacaatt aaggtcaagc ccagaaagtg ataagtgcag ggaggaaaag
1801 tgcaagtcca ttatgtaata gtgacagcaa agggaccagg ggagaggcat tgccttctct
1861 gcccacagtc tttccgtgtg attgtctttg aatctgaatc agccagtctc agatgcccca
1921 aagtttcggt tcctatgagc ccggggcatg atctgatccc caagacatgt ggaggggcag
1981 cctgtgcctc cctttgtgtc agaaaaagga aaccacagtg agcctgagag agacggcgat
2041 tttcgggctg agaaggcagt agttttcaaa acacatagtt aaaaaagaaa caaatgaaaa
2101 aaattttaga acagtccagc aaattgctag tcagggtgaa ttgtgaaatt gggtgaagag
2161 cttaggattc taatctcatg ttttttcctt ttcacatttt taaaagaaca atgacaaaca
2221 cccacttatt tttcaaggtt ttaaaacagt ctacattgag catttgaaag gtgtgctaga
2281 acaaggtctc ctgatccgtc cgaggctgct tcccagagga gcagctctcc ccaggcattt
2341 gccaagggag gcggatttcc ctggtagtgt agctgtgtgg ctttccttcc tgaagagtcc
2401 gtggttgccc tagaacctaa caccccctag caaaactcac agagctttcc gttttttttct
2461 ttcctgtaaa gaaacatttc ctttgaactt gattgcctat ggatcaaaga aattcagaac
2521 agcctgcctg tcccccgca cttttttacat atatttgttt catttctgca gatggaaagt
2581 tgacatgggt ggggtgtccc catccagcga gagagtttca aaagcaaaac atctctgcag
2641 ttttttcccaa gtaccctgag atacttccca aagcccttat gtttaatcag cgatgtatat
2701 aagccagttc acttagacaa ctttaccctt cttgtccaat gtacaggaag tagttctaaa
2761 aaaaatgcat attaatttct tccccccaaag ccggattctt aattctctgc aacactttga
2821 ggacattttat gattgtccct ctgggccaat gcttataccc agtgaggatg ctgcagtgag
2881 gctgtaaagt ggcccctgc ggccctagcc tgacccggag gaaaggatgg tagattctgt
```

-continued

```
2941 taactcttga agactccagt atgaaaatca gcatgcccgc ctagttacct accggagagt 3001 tatcctgata aattaacctc tcacagttag tgatcctgtc cttttaacac cttttttgtg 3061 gggttctctc tgacctttca tcgtaaagtg ctggggacct taagtgattt gcctgtaatt 3121 ttggatgatt aaaaaatgtg tatatatatt agctaattag aaatattcta cttctctgtt 3181 gtcaaactga aattcagagc aagttcctga gtgcgtggat ctgggtctta gttctggttg 3241 attcactcaa gagttcagtg ctcatacgta tctgctcatt ttgacaaagt gcctcatgca 3301 accgggccct ctctctgcgg cagagtcctt agtggagggg tttacctgga acattagtag 3361 ttaccacaga atacggaaga gcaggtgact gtgctgtgca gctctctaaa tgggaattct 3421 caggtaggaa gcaacagctt cagaaagagc tcaaaataaa ttggaaatgt gaatcgcagc 3481 tgtgggtttt accaccgtct gtctcagagt cccaggacct tgagtgtcat tagttacttt 3541 attgaaggtt ttagacccat agcagctttg tctctgtcac atcagcaatt tcagaaccaa 3601 aagggaggct ctctgtaggc acagagctgc actatcacga gcctttgttt ttctccacaa 3661 agtatctaac aaaaccaatg tgcagactga ttggcctggt cattggtctc cgagagagga 3721 ggtttgcctg tgatttccta attatcgcta gggccaaggt gggatttgta aagctttaca 3781 ataatcattc tggatagagt cctgggaggt ccttggcaga actcagttaa atctttgaag 3841 aatatttgta gttatcttag aagatagcat gggaggtgag gattccaaaa acattttatt 3901 tttaaaatat cctgtgtaac acttggctct tggtacctgt gggttagcat caagttctcc 3961 ccagggtaga attcaatcag agctccagtt tgcatttgga tgtgtaaatt acagtaatcc 4021 catttcccaa acctaaaatc tgttttttctc atcagactct gagtaactgg ttgctgtgtc 4081 ataacttcat agatgcagga ggctcaggtg atctgtttga ggagagcacc ctaggcagcc 4141 tgcagggaat aacatactgg ccgttctgac ctgttgccag cagatacaca ggacatggat 4201 gaaattcccg tttcctctag tttcttcctg tagtactcct cttttagatc ctaagtctct 4261 tacaaaagct tgaatactg tgaaaatgtt ttacattcca tttcatttgt gttgtttttt 4321 taactgcatt ttaccagatg ttttgatgtt atcgcttatg ttaatagtaa ttcccgtacg 4381 tgttcatttt attttcatgc ttttcagcc atgtatcaat attcacttga ctaaaatcac 4441 tcaattaatc aatgaaaaaa aaaaa
```

Human SFRP1 protein sequence
(SEQ ID NO: 5)

MGIGRSEGGRRGAALGVLLALGAALLAVGSASEYDYVSFQSDIGPYQSGRFYTKPPQCVDIPADLRLCH

NVGYKKMVLPNLLEHETMAEVKQQASSWVPLLNKNCHAGTQVFLCSLFAPVCLDRPIYPCRWLCEAVRD

SCEPVMQFFGFYWPEMLKCDKFPEGDVCIAMTPPNATEASKPQGTTVCPPCDNELKSEAIIEHLCASEF

ALRMKIKEVKKENGDKKIVPKKKKPLKLGPIKKKDLKKLVLYLKNGADCPCHQLDNLSHHFLIMGRKVK

SQYLLTAIHKWDKKNKEFKNFMKKMKNHECPTFQSVFK

Human SFRP2 mRNA sequence
(SEQ ID NO: 6)

```
  1 caacggctca ttctgctccc ccgggtcgga gccccccgga gctgcgcgcg ggcttgcagc 61 gcctcgcccg cgctgtcctc ccggtgtccc gcttctccgc gccccagccg ccggctgcca 121 gcttttcggg gccccgagtc gcacccagcg aagagagcgg gcccgggaca agctcgaact 181 ccggccgcct cgcccttccc cggctccgct ccctctgccc cctcggggtc gcgcgcccac 241 gatgctgcag ggccctggct cgctgctgct gtcttcctc gcctcgcact gctgctgggg 301 ctcggcgcgc gggctcttcc tctttggcca gcccgacttc tcctacaagc gcagcaattg 361 caagcccatc cctgccaacc tgcagctgtg ccacggcatc gaataccaga acatgcggct 421 gcccaacctg ctgggccacg agaccatgaa ggaggtgctg gagcaggccg cgcttggat
```

-continued

```
 481 cccgctggtc atgaagcagt gccacccgga caccaagaag ttcctgtgct cgctcttcgc
 541 ccccgtctgc ctcgatgacc tagacgagac catccagcca tgccactcgc tctgcgtgca
 601 ggtgaaggac cgctgcgccc cggtcatgtc cgccttcggc ttcccctggc ccgacatgct
 661 tgagtgcgac cgtttccccc aggacaacga ccttttgcatc cccctcgcta gcagcgacca
 721 cctcctgcca gccaccgagg aagctccaaa ggtatgtgaa gcctgcaaaa ataaaaatga
 781 tgatgacaac gacataatgg aaacgctttg taaaaatgat tttgcactga aaataaaagt
 841 gaaggagata acctacatca accgagatac caaaatcatc ctggagacca gagcaagac
 901 catttacaag ctgaacggtg tgtccgaaag ggacctgaag aaatcggtgc tgtggctcaa
 961 agacagcttg cagtgcacct gtgaggagat gaacgacatc aacgcgccct atctggtcat
1021 gggacagaaa caggtggggg agctggtgat cacctcggtg aagcggtggc agaagggggca
1081 gagagagttc aagcgcatct cccgcagcat ccgcaagctg cagtgctagt cccggcatcc
1141 tgatggctcc gacaggcctg ctccagagca cggctgacca tttctgctcc gggatctcag
1201 ctcccgttcc ccaagcacac tcctagctgc tccagtctca gcctgggcag cttcccctg
1261 ccttttgcac gtttgcatcc ccagcatttc ctgagttata aggccacagg agtggatagc
1321 tgttttcacc taaaggaaaa gcccacccga atcttgtaga aatattcaaa ctaataaaat
1381 catgaatatt tttatgaagt ttaaaaatag ctcactttaa agctagtttt gaataggtgc
1441 aactgtgact tgggtctggt tggttgttgt ttgttgtttt gagtcagctg attttcactt
1501 cccactgagg ttgtcataac atgcaaattg cttcaatttt ctctgtggcc caaacttgtg
1561 ggtcacaaac cctgttgaga taaagctggc tgttatctca acatcttcat cagctccaga
1621 ctgagactca gtgtctaagt cttacaacaa ttcatcattt tataccttca atgggaactt
1681 aaactgttac atgtatcaca ttccagctac aatacttcca tttattagaa gcacattaac
1741 catttctata gcatgatttc ttcaagtaaa aggcaaaaga tataaatttt ataattgact
1801 tgagtacttt aagccttgtt taaaacattt cttacttaac ttttgcaaat taaacccatt
1861 gtagcttacc tgtaatatac atagtagttt acctttaaaa gttgtaaaaa tattgcttta
1921 accaacactg taaatatttc agataaacat tatattcttg tatataaact ttacatcctg
1981 ttttacctat aaaaaaaaaa aaaaa
```

Human SFRP2 protein sequence
(SEQ ID NO: 7)

MLQGPGSLLLLFLASHCCLGSARGLFLFGQPDFSYKRSNCKPIPANLQLCHGIEYQNMRLPNLLGHETM
KEVLEQAGAWIPLVMKQCHPDTKKFLCSLFAPVCLDDLDETIQPCHSLCVQVKDRCAPVMSAFGFPWPD
MLECDRFPQDNDLCIPLASSDHLLPATEEAPKVCEACKNKNDDDNDIMETLCKNDFALKIKVKEITYINR
DTKIILETKSKTIYKLNGVSERDLKKSVLWLKDSLQCTCEEMNDINAPYLVMGQKQGGELVITSVKRWQ
KGQREFKRISRSIRKLQC

Human SFRP3 mRNA sequence
(SEQ ID NO: 8)

```
  1 gttgggaaag agcagcctgg gcggcagggg cggtggctgg agctcggtaa agctcgtggg
 61 accccattgg gggaatttga tccaaggaag cggtgattgc cggggaggga gaagctccca
121 gatccttgtg tccacttgca gcggggggagg cggagacggc ggagcgggcc ttttggcgtc
181 cactgcgcgg ctgcaccctg ccccatcctg ccgggatcat ggtctgcggc agcccgggag
241 ggatgctgct gctgcggggcc gggctgcttg ccctggctgc tctctgcctg ctccgggtgc
301 ccggggctcg gctgcagcc tgtgagcccg tccgcatccc cctgtgcaag tccctgccct
361 ggaacatgac taagatgccc aaccacctgc accacagcac tcaggccaac gccatcctgg
```

```
-continued
 421 ccatcgagca gttcgaaggt ctgctgggca cccactgcag ccccgatctg ctcttcttcc 481 tctgtgccat gtacgcgccc atctgcacca ttgacttcca gcacgagccc atcaagccct 541 gtaagtctgt gtgcgagcgg gcccggcagg gctgtgagcc catactcatc aagtaccgcc 601 actcgtggcc ggagaacctg gcctgcgagg agctgccagt gtacgacagg ggcgtgtgca 661 tctctcccga ggccatcgtt actgcggacg gagctgattt tcctatggat tctagtaacg 721 gaaactgtag aggggcaagc agtgaacgct gtaaatgtaa gcctattaga gctacacaga 781 agacctattt ccggaacaat tacaactatg tcattcgggc taaagttaaa gagataaaga 841 ctaagtgcca tgatgtgact gcagtagtgg aggtgaagga gattctaaag tcctctctgg 901 taaacattcc acgggacact gtcaacctct ataccagctc tggctgcctc tgccctccac 961 ttaatgttaa tgaggaatat atcatcatgg gctatgaaga tgaggaacgt tccagattac 1021 tcttggtgga aggctctata gctgagaagt ggaaggatcg actcggtaaa aaagttaagc 1081 gctgggatat gaagcttcgt catcttggac tcagtaaaag tgattctagc aatagtgatt 1141 ccactcagag tcagaagtct ggcaggaact cgaaccccg gcaagcacgc aactaaatcc 1201 cgaaatacaa aaagtaacac agtggacttc ctattaagac ttacttgcat tgctggacta 1261 gcaaaggaaa attgcactat tgcacatcat attctattgt ttactataaa aatcatgtga 1321 taactgatta ttacttctgt ttctcttttg gtttctgctt ctctcttctc tcaaccccctt 1381 tgtaatggtt tgggggcaga ctcttaagta tattgtgagt tttctatttc actaatcatg 1441 agaaaaactg ttcttttgca ataataataa attaaacatg ctgttaccag agcctctttg 1501 ctggagtctc cagatgttaa tttactttct gcaccccaat tgggaatgca atattggatg 1561 aaaagagagg tttctggtat tcacagaaag ctagatatgc cttaaaacat actctgccga 1621 tctaattaca gccttatttt tgtatgcctt ttgggcattc tcctcatgct tagaaagttc 1681 caaatgttta taaaggtaaa atggcagttt gaagtcaaat gtcacatagg caaagcaatc 1741 aagcaccagg aagtgtttat gaggaaacaa cacccaagat gaattatttt tgagactgtc 1801 aggaagtaaa ataaatagga gcttaagaaa gaacattttg cctgattgag aagcacaact 1861 gaaaccagta gccgctgggg tgttaatggt agcattcttc ttttggcaat acatttgatt 1921 tgttcatgaa tatattaatc agcattagag aaatgaatta taactagaca tctgctgtta 1981 tcaccatagt tttgtttaat ttgcttcctt ttaaataaac ccattggtga aagtcccaaa 2041 aaaaaaaaaa aaaaaaa
Human SFRP3 protein sequence
                                                            (SEQ ID NO: 9)
MVCGSPGGMLLLRAGLLALAALCLLRVPGARAAACEPVRIPLCKSLPWNMTKMPNHLHHSTQANAILAI

EQFEGLLGTHCSPDLLFFLCAMYAPICTIDFQHEPIKPCKSVCERARQGCEPILIKYRHSWPENLACEE

LPVYDRGVCISPEAIVTADGADFPMDSSNGNCRGASSERCKCKPIRATQKTYFRNNYNYVIRAKVKEIK

TKCHDVTAVVEVKEILKSSLVNIPRDTVNLYTSSGCLCPPLNVNEEYIIMGYEDEERSRLLLVEGSIAE

KWKDRLGKKVKRWDMKLRHLGLSKSDSSNSDSTQSQKSGRNSNPRQARN
```

Coronary Disorders

Many patients are either at risk for or have suffered from various types of heart failure, including myocardial infarction, symptomatic or unsymptomatic left ventricular dysfunction, or congestive heart failure (CHF). An estimated 4.9 million Americans are now diagnosed with CHF, with 400,000 new cases added annually. This year over 300,000 Americans will die from congestive heart failure. Without therapeutic invention, cardiac muscle does not normally have reparative potential. The ability to augment weakened cardiac muscle as described herein is a major advance in the treatment of cardiomyopathy and heart failure. Despite advances in the medical therapy of heart failure, the mortality due to this disorder remains high, where most patients die within one to five years after diagnosis.

Coronary disorders are categorized into at least two groups. Acute coronary disorders include myocardial infarction, and chronic coronary disorders include chronic coronary ischemia, arteriosclerosis, congestive heart failure, angina, atherosclerosis, and myocardial hypertrophy. Other coronary disorders include stroke, myocardial infarction, dilated cardiomyopathy, restenosis, coronary artery disease, heart failure, arrhythmia, angina, or hypertension.

Acute coronary disorders result in a sudden blockage of the blood supply to the heart which deprives the heart tissue of oxygen and nutrients, resulting in damage and death of the cardiac tissue. In contrast, chronic coronary disorders are characterized by a gradual decrease of oxygen and blood supply to the heart tissue overtime causing progressive damage and the eventual death of cardiac tissue.

Cytoprotective Compounds

A cytoprotective (i.e., cell protective or regenerative) compound is a compound that that is capable of inhibiting cell damage such as apoptosis induced or oxidative-stress induced cell death. Cytoprotective compounds also include compounds that induce cell repair and regeneration. A cytoprotective compound is a polypeptide or nucleic acid encoding the polypeptide, the expression of which is increased in MSC-Akt cells under hypoxic conditions as compared to normoxic condition. For example, a cytoprotective polypeptide includes Sfrp-1, 2, and/or 3, adipsin, adrenomedullin, chemokine (C—C motif) ligand 2, cysteine rich protein 61, lysyl oxidase-like 2, serine proteinase inhibitor or vascular endothelial growth factor or fragment thereof. Other proteins/polypeptides with cytoprotective and regenerative properties include h1, 5, 8, 12, and 13. In some aspects the compound is a nucleic acid that increases expression of a nucleic acid that encodes a polypeptide or an agonist of a cytoprotective polypeptide.

Therapeutic Methods

The invention provides methods of inhibiting cell or tissue damage and ischemic or reperfusion related injuries. Also included are methods of regenerating injured myocardial tissue. The therapeutic methods include administering to a subject, or contacting a cell or tissue with a composition containing a cytoprotective compound.

Cell/tissue damage is characterized by a loss of one or more cellular functions characteristic of the cell type which can lead to eventual cell death. For example, cell damage to a cardiomyocyte results in the loss contractile function of the cell resulting in a loss of ventricular function of the heart tissue. An ischemic or reperfusion related injury results in tissue necrosis and scar formation.

Injured myocardial tissue is defined for example by necrosis, scarring or yellow softening of the myocardial tissue. Injured myocardial tissue leads to one or more of several mechanical complications of the heart, such as ventricular dysfunction, decrease forward cardiac output, as well as inflammation of the lining around the heart (i.e., pericarditis). Accordingly, regenerating injured myocardial tissue results in histological and functional restoration of the tissue.

The cell is any cell subject to apoptotic or oxidative stress induced cell death. For example, the cell is a cardiac cell such as a cardiomyocyte, a liver cell or a kidney cell. Tissues to be treated include a cardiac tissue, a pulmonary tissue, or a hepatic tissue. For example, the tissue is an muscle tissue such as heart muscle. The tissue has been damaged by disease or deprivation of oxygen.

Cells or tissues are directly contacted with a cytoprotective compound, e.g. by direct injection into the myocardium. Alternatively, the cytoprotective compound is administered systemically. The cytoprotective compounds are administered in an amount sufficient to decrease (e.g., inhibit) apoptosis induced or oxidative stress induced cell death as compared to untreated cells or tissues. Cells undergoing apoptosis are identified by detecting cell shrinkage, membrane blebbing, caspase activation, chromatin condensation and fragmentation as is well know in the art. Cell undergoing oxidative stress are identified by detecting an increase production of reactive oxygen species (ROS). A decrease in cell death (i.e., an increase in cell viability) is measured by using standard cell viability measurements such as BrdU incorporation assay and trypan blue exclusion.

The methods are useful to alleviate the symptoms of a variety disorders, such as disorders associated with aberrant cell damage, ischemic disorders, and reperfusion related disorders. For example, the methods are useful in alleviating a symptom of stroke, myocardial infarction, chronic coronary ischemia, arteriosclerosis, congestive heart failure, dilated cardiomyopathy, restenosis, coronary artery disease, heart failure, arrhythmia, angina, atherosclerosis, hypertension, renal failure, kidney ischemia or myocardial hypertrophy. The disorders are diagnosed and or monitored, typically by a physician using standard methodologies. Alleviation of one or more symptoms of the disorder indicates that the compound confers a clinical benefit, such as a reduction in one or more of the following symptoms: shortness of breath, fluid retention, headaches, dizzy spells, chest pain, left shoulder or arm pain, and ventricular dysfunction Therapeutic Administration The invention includes administering to a subject a composition comprising a cytoprotective compound (also referred to herein as a "therapeutic compound").

An effective amount of a therapeutic compound administered systemically in the range of about 0.1 mg/kg to about 150 mg/kg. Proteins or peptides are administered directly into the heart by injection at a dose of 1-1000 μg. For example, 10, 20, 30, 40, 50, 60, 75, 100 μg are administered by myocardial injection. Effective doses vary, as recognized by those skilled in the art, depending on route of administration, excipient usage, and coadministration with other therapeutic treatments including use of other anti-apoptotic agents or therapeutic agents for treating, preventing or alleviating a symptom of a particular cardiac disorder. A therapeutic regimen is carried out by identifying a mammal, e.g., a human patient suffering from (or at risk of developing) an cardiac disorder, using standard methods.

The pharmaceutical compound is administered to such an individual using methods known in the art. Preferably, the compound is administered orally, nasally, topically or parenterally, e.g., subcutaneously, intraperitoneally, intramuscularly, and intravenously. The compound is administered prophylactically, or after the detection of an cardiac event such as a heart attack. The compound is optionally formulated as a component of a cocktail of therapeutic drugs to treat cardiac disorders. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for administration utilizing conventional methods. For example, cytoprotective compounds are formulated in a capsule or a tablet for oral administration. Capsules may contain any standard pharmaceutically acceptable materials such as gelatin or cellulose. Tablets are formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art.

Cytoprotective compounds are effective upon direct contact of the compound with the affected tissue, e.g. heart muscle. Alternatively, cytoprotective compounds are administered systemically. Additionally, compounds are administered by implanting (either directly into an organ such as the heart or subcutaneously) a solid or resorbable matrix which slowly releases the compound into adjacent and surrounding tissues of the subject. For example, the compound is delivered to the cardiac tissue (i.e., myocardium, pericardium, or endocardium) by direct intracoronary injection through the chest wall or using standard percutaneous catheter based methods under fluoroscopic guidance for direct injection into tissue such as the myocardium or infusion of an inhibitor from a stent or catheter which is inserted into a bodily lumen. Any variety of coronary catheter, or a perfusion catheter, is used to administer the compound. Alternatively, the compound is coated or impregnated on a stent that is placed in a coronary vessel.

The present invention is further illustrated, but not limited, by the following examples.

EXAMPLE 1

The Family of Secreted Frizzled Related Proteins Mediate Akt-MSC Cardiac Protection and Repair Through Paracrine Mechanisms Loss of myocardial tissue due to ischemia and infarction usually leads to inflammation, scarring and cardiac myocyte hypertrophy. However, since the myocardium has limited endogenous repair and regenerative capacity, these compensatory pathophysiological responses to myocardial damage are frequently inefficient to sustain cardiac function, resulting eventually in cardiac dilation and failure.

Cellular cardiomyoplasty has been proposed as a potential approach for reconstitution of infarcted myocardium and recuperation of cardiac function. Several cell-based strategies have evolved using a variety of alternatives, such as skeletal muscle myoblasts, embryonic stem cells, fetal cardiomyocytes, myocardial stem cells and marrow-derived mesenchymal stem cells (MSC). Among these methods, the use of MSCs has shown much promise for clinical applications.

Protection may result from differentiation of donor cells into cardiomyocytes, fusion of donor cells with host cardiomyocytes, or through enhanced myocardial perfusion. A significant mechanism by which cardiomyocyte survival/function is mediated by stem cells is through paracrine effects.

Intramyocardial transplantation of MSCs overexpressing the survival gene Akt (Akt-MSCs) resulted in reduced infarct size and volume, ventricular remodeling and cardiac dysfunction, 2 weeks after infarction, when compared to hearts transplanted with control MSCs alone. Moreover, conditioned medium from Akt-MSCs provided cytoprotection of cardiac myocytes exposed to hypoxia in vitro and once injected into infarcted hearts dramatically limited the infarct size and prevented ventricular dysfunction within 72 hours. Since this early effect cannot be readily explained by significant regeneration of cardiac myocytes from the donor cells or enhancement of angiogenesis, these data indicate that the observed effect is due to paracrine factors released by the Akt-MSCs that prevent myocyte loss.

Although it has been reported that native MSCs can secrete angiogenic factors and cytokines, the ability of bone marrow derived MSCs, especially Akt-MSCs, to produce factor(s) capable of acutely protecting the cardiomyocytes from cell death has not been previously documented. Given that apoptosis is the principal cause of myocytes loss in the acute phase of MI, therapeutic methods that prevent or reduce apoptotic cell death are effective in reducing the severity and extent of myocardial infarction. Paracrine factor(s) secreted by MSCs were identified, and biological evidence of their therapeutic potential is described below.

A strategy was developed that allows large-scale identification and functional screening of secreted factors that are responsible for the enhanced cytoprotective effect of the Akt-MSCs. First, microarray analysis of Akt-MSC and control MSC under normoxia and 6 h of hypoxia was performed. Approximately 62 transcripts that were differentially regulated between the Akt-MSC and control MSC under normoxia or hypoxia encode for known secreted proteins based on their annotation. Included in this list were three members of the secreted Frizzled-related protein (Sfrp) family, Sfr1, Sfrp2 and Sfrp3. Sfrps bind to Wnt ligands or their frizzled receptors and modulate Wnt signaling. All three factors are associated with regulation of cell fate, differentiation, and cell death and cell growth. The data described herein provide evidence that Akt-MSCs exert an early protection to the injured heart by secreting Sfrps, which then modulate the X pathway in cardiac myocytes to prevent cell death.

The following material and methods were used to generate the data described below.

Purification of mesenchymal stem cells and retroviral transduction.

Bone marrow cells from 8-10 week-old wild type male C57BL/6J mice (Jackson Laboratory), were collected in a-modified minimum essential media supplemented with 17% fetal bovine serum; 100 units/ml penicillin, 100 mg/ml streptomycin; amphotericin B 0.25 mg/ml. Mononuclear cells were then isolated from aspirates by Ficoll-Paque (Amersham Biosciences) gradient centrifugation. For the retroviral transduction, murine Akt1 cDNA tagged with a c-myc epitope by PCR-amplification was cloned into pMSCV-IRES-GFP vector. To overexpress Akt/GFP (Akt-MSC) or GFP alone (GFP-MSC), MSCs were infected with high-titer VSV-G pseudotyped retrovirus.

Gene Expression Profiling and RNA Validation

Eight micrograms of total RNA from mouse GFP-MSCs and Akt-MSCs (n=3 per group) under normoxia or hypoxia (6 hours) were used for microarray analysis. Affymetrix GeneChips of Mouse Genome 430 2.0 Arrays (Affymetrix. CA), which allows analysis of ~45000 transcrips, was performed in triplicate, and analyzed with Affymetrix Microarray Suite (MAS 5.0). For further analysis various Dhip was used. All possible comparisons (Akt-MSC normoxia vs. GFP-MSC normoxia, Akt-MSC hypoxia vs. GFP-MSC hypoxia, GFP-MSC hypoxia vs. GFP-MSC normoxia and Akt-MSC hypoxia vs. Akt-MSC normoxia) were tested. The transcripts were then annotated using various databases to compile a list of potent secreted candidates.

Gene expression profiling was determined by quantitative real-time RT-PCR (QPCR) for selected genes with appropriate primer mixtures (TaqMan® Gene Expression Assays, No. 4331182) from Applied Biosystems (Sfrp1, Mm00489161; Sfrp2, Mm00485986; Sfrp3(Frzb), Mm00441378; Gapdh, Mm99999915).

Conditioned Media Collection and Concentration

Passage 3 to 5 GFP-MSCs and Akt-MSCs reached to 90% confluence in 10 cm dishes. The cells were then left either into a standard incubator or the hypoxic chamber in the medium (αMEM+0.2% FBS+ITS) for 6 hours. Plates with medium only were also left at the same conditions as control-conditioned medium. The medium was concentrated up to 50× using a Millipore system with membrane (Amicon Ultra-15).
Western Blotting Proteins from conditioned medium from MSCs were separated by SDS page gel (Invitrogen) and transferred to nitrocellulose membranes (Bio-Rad). The blots were incubated with Sfrp2 primary antibody (Santa Cruz Biotechnology, Inc.) and then with appropriate secondary antibody conjugated with horseradish peroxidase (Amersham Biosciences). Complexes were detected by chemiluminescence (Lumi-GLO, Cell Signaling).
Suppression of Secreted Factor Effect by siRNA GFP-MSCs or Akt-MSCs were incubated overnight with OptiMEM medium containing 1 µM siRNA for Sfrps (Sfrp1, sense (5'→3'): CGGAUUGUAAAGAACUGCAUU (SEQ ID NO:10), antisens (5'→3'): UGCAGUUCUUUACAAUC-CGUU (SEQ ID NO:11); Sfrp2, sense (5'→3'): GGACGA-CAACGACAUCAUGUU (SEQ ID NO:12), antisense (5'→3'): CAUGAUGUCGUUGUCGUCCUC (SEQ ID NO:13); Sfrp3, sense (5'→3'): CCGUCAAUCUUUAUAC-CACUU (SEQ ID NO:14), antisense (5'→3'): GUG-GUAUAAAGAUUGACGGUG (SEQ ID NO:15); Ambion). Rhodamine-labeled GFP siRNA (Qiagen) was used to assess the efficiency of transfection. Cells were incubated in normal medium for 48 hours, then exposed to a serum free medium (αMEM+0.2% FBS+ITS) at normoxia or hypoxia as described above. The medium was concentrated for further analysis. The efficiency of the siRNA-mediated reduction of Sfrps was assessed by QPCR using 18S as a control.
Adult Rat Ventricular Myocyte Isolation and Quantification of Apoptotic Cardiomyocytes Adult rat ventricular myocytes (ARVMs) were isolated by enzymatic dissociation. $1 \times 10^6$ cells were incubated in 10 cm dishes (Becton Dickinson) overnight with full 199 medium (0.2% albumin, 2 mM carnitine, 5 mM creatine, 5 mM taurine and 1 µg/ml of recombinant human insulin, Sigma). On the following day, the medium was replaced with optimal medium according to different assays. Hypoxic condition was created by incubating the cells at 37° C. into a hypoxia chamber with an atmosphere of 5% $CO_2$/95% $N_2$. Oxygen level into the chamber was controlled to 0.5%.

Apoptosis was determined by measuring the activity of cleaved-caspase 3 using a caspase-specific fluorogenic substrate according to the protocol for Caspase 3 assay kit (Sigma, St. Louis, Mo.). ARVMs were lysed after treatment with SFRPs for 24 hours under hypoxia. 5 ul of cell extract was incubated in reaction buffer at room temperature for 1 hour. The enzyme-catalyzed release of 7-amino-4-methyl coumarin (AMC) was measured by a fluorescence microplate reader. Fluorescent units were converted to pmole AMC/µl sample/min/µg protein, using a standard curve of AMC.
Quantitation of Morphologic Changes of ARVC Following Hypoxic Exposure Isolated cardiomyocytes were seeded in multi-well plates (Becton Dickinson, Franklin Lakes, N.J., USA) precoated with laminin (1 µg/cm$^2$) and left overnight in standard growth medium (M199). One day later, the medium was replaced by serum-free medium with different doses of Sfrp2. The ARVCs were then placed in the hypoxia chamber. The viability of the ARVCs was evaluated on the basis of their morphology using a phase contrast microscope, and rod-shaped cardiomyocytes were considered viable. The number of round shaped cardiomyocytes was counted in 6 random high power fields and expressed as a percentage of total number of cells.

Myocardial Infarction Model and Determination of Infarct Size

Ligation of the left anterior descending coronary artery was performed on 170 to 200 grams female Sprague Dawley rats (Harlan World Headquarters, Indianapolis, Ind.). A left thoracotomy was performed under anesthesia, and the vessel was ligated with a silk suture at midway between the left atrium and the apex of the heart. The infarction was then assessed by the change of color and kinesis of the apex and the anterior-lateral wall. Thirty minutes later 250 µl conditioned media was injected in 5 different sites around the border zone. An equivalent amount of PBS was injected in the control group. Then the wound was sutured immediately.

Infarct size was analyzed by staining the tissue 5 min at 37° C. with planar morphometry in triphenyl tetrazolium chloride (TTC, Sigma Chemicals) followed by fixation of 12 hours in 10% phosphate-buffered formalin, and expressed as a percentage of the total ventricular area.
Akt Regulated Expression of Sfrps in MSCs Since the secreted frizzled-related sequence, protein 2 (Sfrp2) appeared to be expressed highly only in Akt-MSCs, and two other members of the same family (Sfrp1 and Sfrp3) were also upregulated in these cells, efforts were focused on these molecules. First, MSCs-Akt and control Gfp-MSCs were cultured under normoxia or 6 hours of hypoxia and the RNA was collected and used to confirm the microarray data by quantitative PCR (Q-PCR). The expression pattern of all genes Sfrp1, Sfrp2 and Sfrp3 was consistent with the microarray results. Although both Sfrp1 and Sfrp3 exhibited a consistent trend (P<0.1) of being expressed higher in Akt-MSCs, the most dramatic and significant differences were shown in the Sfrp2 levels (almost undetectable in control cells as opposed to high levels in Akt-MSCs). No significant changes were observed in the levels of all three genes in regard to hypoxia treatment in either control MSC or Akt-MSCs.

To further validate the observations at the protein level and to evaluate the effect of Akt on Sfrp2 expression, control mouse MSCs and Akt-MSCs were cultured under normoxic or hypoxic conditions for 6 hours with PI3K inhibitor (LY294002 50 mM) or vehicle. The conditioned medium was then collected and concentrated for protein analysis. Sfrp2 was highly expressed in the conditioned medium from the Akt-MSC cells at both normoxia and hypoxia. The levels of Sfrp2 were low or undetectable in the supernatant from GFP-MSCs under normoxia or hypoxia. Furthermore, the expression of Sfrp2 in the Akt-MSC cells was dependent to the PI3K pathway since inhibition of the PI3K, also abolished Sfrp2 expression from the medium. Sfrp1 and Sfrp3 showed similar patterns of protein expression.
Akt-MSCs Promote Cardiac Myocyte Cell Survival After Injury Through Sfrp Mediated Paracrine Effects To determine whether Sfrps are a key mediator of the early cytoprotective effect of the conditioned medium in vitro, the effects of conditioned medium from cultured Akt-MSCs (Akt CM) and Akt-MSCs that did not express Sfrp1, Sfrp2 or Sfrp3 due to siRNA treatment (Akt-Sfrp2 CM) on the viability of adult rat cardiac myocytes (ARVCs) subjected to hypoxia were assessed. The conditioned media (CM) from Akt-MSCs of Gfp-MSCs was collected and concentrated after 6 hours of exposure to either normoxia or hypoxia. The CM was then added to ARVCs that were exposed to 24 h of hypoxia. The experimental conditions included ARVCs that were incubated with either control conditioned medium (Ctr CM), conditioned medium from Akt-MSCs or Gfp-MSCs (Akt CM and Gfp CM) and conditioned medium Akt-MSCs or Gfp-MSCs that did not express Sfrp2 due to siRNA treatment (Akt minus Sfrp2 CM and Gfp minus Sfrp2 CM respectively). The data showed that ARVCs maintained under normoxic conditions for 24 hours were viable and exhibited their typical rod-shaped appearance. Exposure of ARVCs to 24 hours of hypoxia in control conditioned medium (Ctr CM) resulted in a 200% increase in cell death as indicated by caspase activity assay. Moreover, as expected the addition of Gfp CM had no effect whereas addition of Akt CM resulted in a reduction of caspase activity (64% as compared to Ctr CM) to levels similar to normoxic conditions. However, exposure of hypoxic myocytes to Akt minus Sfrp2 CM resulted in increased caspase activity compared to Ctr CM indicating higher cell death levels. Finally, reduction of Sfrp2 expression in the Gfp CM did not have did not have any significant impact on its effect on hypoxic cardiac myocytes.

To examine the direct effect of Sfrps on ARVCs we also performed gain of function experiments in vitro. ARVCs were maintained in standard growth medium at normoxia or at 24 h hypoxia. Sfrp1, Sfrp2, Sfrp3 or vehicle was then added at various concentrations and apoptosis levels were assessed as before by measuring caspase activity. Treatment with as low as 0.1 ng/ml of Sfrp1 or Sfrp2 resulted in significant reduction in caspase activity (36% and 33% respectively). However, higher concentrations of Sfrp1 showed reduced protection. On the contrary, Sfrp2 mediated reduction of cell death was positive correlated to higher concentrations of the molecule and seemed to plateau around the concentration of 10 ng/ml (55% reduction in caspase activity). Sfrp3 treatment reduced caspase activity only in concentrations higher than 10 ng/ml and overall was less potent that the other molecules (54% reduction at 500 ng/ml).

Finally, to corroborate the results from the apoptosis assays, the relative number of healthy ARVCs after 24 hours of hypoxia was assessed based on their ATP synthesis levels. For this, again the cells were grown in normoxia or hypoxia with PBS or Akt CM, Akt-Sfrp2 CM, 10 ng/ml Sfrp2, or 500 ng/ml Sfrp3 for 24 h. Exposure of ARVCs to 24 h plus Akt CM increased cell viability by 35% whereas medium from Akt cells that did not express Sfrp2 increased cell viability only by 9%. Treatment with Sfrp2 and Sfrp3 resulted in 24% and 17% increase in viability respectively.

Sfrp Treatment Protects the Heart from Myocardial Injury

To elucidate the therapeutic potential of the Sfrps, we studied the direct effects of Sfrps on infarct size by intramyocardial injection of Sfrp1, Sfrp2 or Sfrp3 peptide. For this, 1 µg of Sfrp1, Sfrp2 or Sfrp3 were injected into 5 different sites in the heart at the infarct border zone 30 minutes after coronary artery occlusion. Additional groups included hearts injected with PBS as negative control, hearts injected with Akt CM as positive control and hearts injected with Akt minus Sfrp2 CM to provide further evidence of Sfrp2 role in the protective Akt-MSC CM mediated cardiac protection in vivo. Hearts were isolated 72 hours later and infarct size was estimated by TTC staining. Injection of Sfrp2 had an effect of 69% reduction of infarct size, while injection of the same concentration of Sfrp1 resulted in 50% reduction in infarct size and the same dose of Sfrp3 did not have any effect on infarct size. Since Sfrp2 have been shown to have the most potent effect from all the three Sfrps tested, its physiological significance in Akt-MSC mediated myocardial protection in vivo was also evaluated. Injection of Akt CM in infarcted hearts resulted in 71% reduction in the infarct size after MI within 72 hours, whereas injection Akt minus Sfrp2 CM did not show any significant protection. These results indicate that Sfrps secreted from Akt-MSCs protects the myocardium from injury.

Sfrps Mediate Cardioprotection

Despite vigorous efforts and the great potential of cell-based therapies for cardiac disease, the mechanisms underlying their therapeutic effect are still under debate. The data described herein indicates that MSCs exert an early protective effect in the injured myocardium by preventing myocyte cell death. This effect is enhanced by the overexpression of Akt and includes paracrine factors that regulate the Wnt signaling pathway in cardiac myocytes. Sfrp modulators of Wnt pathway protect from hypoxia cell death in vitro and result in reduction of infarct size in vivo.

Members of the Secreted frizzled-related protein (Sfrp) family act as modulators of the Wnt signaling pathway thereby influencing a range of biological processes, such as cell fate, cell adhesion, differentiation and survival. Sfrps are inhibitors of the Wnt signaling pathway. They act through binding of Wnts and altering their ability to bind to their frizzled receptors or by forming non functional complexes with the frizzled receptors themselves. However, some studies suggest that Sfrp1 at low concentrations may actually promote Wnt signaling. Furthermore, it has been reported that similar concentrations of Sfrp1 and Sfrp2 result in different cellular responses. For instance, Sfrp1 has been shown to sensitize cells to TNF induced apoptosis whereas Sfrp2 conferred resistance. A proposed explanation for these observations is that the Sfrp specific effects are closely dependent on the range of their Wnt partners present, the relative affinities of different Sfrps for Wnt or Frizzled receptors, tissues specific responses or biphasic responses to different concentrations of Sfrp. The present data support this mechanis, since the three different Sfrps tested confered variable degrees of protection to cardiac myocytes and these effect was dependent on their concentration levels.

Prior to the invention, little was known about the role of Sfrps in cardiac tissue. Sfrp1 has been associated with heart morphogeneiss, whereas Sfpr3 and Sfrp4 were found to be upregulated in volume overload induced hypertrophy. Evidence suggests that they are play a role during cardiac ischemia but again their role is diverse and not fully understood. For instance, overexpression of Sfrp1 seemed to protect the heart from injury in a model of coronary ligation but has been reported to alleviate it and reverse the benefit of preconditioning in a model of ischemia/reperfusion. Similarly few studies have been conducted in regard to the role of Wnt singaling in cardiac myocyte survival. The present data provides evidence that Sfrp activates/inhibits Wnt signaling.

The data do not exclude additional paracrine effects from other proteins secreted by the Akt-MSCs. Indeed, other secreted molecules are also expressed and are involved in different aspects of cardiac repair such as immunological responses, angiogenesis, recruitment/expansion of cardiac stem cells, regeneration and/or remodeling. For example, administration of vascular endothelial growth factor A (a growth factor with higher levels in Akt-MSCs) resulted in repaired myocardium by promoting angiogenesis and vascularization. Moreover, paracrine factors exert not only individual effects, but in some examples, one factor enhances the effect of another, i.e, a synergistic relationship is present between the different secreted factors expressed by the MSCs. In other examples, the presence of one factor inhibits the effects of one or more others.

Paracrine factors, e.g., Sfrps, contained in conditioned medium from Akt-MSCs are useful in therapeutic methods to prevent or reduce cell death, e.g., apoptotic cell death, of cardiac cells. The data indicates that simple administration of Sfrp2 alone or in combination with other molecules achieve cardioprotective results similar and in some cases better than those seen with stem cell based therapy. Methods that employ these paracrine factors have numerous advantages over cell based therapies. For example, many of the difficulties of stem cell based therapy such as availability of cells, laborious maintenance of cell lines, limited alternative administration methods as well as difficulties in successful delivery and survival of the cells can be avoided. Administration of a peptide or a cocktail of peptides to the injured myocardium is a simpler, delivery methods, and dosages are more easily modified to achieve higher efficiency with lower toxicity or side effects and does not involve any of the ethical concerns associated with cell therapy.

EXAMPLE 2

Secreted Frizzled Related Protein 2 is the Key Stem Cell Paracrine Factor Mediating Myocardial Survival and Repair Using a comprehensive functional genomic strategy, Sfrp2 was shown to be a key stem cell paracrine factor that mediates myocardial survival and repair following ischemic injury. Sfrp2 modulates Wnt signaling, and cardiomyocytes treated with secreted frizzled related protein increase cellular β-catenin and up-regulate expression of anti-apoptotic genes. These findings demonstrate the key role played by Sfrp2 in mediating the paracrine effects of Akt mesenchymal stem cells on tissue repair and identify modulation of Wnt signaling as a strategy for treating heart disease.

Microarray data confirmed by Western blot analysis demonstrated that one of the most prominently expressed and secreted protein by Akt-MSC compared to native MSC is the Sfrp2. Quantitative PCR showed 100 fold up regulation of Sfrp2 mRNA in Akt-MSC compared to control MSC. Sfrps are secreted glycoprotein molecules that structurally resemble cell surface frizzled receptors but lack the transmembrane domain. They have been increasingly recognized as potent regulators of cellular Wnt signaling and have been implicated in diverse cellular processes such as regulation of cell fate, differentiation, proliferation and cell death.

Sfrp2 was found to play a major role in mediating the survival signal of Akt-MSC on the ischemic myocardium. The data shows that Sfrp2 exerted survival effects on ischemic cardiomyocytes and that the pro-survival effects of Akt-MSC were markedly attenuated upon knockdown of Sfrp2 using siRNA. Sfrp2 increased total cellular and nuclear β-catenin in cardiomyocytes in vitro. Stabilization of β-catenin has been demonstrated to protect neonatal rat cardiomyocytes against hypoxia/re-oxygenation induced apoptosis. The canonical Wnt, Wnt3a, was found to be up-regulated in ischemic cardiomyocytes in vitro, and Wnt3a induced apoptosis of cardiomyocytes. Sfrp2 blocked the pro-apoptotic effect of Wnt3a. The data indicate that Sfrp2 is a major paracrine mediator of Akt-MSC myocardial survival and reparative effects and indicate that modulators of Wnt signaling such as Sfrp2 are useful as therapeutic agents in the management of myocardial injury.

Experiments were carried out as described above. Further profiling of secreted factors to identify cytoprotective proteins is described below.

Profiling of Secreted Factors Expressed in MSCs

To identify potential Akt-MSC secreted candidate paracrine factors mediating myocardial cell survival following ischemic injury, Affymetrix GeneChip® Mouse Genome 430 2.0 Arrays, which allows analysis of approximately 45,000 transcripts was used. Expression levels and quality analysis were carried out with the Affymetrix MAS 5.0 software. Further analysis was performed using the dChip software based on the following filtering criteria: a) Transcripts expressed (P call) in at least one of the sample compared, b) Fold change: at least 1.2×, (90% lower bound confidence). Approximately 650 transcripts were differentially regulated between the Akt-MSC and the GFP-MSC. Included in this list were 169 transcripts with unassigned function. The set of 650 transcripts was queried for transcripts coding for secreted proteins. This analysis revealed 62 transcripts encoding for 51 unique genes that contribute to the paracrine effects of the MSC cells (Table 1).

TABLE 1

| Probe set | Gene Title | Gene Symbol | Fold change Akt vs. Gfp at normoxia | Fold change Akt vs. Gfp at hypoxia |
|---|---|---|---|---|
| 1426858_at | inhibin beta-B | Inhbb | −2.27 | −4.34 |
| 1423635_at | bone morphogenetic protein 2 | Bmp2 | −3.82 | −3.19 |
| 1456404_at | a disintegrin-like and metalloprotease (reprolysin type) with thrombospondin type 1 motif, 5 (aggrecanase-2) | Adamts5 | −1.22 | −3.08 |
| 1426152_a_c | kit ligand/stem cell factor | Kitl | −1.64 | −2.78 |
| 1427760_s_at | Proliferin | Plf | −3.15 | −2.61 |
| 1431056_a_at | lipoprotein lipase | Lpl | −2 | −2.58 |
| 1450658_at | a disintegrin-like and metalloprotease (reprolysin type) with thrombospondin type 1 motif, 5 (aggrecanase-2) | Adamts5 | −1.71 | −2.21 |
| 1449528_at | c-fos induced growth factor | Figf | −2.27 | −2.14 |
| 1438953_at | c-fos induced growth factor | Figf | −3.02 | −2.09 |
| 1415904_at | lipoprotein lipase | Lpl | −1.55 | −2.08 |
| 1418450_at | immunoglobulin superfamily containing leucine-rich repeat | Islr | −1.55 | −2.06 |
| 1426951_at | cysteine-rich motor neuron 1 | Crim1 | −2.41 | −2 |
| 1437218_at | fibronectin 1 | Fn1 | −1.89 | −1.97 |
| 1438954_x_at | c-fos induced growth factor | Figf | −3.03 | −1.96 |
| 1435603_at | secreted protein SST3 | SST3 | −1.12 | −1.93 |

TABLE 1-continued

| Probe set | Gene Title | Gene Symbol | Fold change Akt vs. Gfp at normoxia | Fold change Akt vs. Gfp at hypoxia |
|---|---|---|---|---|
| 1422561_at | a disintegrin-like and metalloprotease (reprolysin type) with thrombospondin type 1 motif, 5 (aggrecanase-2) | Adamts5 | −1.14 | −1.91 |
| 1418061_at | latent transforming growth factor beta binding protein 2 | Ltbp2 | −2.66 | −1.87 |
| 1451243_at | arginyl aminopeptidase (aminopeptidase B) | Rnpep | −1.34 | −1.86 |
| 1460302_at | thrombospondin 1 | Thbs1 | 1.03 | −1.84 |
| 1417234_at | matrix metalloproteinase 11 | Mmp11 | −1.59 | −1.82 |
| 1438936_s_at | Angiogenin | Ang | 1.18 | −1.82 |
| 1447862_x_at | thrombospondin 2 | Thbs2 | −1.33 | −1.8 |
| 1425985_s_at | mannan-binding lectin serine protease 1 | Masp1 | −1.72 | −1.79 |
| 1448117_at | kit ligand | Kitl | −1.23 | −1.79 |
| 1438937_x_at | Angiogenin | Ang | −1.22 | −1.76 |
| 1416164_at | fibulin 5 | Fbln5 | −1.35 | −1.72 |
| 1448823_at | chemokine (C-X-C motif) ligand 12 | Cxcl12 | −1.1 | −1.62 |
| 1415949_at | carboxypeptidase E | Cpe | −1.33 | −1.6 |
| 1416953_at | connective tissue growth factor | Ctgf | −6.01 | −1.57 |
| 1449187_at | platelet derived growth factor, alpha | Pdgfa | −2.33 | −1.55 |
| 1423396_at | Angiotensinogen | Agt | −2.48 | −1.51 |
| 1421228_at | chemokine (C-C motif) ligand 7 | Ccl7 | −3.4 | −1.25 |
| 1438133_a_at | cysteine rich protein 61 | Cyr61 | −3.93 | −1.18 |
| 1419662_at | Osteoglycin | Ogn | 2.19 | −1.07 |
| 1420380_at | chemokine (C-C motif) ligand 2 | Ccl2 | −6.73 | 1.01 |
| 1416039_x_at | cysteine rich protein 61 | Cyr61 | −4.61 | 1.04 |
| 1417130_s_at | angiopoietin-like 4 | Angptl4 | −1.04 | 1.02 |
| 1421991_a_at | insulin-like growth factor binding protein 4 | Igfbp4 | 2.32 | 1.19 |
| 1416371_at | apolipoprotein D | Apod | 1.88 | 1.34 |
| 1423294_at | mesoderm specific transcript | Mest | 2.21 | 1.34 |
| 1416594_at | secreted frizzled-related sequence protein 1 | Sfrp1 | 2.23 | 1.42 |
| 1450325_at | angiopoietin 4 | Agpt4 | 2.43 | 1.6 |
| 1417634_at | superoxide dismutase 3, extracellular | Sod3 | 4.31 | 1.61 |
| 1417256_at | matrix metalloproteinase 13 | Mmp13 | 2.21 | 1.74 |
| 1417633_at | superoxide dismutase 3, extracellular | Sod3 | 3.23 | 1.78 |
| 1429348_at | sema domain, immunoglobulin domain (Ig), short basic domain, secreted, (semaphorin) 3C | Sema3c | 2.61 | 1.92 |
| 1451866_a_at | hepatocyte growth factor | Hgf | 2.32 | 2.26 |
| 1429679_at | leucine rich repeat containing 17 | Lrrc17 | 2.36 | 2.35 |
| 1452436_at | lysyl oxidase-like 2 | Loxl2 | 1.8 | 2.62 |
| 1431591_s_at | interferon, alpha-inducible protein | G1p2 | 4.75 | 2.71 |
| 1448424_at | secreted frizzled-related sequence protein 3 | Sfrp3 | 3.15 | 3.14 |
| 1419043_a_at | interferon-inducible GTPase 1 | Iigp1 | 3.97 | 3.15 |
| 1419042_at | interferon-inducible GTPase 1 | Iigp1 | 4.61 | 3.55 |
| 1451959_a_at | vascular endothelial growth factor A | Vegfa | −1.07 | 3.64 |
| 1447839_x_at | Adrenomedullin | Adm | −3.72 | 4.03 |
| 1417867_at | Adipsin | Adn | 3.5 | 4.15 |
| 1448254_at | Pleiotrophin | Ptn | 5.21 | 4.48 |
| 1416211_a_at | Pleiotrophin | Ptn | 5.68 | 4.79 |
| 1416077_at | Adrenomedullin | Adm | −2.78 | 8.36 |
| 1419149_at | serine (or cysteine) proteinase inhibitor, clade E, member 1 | Serpine1 | −6.34 | 10.35 |
| 1448201_at | secreted frizzled-related sequence protein 2 | Sfrp2 | 10.04 | 11.66 |

Among these upregulated genes, Sfrp2 was the most dramatically upregulated. Other cytokines such as Vegf, Hgf and FGF were not differentially expressed between Akt-MSC and FP-MSC under normoxic conditions. The expression of Sfrp2 was Akt pathway dependent. The expression of the other Sfrp family members were minimally altered in Akt-MSC (FIG. 1A).

Akt Regulated Expression of Sfrps in MSCs

The results of microarray analysis was confirmed by quantitative PCR (Q-PCR). RNA was collected from cultured Akt-MSC and GFP-MSC that were cultured in vitro. As shown in FIG. 1B, the expression pattern of Sfrp1, Sfrp2 and Sfrp3 was consistent with the microarray results. Neither Sfrp1 and Sfrp3 was significantly upregulated in Akt-MSC vs GFP-MSC, whereas Sfrp2 expression was 100 fold higher in Akt-MSC.

Figure 2:
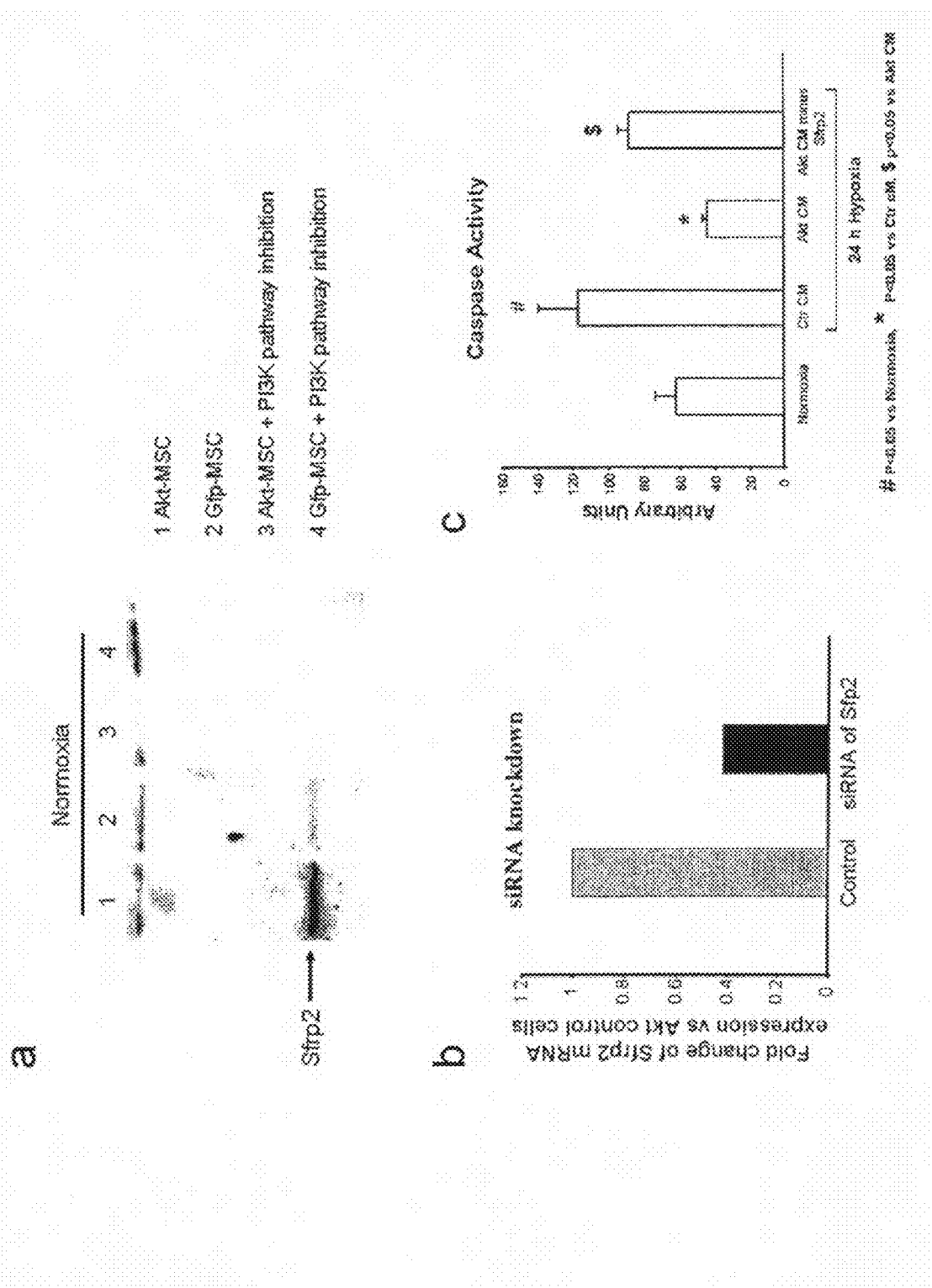
FIG. 2A is a photograph of results of a Western Blotting assay for Sfrp2. The data demonstrates presence of Sfrp2 protein in conditioned medium collected from AKT or GFP MSCs and inhibition of its accumulation in the medium in the presence of Pi3K inhibitor
FIG. 2B is a bar graph showing relative reduction in mRNA levels of Sfrp2 in Akt-MSC following knockdown of Sfrp2 with siRNA.
FIG. 2C is a bar graph showing the effect of conditioned medium on apoptosis in ARVCs. Caspase activity of ARVCs after 24 hours of hypoxia under different culture conditions (control conditioned medium, Ctr CM; Akt conditioned medium, Akt CM; Akt conditioned medium following Sfrp2 knockdown, Akt CM minus Sfrp2) demonstrates reduction of caspase activity following Akt-CM treatment and attenuation of this effect following treatment with Akt CM minus Sfrp2. These data demonstrate that paracrine factors from Akt-MSCs mediate the survival signaling on cardiomycytes.

To further validate our observations at the protein level and to evaluate the effect of Akt on Sfrp2 expression, control mouse MSCs and Akt-MSCs were cultured for 6 hours with PI3Kinase inhibitor (LY294002 50 mM) or vehicle. The conditioned medium was then collected and concentrated for Western blot protein analysis. As shown in FIG. 2A, Sfrp2 was secreted at high levels into the conditioned medium from the Akt-MSC cells (lanes 1). The levels of Sfrp2 were low or undetectable in the conditioned medium of GFP-MSCs (lanes 2). Furthermore, the expression/release of Sfrp2 in the Akt-MSC cells was dependent on the PI3K pathway since inhibition of the PI3K, abolished Sfrp2 accumulation in the medium (lanes 3).

Figure 3:
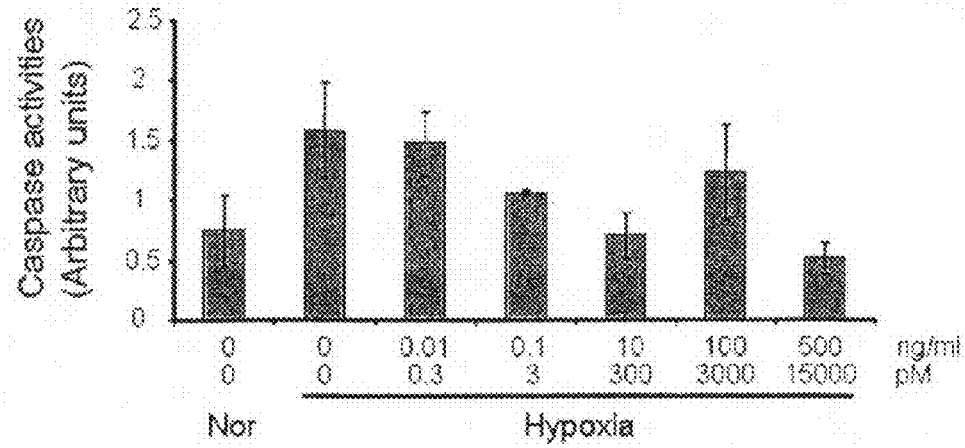
FIG. 3A is a bar graph showing the effect of Sfrp2 on caspase activity. Cleaved-caspase 3 activity as measured by a fluorometric assay demonstrated decreased caspase activity in hypoxic cardiomyocytes following Sfrp2 treatment in a dose dependent manner. The activity was calculated as fold changes with the same control.
FIG. 3B is a bar graph showing the number of round shaped cardiomyocytes that were counted in 6 random high power fields (40×) following 24 hour hypoxic exposure with/without Sfrp2 treatment. Data is expressed as a percentage of total number of cells present.
FIG. 3C is a series of representative high power field photographs demonstrating decreased number of round shaped cardiomyocytes following treatment with Sfrp2. Collectively, these data demonstrate that Sfrp2 decreases caspase 3 activity
Figure 3:
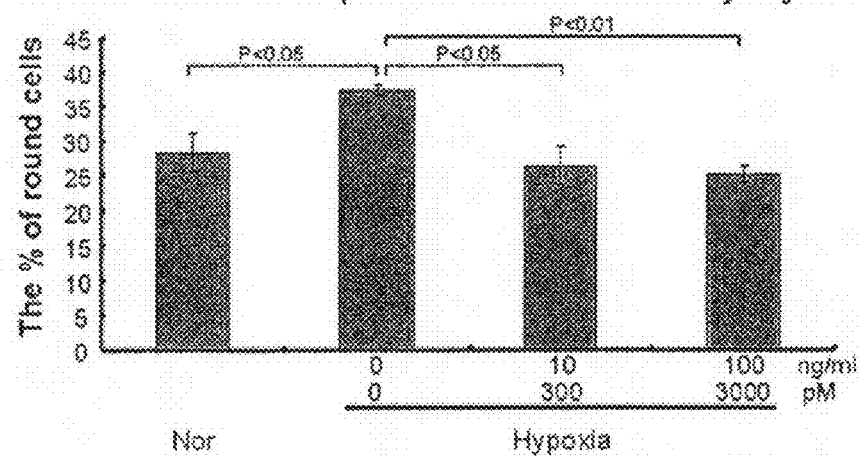
Figure 3:
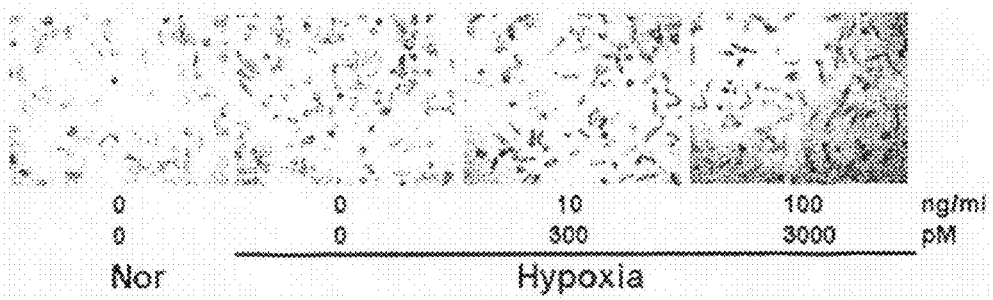

Akt-MSCs Promote Cardiomyocyte Cell Survival Through Paracrine Mechanisms Mediated By Sfrp To prove whether Sfrp2 is a key paracrine mediator of the survival signaling of Akt-MSC, the apoptotic response (caspase activity) of adult rat ventricular cardiomyocytes (ARVC) exposed to conditioned medium collected from Akt-MSC treated with siRNA (Akt-MSC minus Sfrp2 CM) against Sfrp2 was evaluated. ARVC were subjected to hypoxia for 24 hours in the presence of Akt-MSC CM, Akt-MSC minus Sfrp2 CM or standard growth medium (GM). (FIGS. 2B,C). ARVCs maintained in standard growth medium under normoxic conditions for 24 hours were viable and exhibited their typical rod-shaped appearance while ARVC grown in the same medium and subjected to 24 hour hypoxia exhibited a 82% increase in caspase activity (FIG. 2C). Compared to hypoxic ARVC maintained in standard growth medium, hypoxic ARVC exposed to Akt-MSC CM exhibited a 40% reduction in caspase activity (FIG. 3B). Moreover, exposure of hypoxic cardiomyocytes to Akt minus Sfrp2 CM resulted in a significant increase in caspase activity compared to hypoxic ARVC treated with Akt CM. A 33% increase in caspase activity was observed in hypoxic ARVC following knockdown of Sfrp2 expression in Akt-MSC. These observations demonstrate the key role played by Sfrp2 in mediating survival effects of Akt-MSC CM on cardiomyocytes.

To examine the direct effect of Sfrp2 on ARVCs, gain of function experiments were carried out. ARVCs were maintained in standard growth medium at normoxia or subjected to 24 h hypoxia. Sfrp2 or vehicle was then added at various concentrations and apoptosis levels were assessed by measuring caspase activity. Treatment with Sfrp2 resulted in significant reduction in caspase activity, and a dose dependent cytoprotective response was observed with increasing Sfrp2 concentrations up to 15 nM (FIG. 3A).

The cytoprotective effects of Sfrp2 on cardiomyocytes was confirmed by observing changes in cardiomyocyte cell morphology following exposure to hypoxia. ARVC following exposure to 24 hour hypoxia, lose their typical rod shaped morphology, become round in shape, subsequently detach and die. Hypoxia alone increased the number of round shaped cardiomyocytes by approximately 36% (FIGS. 3B, C). However when ARVC were treated with Sfrp2 (3 nM), the number of round shaped cardiomyocytes was decreased by approximately 31% compared to untreated controls (FIGS. 3B, C). The data strongly indicate that Sfrp2 promotes cardiomyocyte survival and protects cardiomyocytes from hypoxic injury.

Suppression of Sfrp2 expression in Akt-MSCs reduces the paracrine protection of myocardial injury in vivo.

Figure 4:
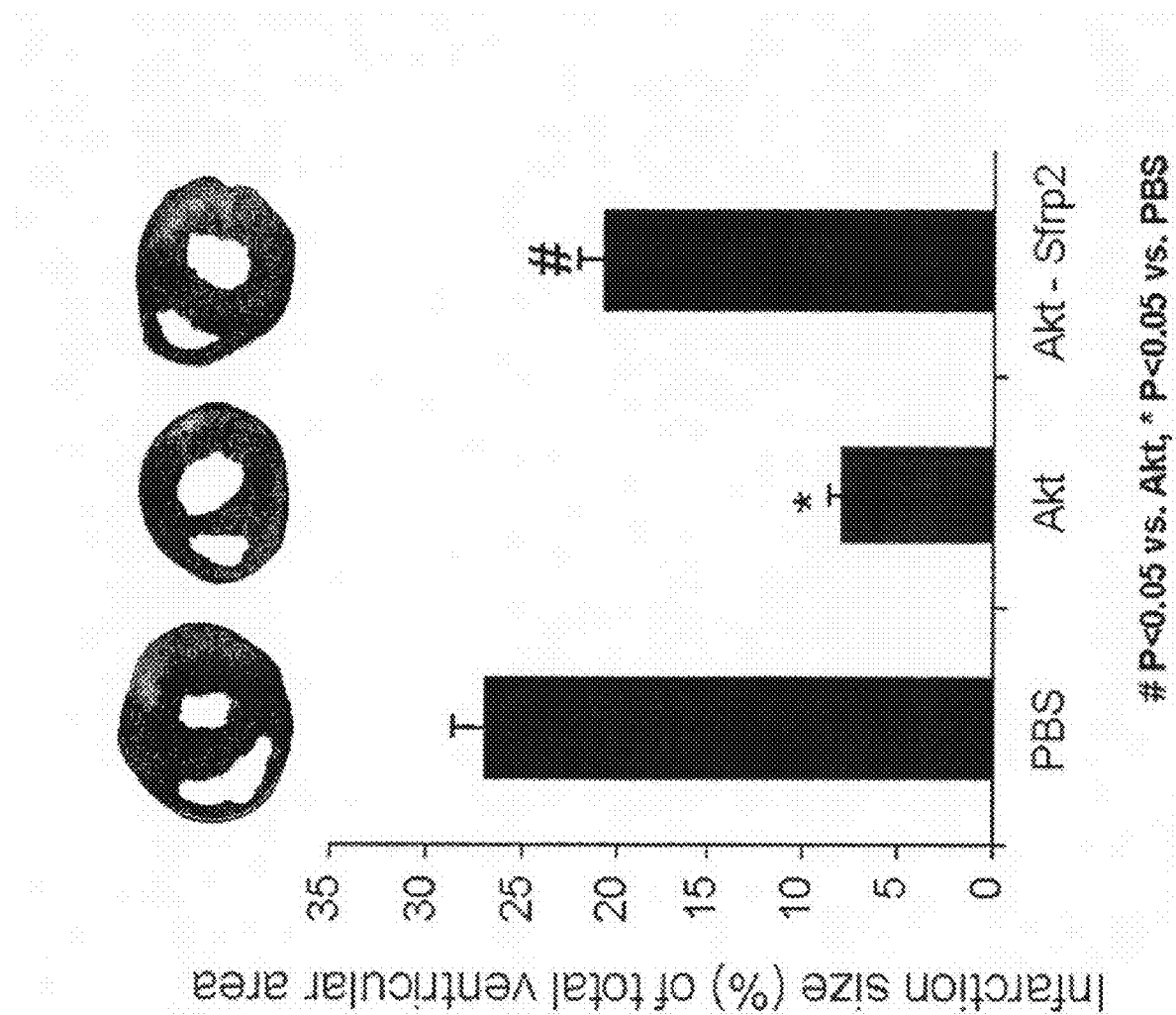
FIG. 4 is a bar graph showing that Sfrp2 decreased cardiac infarct size. Above each bar, is a photograph of TTC staining showing bi-ventricular sections of similar thickness perpendicular to the long axis of the heart. The staining data deomonstrates decreased infarct size with Akt-CM and Sfrp2 and attenuation of reduction in infarct size with Akt-Sfrp2. Infarct size is expressed as a percentage of the total ventricular area. Rat hearts were treated with PBS as control, Akt-MSCs CM (Akt), CM form Akt-MSCs that did express reduced levels of sfrp2 due to siRNA treatment (Akt-Sfrp2).

Experiments were carried out to evaluate the physiological significance of Sfrp2 in Akt-MSC mediated paracrine myocardial protection in vivo. To demonstrate the importance of Sfrp2 as a key paracrine factor mediating prosurvival effects of injected Akt-MSC, in vivo effects of conditioned medium collected from Akt-MSC treated with siRNA against Sfrp2 were compared with those of untreated Akt-MSC CM. Akt-MSC treated with siRNA against Sfrp2 had a 60% decrease in Sfrp2 mRNA expression following 48 hours of exposure to siRNA (FIG. 2B). The conditioned medium either from untreated or siRNA treated cells was collected, concentrated and then injected into 5 different sites at the infarct border zone 30 minutes after coronary artery ligation (a standard model for MI). Hearts were then isolated 72 hours later and infarct size was estimated by TTC staining. The results were analyzed by an investigator blinded to the treatment groups. As shown (FIGS. 4A, B) injection of Akt CM in infarcted hearts resulted in 71% reduction in the infarct size after MI within 72 hours, whereas injection of conditioned medium from siRNA treated Akt-MSC did not show any significant protection. Collectively, these results indicate that Sfrp2 possesses cell survival signaling properties and mediates myocardial protective effects following myocardial infarction.

Sfrp2 Leads to Upregulation of βCatenin in Hypoxic Cardiomyocytes

Figure 5:
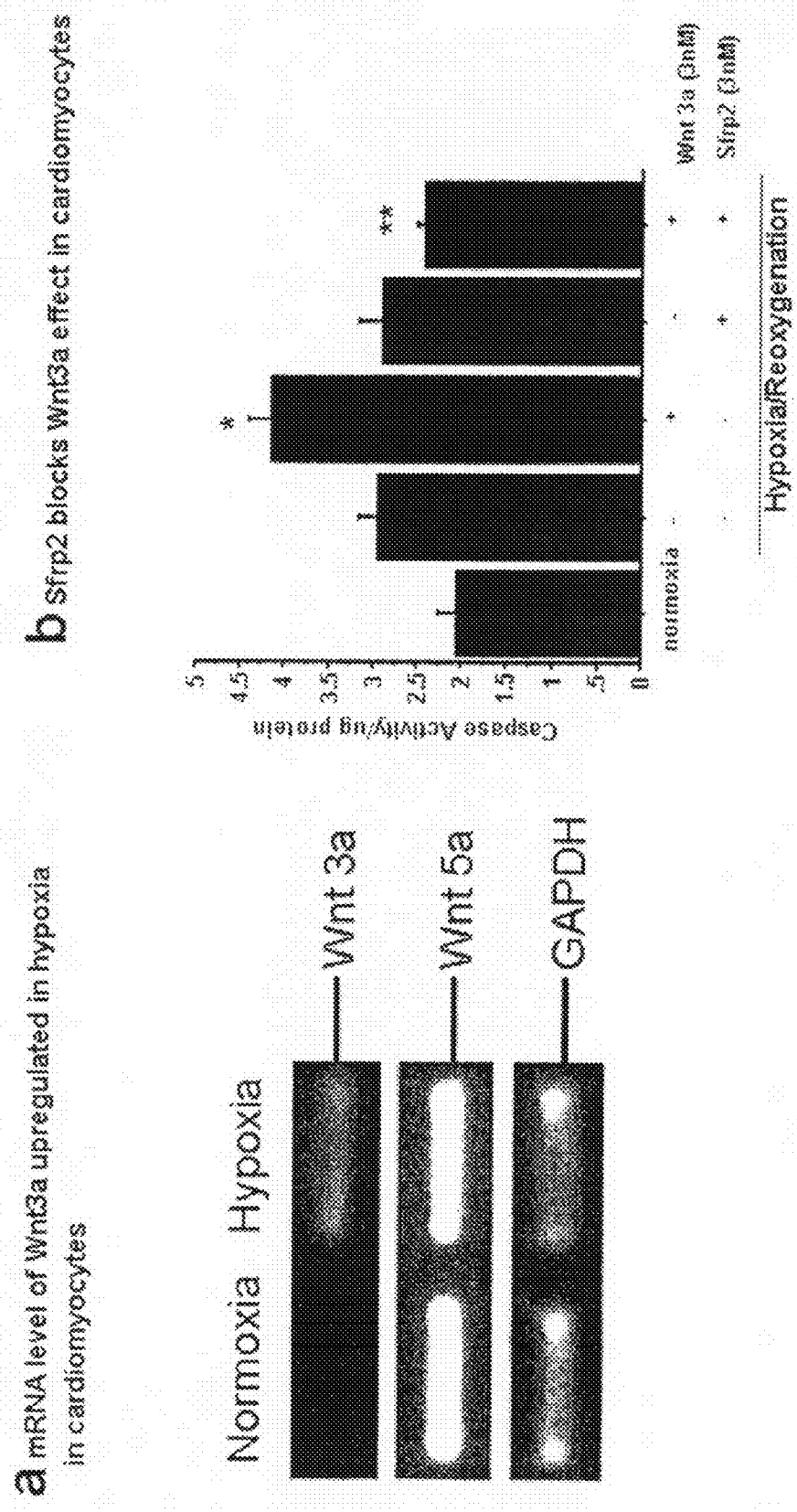

Sfrp2 is an antagonist of Wnt signaling. Unlike Sfrp1 which can potentiate Wnt signaling under certain conditions, Sfrp2 has not been known to activate Wnt signaling. However, evidence described herein indicates that Sfrp2 increases total cellular as well as nuclear β catenin mimicking canonical Wnt signaling. Using Western blotting, Sfrp2 was found to induce a dose dependent increase in nuclear as well as total cellular β catenin levels in cardiomyocytes exposed to hypoxia (FIG. 5C). Increased β catenin within cardiomyocytes is associated with increased cellular protection against ischemic injury in vitro. These data indicate that Sfrp2 promotes the survival of cardiomyocytes against hypoxia induced apoptosis via potentiation of canonical signaling. Experiments were then carried out to determine if Wnts are up-regulated in cardiomyocytes exposed to 24 hour hypoxia. The data indicated that Wnt3a was expressed at very low levels in normoxic cells but increased in hypoxic cells (FIG. 5A). Cardiomyocytes were incubated both under normoxia and hypoxia/reoxygenation with Wnt3a alone and in combination with Sfrp2. The data demonstrated that under normoxic conditions, as compared to control cardiomyocytes Wnt3a treatment resulted in a modest increase in caspase 3 activity which was attenuated by Sfrp2 treatment. Furthermore, under hypoxia/reoxygenation conditions, Wnt3a treatment resulted in a significant increase in caspase activity which was inhibited by the addition of Sfrp2 (FIG. 5B).

Figure 6:
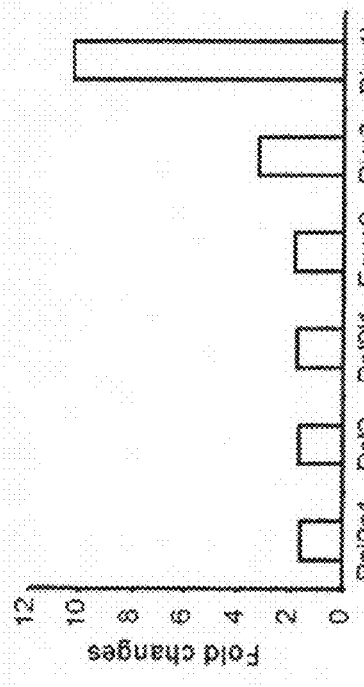
FIG. 6A is a bar graph showing genes upregulated by Sfrp2 under hypoxia. Microarray analysis demonstrates Sfrp2 mediated upregulation of Birc1b gene expression in hypoxic cardiomyocytes.
FIG. 6B is a photograph of an electrophoretic gel showing the effect of Sfrp2 on mRNA levels on Birc1b. RT-PCR confirmed increased Birc1b expression in hypoxic cardiomyocytes following Sfrp2 treatment.
FIG. 6C is a photograph of results of a Western Blot showing that beta-catenin levels are increased by Sfrp2. Western blotting for nuclear and total βcatenin expression in ARVCs demonstrates a reduction of βcatenin following hypoxia and upregulation following treatment with Sfrp2.
Figure 6:
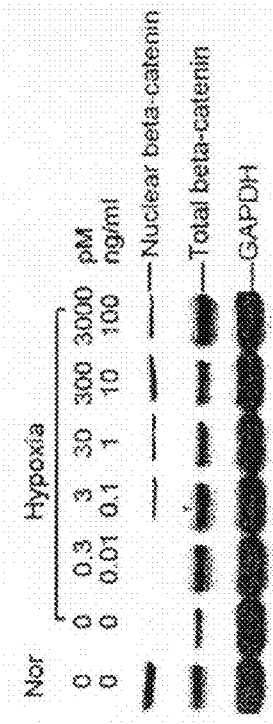
Figure 6:
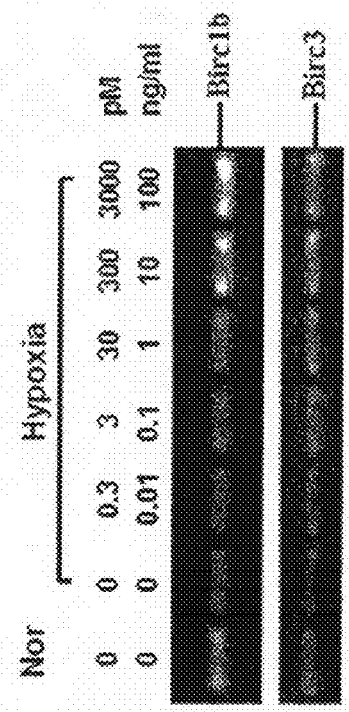

Sfrp2 Upregulates Expression of Anti-apoptotic Gene Birc1b in Hypoxic Cardiomyocytes To further investigate the molecular mechanism by which Sfrp2 protects cardiomyocytes from cell death, RNA from hypoxic cardiomyocytes following Sfrp2 treatment (10 ng/mL) was collected and expression of multiple genes involved in cell survival/death pathways was determined using microarray analysis. Using an oligo GE Array for rat signal transduction pathways, gene expression of 95 marker genes associated with 18 different signaling pathways was analyzed. In this analysis, 43 genes showed differential expression between the Sfrp2 treated and the control cardiomyocytes. Sfrp2 upregulated the expression of Birc1b, an anti-apoptotic gene belonging to the neuronal apoptosis inhibitory protein (NAIP) family. Expression of other cytoprotective genes such as Bcl2 were only minimally increased in hypoxic cardiomyocytes in the presence of Sfrp2 (FIGS. 6A, B).

Sfrp-based Therapy for Cardiac Disorders

Sfrp2 was identified as an Akt-MSC secreted protein exerting prosurvival effects on the myocardium. Several lines of evidence support the role of Sfrp2 as a principal mediator of anti apoptotic effects exerted on the myocardium by Akt-MSC. First, Sfrp2 expression is dramatically upregulated (100×) in Akt-MSC compared to GFP-MSC and its expression/secretion is dependent on the PI3 kinase/Akt pathway. Secondly, Sfrp2 conferred prosurvival effects on hypoxic cardiomyocytes. Moreover, knockdown of Sfrp2 expression resulted in the attenuation of the prosurvival action of Akt-MSC conditioned medium both in vitro and in vivo.

Sfrp2 is a secreted glycoprotein molecule that structurally resembles cell surface Frizzled receptors but lacks the latter's transmembrane domains. Sfrps compete with the frizzled receptor for Wnt ligands by direct binding of Wnts thus preventing activation of Wnt signaling in the cell. The Wnt family currently comprises 19 different proteins. Wnts are known to regulate organogenesis during embryonic development and in mammals and in other species such as amphibians and birds have been implicated in cardiac morphogenesis as well. They regulate diverse cellular processes such as proliferation, differentiation and apoptosis, but the role of the Wnts in regulating such processes in the post natal heart was not known. Although various Wnts such as Wnt10b and several frizzled receptors are expressed in the human heart, it was not known whether they play a role in cardiac homeostasis. The data described herein indicates that Sfrp2, a known modulator of Wnt signaling exerts prosurvival action on cardiomyocytes. The data demonstrate that Sfrp2 increases as well as nuclear βcatenin within the hypoxic cardiomyocyte in a dose dependent manner. βcatenin when activated translocates to the nucleus and initiates transcription of a wide variety of genes; thus the nuclear fraction represents a more accurate measure of activated βcatenin. Sfrp1 has previously been shown to potentiate Wnt signaling by directly binding to Frizzled receptors. In hypoxic cardiomyocytes, Sfrp2 binds locally present Wnts and alters the balance of intracellular Wnt signaling within a cardiomyocyte to favor a canonical pathway. Wnt3a was found to be upregulated in hypoxic cardiomyocytes. Wnt3a increases cardiomyocyte apoptosis and Sfrp2 blocks this effect of Wnt3a. Sfrp2 may also bind directly to frizzled receptor on cardiomyocytes activating the canonical pathway. The data indicate that Sfrp2 by increasing cellular and nuclear βcatenin enhances the survival response of cardiomyocytes against hypoxia induced apoptosis. Sfrp2 also upregulated expression of Birc1b, an anti-apoptotic gene belonging to the NAIP family. Sfrp2 mediated increased βcatenin activates transcription of anti-apoptotic genes such as Birc1b in hypoxic cardiomyocytes. Indeed, pharmacologic inhibition of GSK3β, resulting in increased βcatenin has been found to upregulate expression of anti-apoptotic genes such as Bcl2. Sfrp2 is involved in regulating cardiomyocyte cell survival and preserving cardiac function following myocardial infarction. Sfrp2 also plays a role as an important paracrine factor mediating beneficial effects of stem cell therapy. Sfrp2 alters the local milieu around the infarct zone to favor cardiomyocyte cell survival. Simple administration of Sfrp2 protein or fragments that modulate the Wnt-βcatenin pathway achieve results similar to stem cell based cardiac therapy, and a protein based therapy has advantages over cell based cardiac therapy for acute myocardial infarction and other ischemic cardiac disorders.

EXAMPLE 3

Sfrp2 Maintains Cells in a Stem Cell State

Sfrp2 was found to be strongly expressed by mouse embryonic stem cells (e.g., P19CL6 cell line which readily differentiates into cardiomyocytes under certain conditions). Sfrp2 was found to strongly inhibit differentiation of the murine embryonic P19Cl6 cell line. Overexpression of Sfrp2 or addition of recombinant Sfrp2 protein inhibited differentiation of these cells. This data indicates that Sfrp2, by inhibiting differentiation of stem cells and maintaining them in the undifferentiated state, plays a role in maintenance of a stem cell phenotype and self renewal of stem cells. When added to P19CL6 cells, purified Sfrp2 prevented these cells from differentiating into cardiomyocytes. This result indicates that Sfrp2 by inhibiting differentiation of embryonic stem cells and maintaining them in the undifferentiated state preserves a stem cell phenotype of such cells. Maintenance of sternness is a fundamental and essential property of stem cells. It is not only of essential biological importance but great clinical significance. For example, bone marrow transplantation involves selection and administration of hematopoietic stem cells. A composition, e.g., Sfrp2 or other paracrine factor, that maintain the stemness of embryonic and adult stem cells is useful to preserve and maintain stem cells for tissue repair and regeneration.

EXAMPLE 4

Identification of Protective Factors Secreted By Akt-MSC

Microarray analysis of Akt-MSC and control MSC under normoxia or hypoxia was performed to identify transcripts that were differentially regulated between these conditions. Using this approach, 61 proteins of know paracrine function were identified, e.g., pleiotrophin, chemokine ligands 2 and 7 and various angiogenic factors such as VEGFa, angiopoietin 4 and HGF. Upregulated transcripts with unassigned function were subjected to genomic analysis using a combination of bioinformatic software programs that allows predictions of potential secreted peptides. Putative secreted proteins thus indentified were then screened using siRNA technologies in a high throughout cell-based assays to examine key physiological mechanisms involved in the cardioprotective effects of Akt-MSCs. Using this approach, secreted proteins were indentified that are overexpressed in Akt-MSCs. One of these was highly expressed in Akt-MSCs but nearly undetectable in control MSCs. Permanent clones of Akt-siRNA knock down were then established for each of these genes and conditioned medium from these cells was compared to conditioned medium from Akt-MSCs for its cytoprotective effect in cardiac myocytes in vitro by apoptosis and cell viability assays.

Subsequently, the open reading frames of these novel transcripts were cloned and expressed in *E. coli* as maltose binding protein (MBP) fusion proteins. Compared with MBP alone, one of the MBP-novel fusion proteins (Protein #12; "h12") significantly reduced the $H_2O_2$-induced apoptosis in H9C2 myocytes. Protein 12 was re-cloned into pET vector to allow rapid purification as a 6×His tagged recombinant protein. Since Protein 12 is cysteine rich, purification was performed under denaturing condition and the protein was refolded by dialysis with a redox pair to promote disulfide bond formation. To test the cardioprotective effects of Protein 12, the effects of addition of this protein on $H_2O_2$-induced apoptosis in H9C2 myocytes was evaluated. Myocytes were treated with 100 µM $H_2O_2$ or vehicle and the levels of apoptosis was assessed by FACS analysis following Annexin V/PI staining. $H_2O_2$ induced high levels of early apoptosis, yielding approximately 30% Annexin V positive cells with less than 5% necrotic cells (PI positive). Pre-treatment of the cells with 10 nM of Protein 12 for 30 min reduced early apoptosis by nearly 50%. This protein significantly reduced $H_2O_2$ induced caspase 9 activity in adult rat cardiomyocytes by 38.5%, dramatically inhibited the mitochondrial release of cytochrome C and increased the total survival rate by 28%. The data indicate that this cysteine-rich Protein 12 possesses cardio-protective effects of Akt-MSCs.

A total of 5 transcripts with previously undefined function were found to account account for myocardial protection of AKT-MSCs. The open reading frame of these novel transcripts were subsequently cloned, expressed and purified from *E. coli*, as either fusion proteins of maltose binding protein-novel proteins or as 6×His tagged recombinant proteins. Protein No. 12, which is a cysteine-rich insoluble protein when expressed in *E. coli.*, was then purified under denaturing condition and refolded by dialysis with a redox pair to promote disulfide bond formation. This No. 12 protein was used in various assays for oxidative stress induced apoptosis in cardiomyocytes and was found to have a strong cardioprotective effect.

For Human No. 12, the coding sequence without the predicted N-terminal signal region (1158 base pairs) were amplified and cloned in-frame of protein translation into pMal-C vector to generate a fusion protein of maltose binding protein-Human No. 12, designated as MBP-h12 (~80 KDa). Expression was induced by IPTG in *E. coli.* and purification of MBP-h12 was done by standard affinity chromatography according to New England Biolab's instructions. MBP-h12 was further purified by FPLC system. Compared with control MBP alone, this MBP-h12 fusion protein significantly prevents $H_2O_2$-induced early apoptosis in H9C2 myocytes (~30% reduction of apoptosis), by Annexin V/PI double staining with FACS analysis. To gain further insight of protein No. 12' function in cardiovascular biology, same coding region (1158 base pairs) were re-amplified and cloned in-frame into pET 15b vector to generate 6×His-tagged recombinant protein, designated as His-h12 (~40 KDa). Protein was first purified under denaturing condition and refolded by dialysis with gradually decreasing amount of dithiothreital. Oxidized and reduced of glutathione as the 'redox pair' was added in the final step to promote disulfide bond formation. Refolded His-h12 proteins were dialyzed extensively in PBS and were used in subsequent apoptosis assays.

Figure 7:
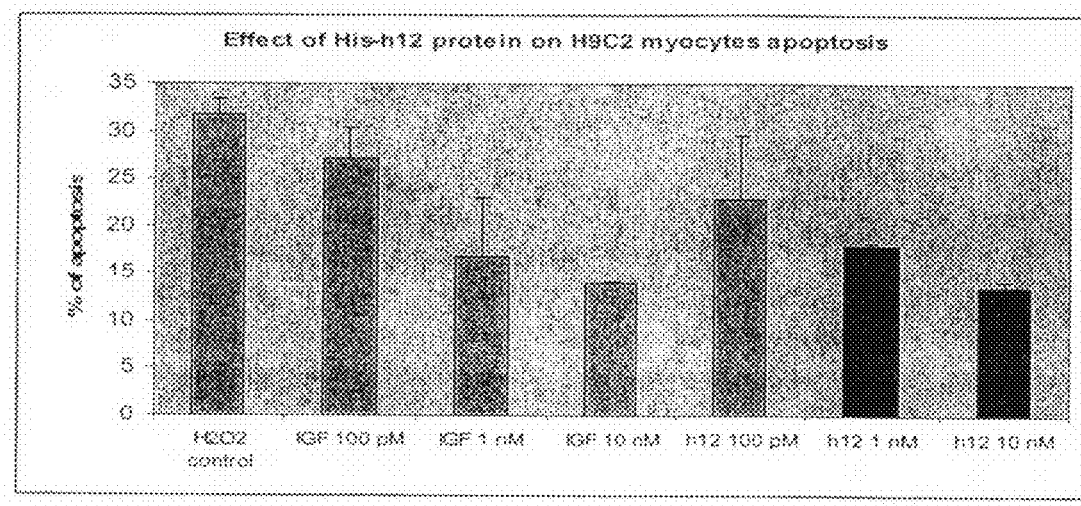
FIG. 7 is a bar graph showing the effect of cytoprotective factor h12 compared to IGF-1 on myocyte apoptosis.

FIG. 7 shows the results of Annexin V/PI staining with FACS analysis in H9C2 myocytes for early apoptosis. H9C2 myocytes were seeded at $1 \times 10^4$ per well in 6-well plate one day before experiment. Recombinant His-h12 proteins were added to the cells at different concentration for 30 min first and then the cells were challenged with 100 µM of $H_2O_2$ for 2 hours to induce apoptosis. The apoptotic cells were calculated as the percentage of Annexin V positive cells in total cells in FACS analysis. Recombinant human IGF-1 proteins were used as a positive control. Pre-incubation of this His-h12 recombinant protein dramatically reduced subsequent $H_2O_2$-induced early apoptosis in H9C2 myocytes, resulting in a ~50% reduction in annexin V positive cells, P<0.001. The effect of Human No. 12 is equivalent to human recombinant IGF-1 protein at the same dose, 10 nM.

Figure 8:
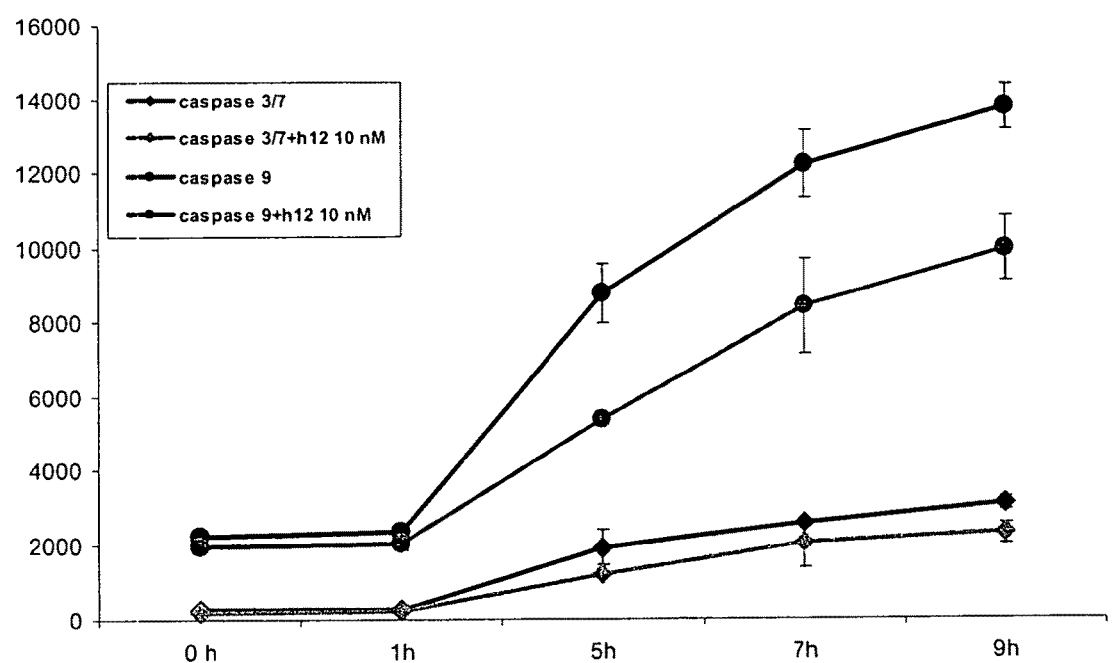
FIG. 8 is a line graph showing caspase inhibition in cardiomyocytes by h12.

An assay was carried out to evaluate caspase inhibition by recombinant His-h12 protein in adult rat cardiomyocytes (FIG. 8). Adult rat cardiomyocytes were pre-incubated with 10 nM of recombinant His-h12 protein for 30 min and then challenged with 100 µM of $H_2O_2$ for different time points. Cell lysates were used for the measurement of relative amount of active caspase with Promega's Caspase-Glo kits. His-h12 protein significantly reduced caspase 9 activity starting from 5 hours onward, reaching highest inhibition (~40% inhibition) at 9 hour, p<0.001. The absolute amount of active Caspase 3/7 is relatively lower than that of Caspase 9 in there cells, however, His-h12 protein also significantly reduced caspase 3/7 activity at 9 hours, p<0.01.

Figure 9:
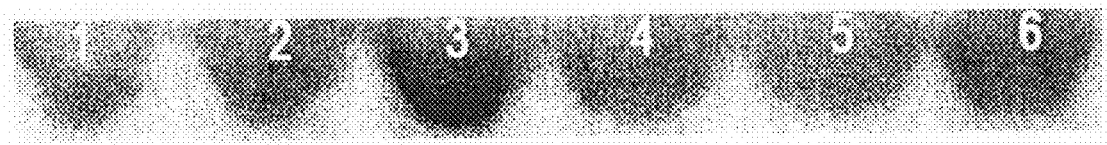
FIG. 9 is a series of photographs electrophoretic gels showing that h12 phosphorylates/activates AKT in cardiomyocytes
Figure 9:
Figure 9:
Figure 9:

Survival signaling mechanism of His-h12 protein on cardiomyocytes was also evaluated. Experiments were carried out to determine whether His-h12 exerts its protective effect for $H_2O_2$-induced apoptosis of cardiomyocytes, in a paracrine fashion mainly through intracellular survival signaling transduction, which positively regulates the whole machinery of apoptosis network. The expression of apoptosis-related genes was studied in rat adult cardiomyocytes after incubation of His-h12 protein at 10 nM at various time points. Adult rat cardiomyocytes were incubated with recombinant His-h12 protein at 10 nM final concentration for 10 min, 30 min, 1 h, 2 h and 3 h. Whole cell lysates were separated on 10% SDS-PAGE gels and probed with phosphor-Akt antibodies, total Akt antibody and GSK-3β antibody (FIG. 9). Lane 1, vehicle PBS control treatment; Lane 2-6, 10 min, 30 min, 1 h, 2 h and 3 h incubation of cardiomyoctyes with His-h12 protein respectively. Compared with lane 1 vehicle PBS control treatment, incubation of His-h12 protein dramatically activates phosphor Akt$^{Thr308}$ at 30 min, with the concurrent phosphorylation of Akt's substrate-GSK-3β, at the same time point. No significant changes were found in total Akt and β-tublin as loading controls.

Figure 10:
FIG. 10 is a photograph showing inhibition of cytochrome C release by h12.

FIG. 10 shows the results of an assay to evaluate cytochrome C release. Adult rat cardiomycytes were pre-incubated with recombinant His-h12 protein at 10 nM for 30 min, then challenged with 100 µM of $H_2O_2$ for 6 h to induce apoptosis. Cytosolic proteins were separated by 15% SDS-PAGE gel and probed with anti-cytochrome C antibodies. Lane 1-2, vehicle PBS control treatment; Lane 3-4, $H_2O_2$ treatment of cardiomyocytes for 6 h; Lane 5-8, cardiomyoctyes pre-incubated with His-h12 protein for 30 min and then challenged with $H_2O_2$ for 6 h. Compared with Lane 1-2 controls, $H_2O_2$ treatment of Lane 3-4 resulted in a dramatic release of cytochrome C into cytosolic compartment of cardiomyocytes. However, pre-incubation of His-h12 protein with cardiomyocytes for 30 min significantly prevented the release of cytochrome C.

Figure 11:
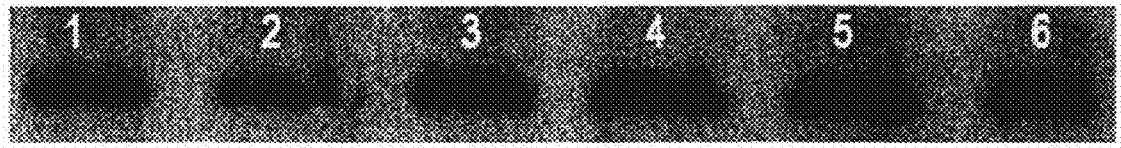
FIG. 11 is a photograph of an electrophoretic gel showing mitochondrial Bcl-2 protein stabilization by h12.

FIG. 11 shows stabilization of mitochondrial Bcl-2 protein level by His-h12 protein during cardiomyocyte apoptosis. Adult rat cardiomycytes were pre-incubated with recombinant His-h12 protein at 10 nM for 30 min, then challenged with 100 µM of $H_2O_2$ for 6 h to induce apoptosis. Mitochondrial proteins were separated by 12.5% SDS-PAGE gel and probe with anti-Bcl-2 antibody. Lane 1, no treatment control; Lane 2, cardiomyocytes challenged with 100 µM of $H_2O_2$ for 6 h; Lane 3-6, cardiomyocytes pre-incubated with 10 nM of His-h12 for 30 min and then challenged with 100 µM of $H_2O_2$ for 6 h. Compared with Lane 1 control, H₂O₂ treatment of Lane 2 resulted in a modest decrease of mitochondrial Bcl-2. Pre-incubation of cardiomyocytes with His-h12 protein stabilized the mitochondrial Bcl-2 protein level.

Sequences and GenBank Accession Number of His-h12

No. 12 has a GenBank designation human BC037293. This gene product is also know as chromosome 3 open reading frame 58 (c3orf58). Mouse No. 12 homologous gene is currently unknown. The cDNA of human No. 12 clone was purchased from ATCC, coding region were amplified to make the expression construct, N-terminal signal deletion coding sequence of human No. 12 were amplified and clone into pMal-C vector for fusion protein expression and purification, which were used in the initial screening studies. Human No. 12 was further expressed as 6×His tagged recombinant protein for cardio-protection studies.

```
Human No. 12 full-length mRNA sequence (h12; SEQ ID NO 16)
   1 gccggagtcg gagggcgggg agctaggagg agggagctcg agagttgtgg agactagtga
  61 ctgggagaag tcgcagcccg ctcaggcccg cgccttcccg ctccccgtct tcctctctca
 121 cacacctact ccgccctccg ccccagcccg cgcgctagct ccttctctcg cccggggttc
 181 ctgccggtag ctctccgggt cttggcgcgg cgggggcgcc ccggggggtgc cctcgccctc
 241 ccgttgcggg cgggcgggcg gtatgtggcg cctggtgccc ccgaagctgg gccgcctgtc
 301 ccgctcgctg aagctggcgg cgctgggcag cctgttggtg ctgatggtgc tgcactcgcc
 361 gtcgctgctc gcctcttggc agcgcaacga actgaccgac cggcgcttcc tgcagctcaa
 421 taagtgcccg gcgtgcttcg gcacgagctg gtgccgccgc ttcctcaacg ggcaggtggt
 481 attcgaggcg tggggccgct tgcgcctgct ggacttcctc aacgtgaaga acgtgtactt
 541 cgcgcagtac ggcgagcccc gcgagggcgg ccgccgccga gtggtgctca agcgcctcgg
 601 ctcgcagcgc gagctggcgc agctcgacca gagcatctgc aagcgggcca ccggccggcc
 661 ccgctgcgac ctgctgcagg ccatgccccg gaccgagttc gcgcgcctca acggcgacgt
 721 gcgtctgctc acgcccgagg cggtggaggg ctggtcggac ctggtgcact gcccctcgca
 781 gcgccttctc gaccgcctgg tgcgccgcta cgcggagacc aaggactcgg gcagcttcct
 841 gcttcgcaac ctcaaggact cggagcgcat gcagctgctg ctgaccctgg ccttcaaccc
 901 cgagccgctg gtgctacaga gttttccgtc tgatgaaggt tggccatttg caaagtatct
 961 tggagcttgt ggaagaatgg tggctgtaaa ttatgttgga gaagaactgt ggagttactt
1021 taatgcgcca tgggaaaaac gagttgacct cgcttggcaa ttaatggaaa tagcagaaca
1081 gcttacaaac aatgactttg aatttgcact ctacctcctg gacgtcagct ttgacaattt
1141 tgcagttggt cctagagatg ggaaggtaat cattgtggat gctgaaaatg ttttggttgc
1201 tgacaaaaga ttaattagac aaaataaacc tgaaaattgg gatgtatggt atgaaagcaa
1261 gtttgatgac tgtgataagg aggcttgctt atcattttca aaagaaattc tttgtgctcg
1321 tgccactgtg gaccacaatt actatgctgt ttgtcagaac ctcttatcca gacatgccac
1381 ctggcgtggc acttctggag gactccttca tgatccacca agtgaaattg ccaaagatgg
1441 ccggctcgag gccttgctgg atgagtgtgc caacccaaag aagcgctatg cagattcca
1501 ggctgcaaaa gaactgcgtg aatacctagc acaattaagt aacaacgtga ggtagtctat
1561 ggtgaacttt tcttttttc tccatttaaa cagcactggc taaaactaaa ccaccaaaaa
1621 acgatctgaa aaaatgaaat tggaagtgt tacattcaga ggatgataaa cttgcactga
1681 tagatcttaa tgttaacatc catcaaaata agacattact tcaaaaatca catgatgctt
1741 ctgcaaataa gtatgttctt atactttgga ggcttgagct gtcatcagct gctccccact
1801 accccggaat gcttgagtgg attaatgaat attgttaagc tattggaaat gagtctgata
1861 gtacattggc ttgtgtatca aagggtactt ggtacttagt ttgcatttac tatcatgatt
1921 ttgtgaatct cttgcatttta ctttgaatgt caagtcagat tggtctgttt tataggccgc
1981 ttttccttc tgatgtgtag ggtttttcc ccctttttt ttttaattaa attttgaaaa
2041 ttcaggttac tgtaggtgtt catttaaatt tttaatagtt gtcattcagt gctatttggt
```

-continued

```
2101 acatatttac tgttagggca ggattcccag gtttactgtg tttttttttt ttttttttta
2161 aagaaagcta aatattacat tatgtaaata cttcttttca ccaacttctg tagtttcacc
2221 attgcatggt gtcatttcag gttatttaac agttatatcc ctctatgcca ataattagaa
2281 gtgtacacta aacatgaagt ttggcatatg ttgcaaaatg tcattttatc tttctaaagg
2341 ctttaagaag aatatactag aatctatata ttgatgttaa ttttgattca gaaaaaaaat
2401 acaacccagt atctaaaaag tgttaactag tccaagatat taatgcatat gccaaagaaa
2461 tattcaccct aatctcatgt ttagaattta aaatagaatt ggtcagctac ttattcttac
2521 caccctactt ccagtatttt agctctgtca ttattaaatt cagatcttcc tgattatttt
2581 ttctgttgaa agttaaacta ctgctttcaa gtaatttaaa gttatcctac cttttattca
2641 tgggtagttt tgcaaaatta acatggtagc cattgtttga atttaatcgg gcatcataac
2701 ttttcattta ttgaggaact aatcattatt actataaagc atacaaatta gccagtcagc
2761 acactttggt cttctttacc taagggtaa acatcagaac atcaaattta attatttgca
2821 tagaaatgtg tgggctcttt atataagttg actatcacta caggtaata ttttctgtt
2881 tgaagttgtt acttttgttt acagcaaagt ttgatgtagt gtgcagtagt gagctctaga
2941 ctgatctttt tctaaatcag aaagtgatta aagtatgcac aaccaaaggc aggttttttct
3001 ttttcattta ttcagcaact atttattaag catcaactct gtgccaggca cgttactagc
3061 tgctacatac tgtctgaaca tgacatacgg ttaagtaact ttacaattat tatcaaatac
3121 ttcaatgtag atatttctta agttgaaata gcattaacta ggataatgct ttcatgttat
3181 tttattgtct tgtgatagaa attcaacttg taccatctaa aactaggttg ctataaaaat
3241 aggaggatga agtcaataaa gtttatgcca gtttaaaaac tggaaggaaa aggtaagagc
3301 tctccattat aaaatagttg cattcggtta atttttacac attagtgcat tgcgtatatc
3361 aactggccct caatgaagca tttaagtgct tggaattta ctaaactgac ttttttgcaa
3421 ctttgggaga ttttgaggg gagtgttgaa aattgccaaa cactcacctc ttactcaaaa
3481 cttcaaataa aatacacatt ttcaagaggg agcaccttt atatttgata agttttcatt
3541 ataaacctta taataccagt cacaaagagg ttgtctgtct atggtttagc aaacatttgc
3601 ttttctttt ggaagtgtga ttgcaattgc agaacagaaa gtgagaaaac actgccagcg
3661 gtgattgcta cttgaggtag ttttttacaa ctaccatttc ccctccatga aattatgtga
3721 aatttatttt atctttggga aaagttgaga agatagtaaa agaattagga atttaaaatt
3781 acagggaaaa atatgtaagt gaaaagcaat aaatattttg ttcactttgc tatcaagatg
3841 ttcactatca gatatttatt atatggcagc aattatatt tttaatcatt gcccattaat
3901 agacgcagta aaatatttt gaatcagaca tttggggttt gtatgtgcat taaaattgtc
3961 ttttgtactg taagttactg ttaatttgaa tattttattg aactgtctcc ctgtgccttt
4021 ataatataaa gttgtttcta caacttttaa tgatcttaat aaagaatact ttaggaaaaa
4081 aaaaaaaaa a
```

Human No. 12 protein sequence (sequence in underlined type was used to generate recombinant His-h12 protein) (h12; SEQ ID NO: 17)
MWRLVPPKLGRLSRSLKLAALGSLLVLMVLHSPSLLASWQRNEL<u>TDRRFLQLNKCPACFGTSWCRRFL
NGQVVFEAWGRLRLLDFLNVKNVYFAQYGEPREGGRRRVVLKRLGSQRELAQLDQSICKRATGRPRCD
LLQAMPRTEFARLNGDVRLLTPEAVEGWSDLVHCPSQRLLDRLVRRYAETKDSGSFLLRNLKDSERMQ
LLLTLAFNPEPLVLQSFPSDEGWPFAKYLGACGRMVAVNYVGEELWSYFNAPWEKRVDLAWQLMEIAE</u>

-continued

QLTNNDFEFALYLLDVSFDNFAVGPRDGKVIIVDAENVLVADKRLIRQNKPENWDVWYESKFDDCDKE

ACLSFSKEILCARATVDHNYYAVCQNLLSRHATWRGTSGGLLHDPPSEIAKDGRLEALLDECANPKKR

YGRFQAAKELREYLAQLSNNVR

Other genes and gene products, the function and activity of which have previously not been known, have now been identified as having cardioprotective activity. The nucleic acid and amino acid sequences of these factors are described below.

```
Human No. 1 mRNA sequence (h1: SEQ ID NO: 18)
   1 gcatcttggc agggtccggg gacgtggact atttcgcaca ccacaccacg gggagggatt
  61 ttttctatt ttccctacga aaacagatc tttttaagga tggtgctgct ccactggtgc
 121 ctgctgtggc tcctgtttcc actcagctca aggacacaga agttacccac ccgggatgag
 181 gaacttttc agatgcagat ccgggacaag gcattttttc atgattcgtc agtaattcca
 241 gatggagctg aaattagcag ttatctcttt agagatacac ctaaaaggta tttctttgtg
 301 gttgaagaag acaatactcc attatcagtc acagtgacgc cctgtgatgc gcctttggag
 361 tggaagctga gcctccagga gctgccagag gacaggagcg gggaaggctc aggtgatctg
 421 gaacctcttg agcagcagaa gcagcagatc attaatgagg aaggcactga gttattctcc
 481 tacaaaggca atgatgttga gtattttata tcgtctagtt ccccatccgg tttgtatcag
 541 ttggatcttc tttcaacaga gaaagacaca catttcaaag tatatgccac cacaactcca
 601 gaatctgatc agccataccc tgagttaccc tatgacccaa gagtagatgt gacctcactg
 661 gggcgcacca cggtcacttt ggcctggaaa ccaagcccca ctgcctcttt gctgaaacaa
 721 cccattcagt actgtgtggt catcaacaaa gagcacaatt tcaaaagtct ctgtgcagtg
 781 gaagcaaaac tgagtgcaga tgatgctttt atgatggcac cgaaacctgg tctggacttc
 841 agccccttg actttgccca ctttggattt ccttctgata attcaggtaa agaacgcagt
 901 ttccaggcaa agccttctcc aaaactgggg cgtcatgtct actccaggcc caaggttgat
 961 attcagaaaa tctgcatagg aaacaagaac atcttcaccg tctctgatct gaaacccgac
1021 acgcagtact actttgatgt atttgtggtc aacatcaaca gcaacatgag caccgcttat
1081 gtaggtacct tgccaggac caaggaagaa gccaaacaga agacagtcga gctaaaagat
1141 gggaagataa cagatgtatt tgttaaaagg aagggagcaa agtttctacg gtttgctcca
1201 gtctcttctc accaaaaagt caccttcttt attcactctt gtctggatgc tgtccaaatc
1261 caagtgagaa gagatgggaa acttcttctg tctcagaatg tggaaggcat tcagcagttt
1321 cagcttagag gaaaacctaa agctaaatac ctcgttcgac tgaaaggaaa caagaaagga
1381 gcatctatgt tgaaaattct agctaccaca aggcctacta agcagtcatt tccctctctt
1441 cctgaagaca caagaatcaa agcctttgac aagctccgta cctgttcctc ggccaccgtg
1501 gcttggctag cactcaggaa aggaacaag ttttgcatct acaaaaaaga agtggatgat
1561 aactacaatg aagaccagaa gaaaagagag caaaaccaat gtctaggacc agatataagg
1621 aagaagtcag aaaaggtcct ctgtaaatat ttccacagtc aaaacttgca gaaagcagtg
1681 accacagaaa caattaaagg tcttcagcct ggcaaatctt acctgctgga tgtttatgtc
1741 ataggacatg gggggcactc tgtaaagtat cagagtaagg ttgtgaaaac tagaaagttc
1801 tgttagttac cttcttatag agatatatta tgtagaactc caggagggac attaaatcac
1861 tttaagtata aactgactac tcccacagtt gagagaagtt gtgacctgta cttgtactat
1921 ggaaggaagg atatcaacgt gtgtatattg atgtttatat aagtaactct tgaaggagac
1981 ttgttctagc gtgccccatg gtacctagtg tgtgtctgat gccggttggt gtcaaagata
```

-continued

```
2041 gagggcttct tgaaggaact tgccattcct tgctttgacc actgcatgaa ctgcttctaa 2101 attattttat tacctaaaaa tttaaaatat gccattcatt gcacacaccc acaaatgcaa 2161 atcattcctc tctatagatg ctaggatata tataaattat tttataaatt cttgttttaa 2221 atgtcagtgt ttctatgatt gtaaactatt aaattctttt cctattaaag tacagatcta 2281 atctaagtat tattaagttg atagccctct agtcagttat attgctattg taaattcttg 2341 tttgttgagt aaaatgttta aatactatat gtatctcatg tacaaagttg acatacatta 2401 tattcatgta cataaaatta aagagattag attataa
```

Human No. 1 protein sequence (h1: SEQ ID NO: 19)
MVLLHWCLLWLLFPLSSRTQKLPTRDEELFQMQIRDKAFFHDSSVIPDGAEISSYLFRDTPKRYFFVVE
EDNTPLSVTVTPCDAPLEWKLSLQELPEDRSGEGSGDLEPLEQQKQQIINEEGTELFSYKGNDVEYFIS
SSSPSGLYQLDLLSTEKDTHFKVYATTTPESDQPYPELPYDPRVDVTSLGRTTVTLAWKPSPTASLLKQ
PIQYCVVINKEHNFKSLCAVEAKLSADDAFMMAPKPGLDFSPFDFAHFGFPSDNSGKERSFQAKPSPKL
GRHVYSRPKVDIQKICIGNKNIFTVSDLKPDTQYYFDVFVVNINSNMSTAYVGTFARTKEEAKQKTVEL
KDGKITDVFVKRKGAKFLRFAPVSSHQKVTFFIHSCLDAVQIQVRRDGKLLLSQNVEGIQQFQLRGKPK
AKYLVRLKGNKKGASMLKILATTRPTKQSFPSLPEDTRIKAFDKLRTCSSATVAWLGTQERNKFCIYKK
EVDDNYNEDQKKREQNQCLGPDIRKKSEKVLCKYFHSQNLQKAVTTETIKGLQPGKSYLLDVYVIGHGG
HSVKYQSKVVKTRKFC Human No. 5 mRNA sequence (h5; SEQ ID NO: 20

```
  1 agcgggatag cccgcggccg cgcctgcccg ctcgcacccc tctcccgcgc ccggttctcc 61 ctcgcagcac ctcgaagtgc gcccctcgcc ctcctgctcg cgcccgccg ccatggctgc 121 ctccccgcg cggcctgctg tcctggccct gaccgggctg gcgctgctcc tgctcctgtg 181 ctggggccca ggtggcataa gtggaaataa actcaagctg atgcttcaaa aacgagaagc 241 acctgttcca actaagacta aagtggccgt tgatgagaat aaagccaaag aattccttgg 301 cagcctgaag cgccagaagc ggcagctgtg ggaccggact cggcccgagg tgcagcagtg 361 gtaccagcag tttctctaca tgggctttga cgaagcgaaa tttgaagatg acatcaccta 421 ttggcttaac agagatcgaa atggacatga atactatggc gattactacc aacgtcacta 481 tgatgaagac tctgcaattg gtccccggag cccctacggc tttaggcatg gagccagcgt 541 caactacgat gactactaac catgacttgc cacacgctgt acaagaagca aatagcgatt 601 ctcttcatgt atctcctaat gccttacact acttggtttc tgatttgctc tatttcagca 661 gatcttttct acctactttg tgtgatcaaa aagaagagt taaaacaaca catgtaaatg 721 ccttttgata tttcatggga atgcctctca tttaaaaata gaaataaagc attttgttaa 781 aaagaaaaaa aaaaaaaaaa
```

Human No. 5 protein sequence (h5; SEQ ID NO: 21)
MAASPARPAVLALTGLALLLLLCWGPGGISGNKLKLMLQKREAPVPTKTKVAVDENKAKEFLGSLKRQK
RQLWDRTRPEVQQWYQQFLYMGFDEAKFEDDITYWLNRDRNGHEYYGDYYQRHYDEDSAIGPRSPYGFR
HGASVNYDDY Human No. 8 mRNA sequence (h8; SEQ ID NO: 22)

```
  1 cactgggaga cagtccactt aaatgcagct ccagggttgc gaggcaccca ccagcatcat 61 tccccatgcg aggtggcaaa tgcaacatgc tctccagttt ggggtgtcta cttctctgtg 121 gaagtattac actagccctg ggaaatgcac agaaattgcc aaaaggtaaa aggccaaacc 181 tcaaagtcca catcaatacc acaagtgact ccatcctctt gaagttcttg cgtccaagtc 241 caaatgtaaa gcttgaaggt cttctcctgg gatatggcag caatgtatca ccaaaccagt 301 acttccctct tcccgctgaa gggaaattca cagaagctat agttgatgca gagccgaaat
```

-continued

```
 361 atctgatagt tgtgcgacct gctccacctc caagtcaaaa gaagtcatgt tcaggtaaaa
 421 ctcgttctcg caaacctctg cagctggtgg ttggcactct gacaccgagc tcagtcttcc
 481 tgtcctgggg tttcctcatc aacccacacc atgactggac attgccaagt cactgtccca
 541 atgacagatt ttatacaatt cgctatcgag aaaaggataa agaaaagaag tggattttc
 601 aaatctgtcc agccactgaa acaattgtgg aaaacctaaa gcccaacaca gtttatgaat
 661 ttggagtgaa agacaatgtg gaaggtggaa tttggagtaa gattttcaat cacaagactg
 721 ttgttggaag taaaaaagta aatgggaaaa tccaaagtac ctatgaccaa gaccacacag
 781 tgccagcata tgtcccaagg aaactaatcc caataacaat catcaagcaa gtgattcaga
 841 atgttactca caaggattca gctaaatccc cagaaaaagc tccactggga ggagtgatac
 901 tagtccacct tattattcca ggtcttaatg aaactactgt aaaacttcct gcatccctaa
 961 tgtttgagat ttcagatgca ctcaagacac aattagctaa gaatgaaacc ttggcattac
1021 ctgccgaatc taaaacacca gaggttgaaa aaatctcagc acgacccaca acagtgactc
1081 ctgaaacagt tccaagaagc actaaaccca ctacgtctag tgcattagat gtttcagaaa
1141 caacactggc ttcaagtgaa aagccatgga ttgtgcctac agctaaaata tctgaagatt
1201 ccaaagttct gcagcctcaa actgcaactt atgatgtttt ctcaagccct acaacatcag
1261 atgagcctga gatatcagat tcctacacag caacaagtga tcgtattctg gattctatcc
1321 cacctaaaac ttctagaact cttgaacagc caagggcaac actggctcca agtgaaacac
1381 catttgttcc tcaaaaactg gaaatcttta ccagtccaga aatgcagcct acgacacctg
1441 ctccccagca aactacatct atcccttcta cacctaaacg acgccccgg cccaaaccgc
1501 caagaaccaa acctgaaaga accacaagtg ccggaacaat tacacctaaa atttctaaaa
1561 gccctgaacc tacatggaca acaccggctc ccggtaaaac acaatttatt tctctgaaac
1621 ctaaaatccc tctcagccca gaagtgacac acaccaaacc tgctcccaag cagacaccac
1681 gtgctcctcc taagccaaaa acatcaccac gcccaagaat cccacaaaca caaccagttc
1741 ctaaggtgcc ccagcgtgtt actgcaaaac caaaaacgtc accaagtcca gaagtgtcat
1801 acaccacacc tgctccaaaa gatgtgctcc ttcctcataa accatacct gaggtctctc
1861 agagcgaacc tgctcctcta gagacacgag gcatccctt tatacccatg atttccccaa
1921 gtcctagtca agaggaacta cagaccactc tggaagaaac agaccaatcc acccaagaac
1981 ctttcacaac taagattcca cgaacaactg aactagcaaa gacaactcag gcgccacaca
2041 gattttatac tactgtgagg cccagaacat ctgacaagcc acacatcaga cctgggtca
2101 agcaagcacc caggccatca ggtgctgata gaaatgtatc agtggactct acccaccca
2161 ctaaaaagcc agggactcgc cgcccacct tgccacccag acctacacac ccacgaagaa
2221 aacctttacc accaaataat gtcactggaa agccaggaag tgcaggaatc atttcatcag
2281 gcccaataac tacaccaccc ctgaggtcaa cacccaggcc tactggaact cccttggaga
2341 gaatagagac agatataaag caaccaacag ttcctgcctc tggagaagaa ctggaaaata
2401 taactgactt tagctcaagc ccaacaagag aaactgatcc tcttgggaag ccaagattca
2461 aaggacctca tgtgcgatac atccaaaagc ctgacaacag tccctgctcc attactgact
2521 ctgtcaaacg gttccccaaa gaggaggcca cagaggggaa tgccaccagc ccaccacaga
2581 acccacccac caacctcact gtggtcaccg tggaagggtg cccctcattt gtcatcttgg
2641 actgggaaaa gccactaaat gacactgtca ctgaatatga agttatatcc agagaaaatg
2701 ggtcattcag tgggaagaac aagtccattc aaatgacaaa tcagacattt tccacagtag
```

-continued

```
2761 aaaatctgaa accaaacacg agttatgaat tccaggtgaa acccaaaaac ccgcttggtg
2821 aaggcccggt cagcaacaca gtggcattca gtactgaatc agcggaccca agagtgagtg
2881 agccagtttc tgcaggaaga gatgccatct ggactgaaag acccttaat tcagactctt
2941 actcagagtg taagggcaaa caatatgtca aaggacatg gtataaaaaa tttgtaggag
3001 tgcagctgtg caactctctc agatacaaga tttacttgag cgactccctc acaggaaaat
3061 tttataacat aggtgatcag aggggccatg gagaagatca ctgccagttt gtggattcat
3121 ttttagatgg acgcactggg cagcaactca cttctgacca gttaccaatc aaagaaggtt
3181 atttcagagc agttcgccag gaacctgtcc aatttggaga ataggtggt cacacccaaa
3241 tcaattatgt tcagtggtat gaatgtggga ctacaattcc tggaaaatgg tagatgctgc
3301 acaaagttac cttctgtttc atcattgcaa acaaaaatca ttgaaaatac tatgccgcat
3361 tcatttaaag ctatttttgt tactatgtat aaaagtctac aatctaatta atagcaatac
3421 tagatgttta ttattagaaa agattgctga gagtatttat caggttttac aaagtcattt
3481 taagaaagca agatactgat gttaacagaa taacattttt ggggaagctg gctccctatt
3541 catggtattt taagagatca tttgtatatt atttatcaca ctgttgtaat gatgttttga
3601 gatacttta taacaaaatt aacatcaaaa aggtatatac ttttaaaaa aaatttactt
3661 ttattgatgt gtactcttcc tattgatgag ttaattccat aaatctctac ttagtttaac
3721 ttattggatc aaattatctt cagcatgtat atctggggaa aaaaggtccg aatttttcaca
3781 tttatattta aacttcaatt tttatattt aaacttcaat tttttagcaa cagctgaata
3841 gctttgcgga ggagtttaat agttacacat tcatgctaat atacatttcc tttaaacatc
3901 cacaaattct taaaaagatt gaatcagtaa atttcatttc agctaaaat ggagtctaat
3961 atattgtttc aaaagataca ttttacccca ccataaatgt tacaatatct gaatatgctt
4021 tgtcaaacta cccttatg caatcgtctt catattgttt ttatgattct aatcaagctg
4081 tatgtagaga ctgaatgtga agtcaagtct gagcacaaaa agataatgca caatgagatt
4141 gcctaccatt ttataggata tttactatgt atttatacgt taagacctct atgaatgaat
4201 gtatcagaga atgtctttgt aactaactgt ttaattcaat ctgtaataaa atctaacta
4261 actaactcat ttatttctat taaaaaggta ttgtccttta ggcggggaat gggaatcctt
4321 gctgcactgt tgcagtcatt ctgaaaggac ctttccctgt acttacctt caacatgctt
4381 caatcttatc aacgctacat tttgtatttt tcaaacaggt ataaattctg caataaagag
4441 atgtagtttt ttttaaaaa aaaaaaaaaa aaaaaaaaa aaaaaaaaa aaaaaaaaa
4501 aaaaaaaaaa aaaaaaaaa aaaaaaaaa aaa
```

Human No. 8 protein sequence (h8; SEQ ID NO: 23)

MRGGKCNMLSSLGCLLLCGSITLALGNAQKLPKGKRPNLKVHINTTSDSILLKFLRPSPNVKLEGLLLG
YGSNVSPNQYFPLPAEGKFTEAIVDAEPKYLIVVRPAPPPSQKKSCSGKTRSRKPLQLVVGTLTPSSVF
LSWGFLINPHHDWTLPSHCPNDRFYTIRYREKDKEKKWIFQICPATETIVENLKPNTVYEFGVKDNVEG
GIWSKIFNHKTVVGSKKVNGKIQSTYDQDHTVPAYVPRKLIPITIIKQVIQNVTHKDSAKSPEKAPLGG
VILVHLIIPGLNETTVKLPASLMFEISDALKTQLAKNETLALPAESKTPEVEKISARPTTVTPETVPRS
TKPTTSSALDVSETTLASSEKPWIVPTAKISEDSKVLQPQTATYDVFSSPTTSDEPEISDSYTATSDRI
LDSIPPKTSRTLEQPRATLAPSETPFVPQKLEIFTSPEMQPTTPAPQQTTSIPSTPKRRPRPKPPRTKP
ERTTSAGTITPKISKSPEPTWTTPAPGKTQFISLKPKIPLSPEVTHTKPAPKQTPRAPPKPKTSPRPRI
PQTQPVPKVPQRVTAKPKTSPSPEVSYTTPAPKDVLLPHKPYPEVSQSEPAPLETRGIPFIPMISPSPS
QEELQTTLEETDQSTQEPFTTKIPRTTELAKTTQAPHRFYTTVRPRTSDKPHIRPGVKQAPRPSGADRN

VSVDSTHPTKKPGTRRPPLPPRPTHPRRKPLPPNNVTGKPGSAGIISSGPITTPPLRSTPRPTGTPLER

IETDIKQPTVPASGEELENITDFSSSPTRETDPLGKPRFKGPHVRYIQKPDNSPCSITDSVKRFPKEEA

TEGNATSPPQNPPTNLTVVTVEGCPSFVILDWEKPLNDTVTEYEVISRENGSFSGKNKSIQMTNQTFST

VENLKPNTSYEFQVKPKNPLGEGPVSNTVAFSTESADPRVSEPVSAGRDAIWTERPFNSDSYSECKGKQ

YVKRTWYKKFVGVQLCNSLRYKIYLSDSLTGKFYNIGDQRGHGEDHCQFVDSFLDGRTGQQLTSDQLPI

KEGYFRAVRQEPVQFGEIGGHTQINYVQWYECGTTIPGKW

Human No. 13 mRNA sequence (h13; SEQ ID NO: 24)

```
  1 ctccggtgag ttttgtggcg ggaagcttct gcgctggtgc ttagtaaccg actttcctcc
 61 ggactcctgc acgacctgct cctacagccg gcgatccact cccggctgtt ccccggagg
121 gtccagaggc ctttcagaag gagaaggcag ctctgtttct ctgcagagga gtagggtcct
181 ttcagccatg aagcatgtgt tgaacctcta cctgttaggt gtggtactga ccctactctc
241 catcttcgtt agagtgatgg agtccctaga gggcttacta gagagcccat cgcctgggac
301 ctcctggacc accagaagcc aactagccaa cacagagccc accaagggcc ttccagacca
361 tccatccaga agcatgtgat aagacctcct tccatactgg ccatattttg gaacactgac
421 ctagacatgt ccagatggga gtcccattcc tagcagacaa gctgagcacc gttgtaacca
481 gagaactatt actaggcctt gaagaacctg tctaactgga tgctcattgc ctgggcaagg
541 cctgtttagg ccggttgcgg tggctcatgc ctgtaatcct agcactttgg gaggctgagg
601 tgggtggatc acctgaggtc aggagttcga gaccagcctc gccaacatgg cgaaacccca
661 tctctactaa aaatacaaaa gttagctggg tgtggtggca gaggcctgta atcccagctc
721 cttgggaggc tgaggcggga gaattgcttg aacccgggga cggaggttgc agtgagccga
781 gatcgcactg ctgtacccag cctgggccac agtgcaagac tccatctcaa aaaaaaaaaa
841 aaaaaaaaaa aaaaaaaaa
```

Human No. 13 protein sequence (h13; SEQ ID NO: 25)
MKHVLNLYLLGVVLTLLSIFVRVMESLEGLLESPSPGTSWTTRSQLANTEPTKGLPDHPSRSM

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein.

Other aspects, advantages, and modifications considered to be within the scope of the following claims.

What is claimed is:

1. A method of reducing cell death, comprising contacting an injured or diseased cardiac tissue with a composition comprising a full-length or mature Secreted frizzled related protein-2 (Sfrp2) or Wnt3a-binding fragment thereof and wherein cell death is reduced in the presence of said composition compared to in its absence.

2. The method of claim 1, wherein said composition further comprises Secreted frizzled related protein 1 (Sfrp1) or Secreted frizzled related protein 3 (Sfrp3), wherein said Sfrp1 comprises the amino acid sequence of SEQ ID NO:5 or the mature processed amino acid sequence of SEQ ID NO:5 and wherein said Sfrp3 comprises the amino acid sequence of SEQ ID NO:9 or the mature processed amino acid sequence of SEQ ID NO:9.

3. The method of claim 1, wherein said full-length Sfrp2 comprises the amino acid sequence of SEQ ID NO:7 and said mature Sfrp2 comprises the mature processed-amino acid sequence of SEQ ID NO:7.

4. The method of claim 1, wherein said Sfrp2 reduces apoptotic cell death.

* * * * *

UNITED STATES PATENT AND TRADEMARK OFFICE
CERTIFICATE OF CORRECTION

PATENT NO.         : 8,129,344 B2                                               Page 1 of 1
APPLICATION NO.    : 12/008583
DATED              : March 6, 2012
INVENTOR(S)        : Dzau et al.

It is certified that error appears in the above-identified patent and that said Letters Patent is hereby corrected as shown below:

On the Title page of the patent, insert the following section:

--Related U.S. Application Data
    Divisional of patent application U.S.S.N. 11/508,010, filed August 21, 2006, now U.S. Pat. No. 7,638,128.
    Provisional application No. 60/710,028, filed August 19, 2005, provisional application No. 60/711,287, filed on August 25, 2005.--

Column 1, lines 13-17, replace the text with:

This application is a divisional of patent application U.S.S.N. 11/508,010, filed August 21, 2006, now U.S. Pat. No. 7,638,128, which claims priority from U.S.S.N. 60/710,028, filed August 19, 2005, and provisional application No. 60/711,287, filed on August 25, 2005, all of which, with the exception of U.S.S.N. 11/508,010, is incorporated by reference.

Signed and Sealed this
Tenth Day of July, 2012

David J. Kappos
*Director of the United States Patent and Trademark Office*

SEQUENCE LISTING

```
<160> NUMBER OF SEQ ID NOS: 25

<210> SEQ ID NO 1
<211> LENGTH: 2610
<212> TYPE: DNA
<213> ORGANISM: Homo sapiens

<400> SEQUENCE: 1
atcctgggac agggcacagg gccatctgtc accaggggct tagggaaggc cgagccagcc      60
tgggtcaaag aagtcaaagg ggctgcctgg aggaggcagc ctgtcagctg gtgcatcaga     120
ggctgtggcc aggccagctg ggctcgggga gcgccagcct gagaggagcg cgtgagcgtc     180
gcgggagcct cgggcaccat gagcgacgtg gctattgtga aggaggggttg gctgcacaaa     240 cgaggggagt acatcaagac ctggcggcca cgctacttcc tcctcaagaa tgatggcacc     300
```

```
ttcattggct acaaggagcg gccgcaggat gtggaccaac gtgaggctcc cctcaacaac    360
ttctctgtgg cgcagtgcca gctgatgaag acggagcggc cccggcccaa caccttcatc    420
atccgctgcc tgcagtggac cactgtcatc gaacgcacct tccatgtgga gactcctgag    480
gagcgggagg agtggacaac cgccatccag actgtggctg acggcctcaa gaagcaggag    540
gaggaggaga tggacttccg gtcgggctca cccagtgaca actcaggggc tgaagagatg    600
gaggtgtccc tggccaagcc caagcaccgc gtgaccatga acgagtttga gtacctgaag    660
ctgctgggca agggcacttt cggcaaggtg atcctggtga aggagaaggc cacaggccgc    720
tactacgcca tgaagatcct caagaaggaa gtcatcgtgg ccaaggacga ggtggcccac    780
acactcaccg agaaccgcgt cctgcagaac tccaggcacc ccttcctcac agccctgaag    840
tactcttccc agacccacga ccgcctctgc tttgtcatgg agtacgccaa cggggggcgag    900 ctgttcttcc acctgtcccg ggaacgtgtg ttctccgagg accgggcccg cttctatggc    960
gctgagattg tgtcagccct ggactacctg cactcggaga gaacgtggt gtaccgggac   1020 ctcaagctgg agaacctcat gctggacaag gacgggcaca ttaagatcac agacttcggg   1080
ctgtgcaagg aggggatcaa ggacggtgcc accatgaaga cctttgcgg cacacctgag   1140 tacctggccc ccgaggtgct ggaggacaat gactacggcc gtgcagtgga ctggtggggg   1200
ctgggcgtgt tcatgtacga gatgatgtgc ggtcgcctgc ccttctacaa ccaggaccat   1260
gagaagcttt ttgagctcat cctcatggag gagatccgct tcccgcgcac gcttggtccc   1320
gaggccaagt ccttgctttc agggctgctc aagaaggacc ccaagcagag gcttggcggg   1380
ggctccgagg acgccaagga gatcatgcag catcgcttct tgccggtat cgtgtggcag   1440 cacgtgtacg agaagaagct cagcccaccc ttcaagcccc aggtcacgtc ggagactgac   1500
accaggtatt ttgatgagga gttcacggcc cagatgatca ccatcacacc acctgaccaa   1560
gatgacagca tggagtgtgt ggacagcgag cgcaggcccc acttccccca gttctcctac   1620
tcggccagca gcacggcctg aggcggcggt ggactgcgct ggacgatagc ttggagggat   1680
ggagaggcgg cctcgtgcca tgatctgtat ttaatggttt ttatttctcg ggtgcatttg   1740
agagaagcca cgctgtcctc tcgagcccag atggaaagac gttttttgtgc tgtgggcagc   1800 accctccccc gcagcggggt agggaagaaa actatcctgc gggttttaat ttatttcatc   1860
cagtttgttc tccgggtgtg gcctcagccc tcagaacaat ccgattcacg tagggaaatg   1920
ttaaggactt ctacagctat gcgcaatgtg gcattggggg gccgggcagg tcctgcccat   1980
gtgtcccctc actctgtcag ccagccgccc tgggctgtct gtcaccagct atctgtcatc   2040
tctctggggc cctgggcctc agttcaacct ggtggcacca gatgcaacct cactatggta   2100
tgctggccag caccctctcc tgggggtggc aggcacacag cagcccccca gcactaaggc   2160
cgtgtctctg aggacgtcat cggaggctgg gcccctggga tgggaccagg gatgggggat   2220
gggccagggt ttacccagtg ggacagagga gcaaggttta aatttgttat tgtgtattat   2280
gttgttcaaa tgcatttttgg gggttttaa tctttgtgac aggaaagccc tccccttcc   2340 ccttctgtgt cacagttctt ggtgactgtc ccaccggagc ctcccccctca gatgatctct   2400 ccacggtagc acttgacctt ttcgacgctt aacctttccg ctgtcgcccc aggccctccc   2460
tgactccctg tggggggtggc catccctggg cccctccacg cctcctggcc agacgctgcc   2520
gctgccgctg caccacggcg ttttttttaca acattcaact ttagtatttt tactattata   2580
atataatatg gaaccttccc tccaaattct                                     2610
```

```
<210> SEQ ID NO 2
<211> LENGTH: 1715
<212> TYPE: DNA
<213> ORGANISM: Homo sapiens

<400> SEQUENCE: 2
gaattccagc ggcggcgccg ttgccgctgc cgggaaacac aaggaaaggg aaccagcgca      60
gcgtggcgat gggcggggt agagccccgc cggagaggct gggcggctgc cggtgacaga     120
ctgtgccctg tccacggtgc ctcctgcatg tcctgctgcc ctgagctgtc ccgagctagg    180
tgacagcgta ccacgctgcc accatgaatg aggtgtctgt catcaaagaa ggctggctcc    240
acaagcgtgg tgaatacatc aagacctgga ggccacggta cttcctgctg aagagcgacg    300
gctccttcat tgggtacaag gagaggcccg aggcccctga tcagactcta ccccccttaa    360
acaacttctc cgtagcagaa tgccagctga tgaagaccga gaggccgcga cccaacacct    420
ttgtcatacg ctgcctgcag tggaccacag tcatcgagag gaccttccac gtggattctc    480
cagacgagag ggaggagtgg atgcgggcca tccagatggt cgccaacagc ctcaagcagc    540
gggccccagg cgaggacccc atggactaca gtgtggctc ccccagtgac tcctccacga    600
ctgaggagat ggaagtggcg gtcagcaagg cacgggctaa agtgaccatg aatgacttcg    660
actatctcaa actccttggc aagggaacct ttggcaaagt catcctggtg cgggagaagg    720
ccactggccg ctactacgcc atgaagatcc tgcgaaagga agtcatcatt gccaaggatg    780
aagtcgctca cacagtcacc gagagccggg tcctccagaa caccaggcac ccgttcctca    840
ctgcgctgaa gtatgccttc cagacccacg accgcctgtg ctttgtgatg gagtatgcca    900
acgggggtga gctgttcttc cacctgtccc gggagcgtgt cttcacagag gagcgggccc    960
ggttttatgg tgcagagatt gtctcggctc ttgagtactt gcactcgcgg gacgtggtat   1020
accgcgacat caagctggaa aacctcatgc tggacaaaga tggccacatc aagatcactg   1080
actttggcct ctgcaaagag ggcatcagtg acggggccac catgaaaacc ttctgtggga   1140
ccccggagta cctggcgcct gaggtgctgg aggacaatga ctatggccgg ccgtggact   1200 ggtggggct gggtgtggtc atgtacgaga tgatgtgcgg ccgcctgccc ttctacaacc   1260
aggaccacga gcgcctcttc gagctcatcc tcatggaaga gatccgcttc ccgcgcacgc   1320
tcagccccga ggccaagtcc ctgcttgctg ggctgcttaa gaaggacccc aagcagaggc   1380
ttggtggggg gcccagcgat gccaaggagg tcatggagca caggttcttc ctcagcatca   1440
actggcagga cgtggtccag aagaagctcc tgccaccctt caaacctcag gtcacgtccg   1500
aggtcgacac aaggtacttc gatgatgaat ttaccgccca gtccatcaca atcacacccc   1560
ctgaccgcta tgacacctg gcttactgga gctggacca gcggacccac ttccccagt   1620 tctcctactc ggccagcatc cgcgagtgag cagtctgccc acgcagagga cgcacgctcg   1680
ctgccatcac cgctgggtgg tttttacc ctgcc                                 1715

<210> SEQ ID NO 3
<211> LENGTH: 1547
<212> TYPE: DNA
<213> ORGANISM: Homo sapiens

<400> SEQUENCE: 3
gggagtcatc atgagcgatg ttaccattgt gaaagaaggt tgggttcaga agaggggaga      60
atatataaaa aactggaggc caagatactt ccttttgaag acagatggct cattcatagg     120
atataaagag aaacctcaag atgtggattt accttatccc ctcaacaact ttcagtggc    180 aaaatgccag ttaatgaaaa cagaacgacc aaagccaaac acatttataa tcagatgtct    240
```

```
ccagtggact actgttatag agagaacatt tcatgtagat actccagagg aaagggaaga      300
atggacagaa gctatccagg ctgtagcaga cagactgcag aggcaagaag aggagagaat      360
gaattgtagt ccaacttcac aaattgataa tataggagag gaagagatgg atgcctctac      420
aacccatcat aaaagaaaga caatgaatga ttttgactat ttgaaactac taggtaaagg      480
cactttrggg aaagttattt tggttcgaga aaggcaagt ggaaaatact atgctatgaa       540
gattctgaag aaagaagtca ttattgcaaa ggatgaagtg gcacacactc taactgaaag      600
cagagtatta aagaacacta gacatcccctt tttaacatcc ttgaaatatt ccttccagac     660
aaaagaccgt ttgtgtttttg tgatggaata tgttaatggg ggcgagctgt ttttccattt     720
gtcgagagag cgggtgttct ctgaggaccg cacacgtttc tatggtgcag aaattgtctc      780
tgccttggac tatctacatt ccggaaagat tgtgtaccgt gatctcaagt ggagaatct       840
aatgctggac aaagatggcc acataaaaat tacagatttt ggactttgca agaagggat      900
cacagatgca gccaccatga agacattctg tggcactcca gaatatctgg caccagaggt     960
gttagaagat aatgactatg ccgagcagt agactggtgg ggcctagggg ttgtcatgta    1020
tgaaatgatg tgtgggaggt tacctttcta caaccaggac catgagaaac ttttttgaatt   1080
aatattaatg gaagacatta aatttcctcg aacactctct tcagatgcaa aatcattgct    1140
ttcagggctc ttgataaagg atccaaataa acgccttggt ggaggaccag atgatgcaaa   1200
agaaattatg agacacagtt tcttctctgg agtaaactgg caagatgtat atgataaaaa    1260
gcttgtaccct cctttttaaac ctcaagtaac atctgagaca gatactagat attttgatga    1320
agaatttaca gctcagacta ttacaataac accacctgaa aaatatgatg aggatggtat     1380
ggactgcatg gacaatgaga ggcggccgca ttttccctcaa ttttcctact ctgcaagtgg    1440
acgagaataa gtctctttca ttctgctact tcactgtcat cttcaatta ttactgaaaa       1500
tgattcctgg acatcaccag tcctagctct tacacatagc aggggca                   1547
```

<210> SEQ ID NO 4
<211> LENGTH: 4465
<212> TYPE: DNA
<213> ORGANISM: Homo sapiens

<400> SEQUENCE: 4

```
cctgcagcct ccggagtcag tgccgcgcgc ccgccgcccc gcgccttcct gctcgccgca      60
cctccgggag ccggggcgca cccagcccgc agcgccgcct cccgccccgc gccgcctccg    120
accgcaggcc gagggccgcc actggccggg gggaccgggc agcagcttgc ggccgcggag     180
ccgggcaacg ctggggactg cgccttttgt ccccggaggt ccctggaagt ttgcggcagg    240
acgcgcgcgg ggaggcggcg gaggcagccc cgacgtcgcg gagaacaggg cgcagagccg    300
gcatgggcat cgggcgcagc gaggggggcc gccgcgggc agccctgggc gtgctgctgg     360
cgctgggcgc ggcgcttctg gccgtgggct cggccagcga gtacgactac gtgagcttcc    420
agtcggacat cggcccgtac cagagcgggc gcttctacac caagccacct cagtgcgtgg    480
acatccccgc ggacctgcgg ctgtgccaca acgtgggcta caagaagatg gtgctgccca    540
acctgctgga gcacgagacc atggcggagg tgaagcagca ggccagcagc tgggtgcccc    600
tgctcaacaa gaactgccac gccggcaccc aggtcttcct ctgctcgctc ttcgcgcccg    660
tctgcctgga ccggccccat taccgtgtc gctggctctg cgaggccgtg cgcgactcgt    720
gcgagccggt catgcagttc ttcggcttct actggcccga gatgcttaag tgtgacaagt    780
tccccgaggg ggacgtctgc atcgccatga cgccgcccaa tgccaccgaa gcctccaagc    840
```

```
cccaaggcac aacggtgtgt cctccctgtg acaacgagtt gaaatctgag gccatcattg    900
aacatctctg tgccagcgag tttgcactga ggatgaaaat aaaagaagtg aaaaagaaa    960
atggcgacaa gaagattgtc cccaagaaga gaagcccct gaagttgggg cccatcaaga   1020
agaaggacct gaagaagctt gtgctgtacc tgaagaatgg ggctgactgt ccctgccacc   1080
agctggacaa cctcagccac cacttcctca tcatgggccg caaggtgaag agccagtact   1140
tgctgacggc catccacaag tgggacaaga aaaacaagga gttcaaaaac ttcatgaaga   1200
aaatgaaaaa ccatgagtgc cccacctttc agtccgtgtt taagtgattc tcccgggggc   1260
agggtgggga gggagcctcg ggtggggtgg gagcgggggg gacagtgccc cgggaacccg   1320
gtgggtcaca cacacgcact gcgcctgtca gtagtggaca ttgtaatcca gtcggcttgt   1380
tcttgcagca ttcccgctcc cttccctcca tagccacgct ccaaaccca gggtagccat   1440
ggccgggtaa agcaagggcc atttagatta ggaaggtttt taagatccgc aatgtggagc   1500
agcagccact gcacaggagg aggtgacaaa ccatttccaa cagcaacaca gccactaaaa   1560
cacaaaaagg gggattgggc ggaaagtgag agccagcagc aaaaactaca ttttgcaact   1620
tgttggtgtg gatctattgg ctgatctatg cctttcaact agaaaattct aatgattggc   1680
aagtcacgtt gttttcaggt ccagagtagt ttctttctgt ctgctttaaa tggaaacaga   1740
ctcataccac acttacaatt aaggtcaagc ccagaaagtg ataagtgcag ggaggaaaag   1800
tgcaagtcca ttatgtaata gtgacagcaa agggaccagg ggagaggcat tgccttctct   1860
gcccacagtc tttccgtgtg attgtctttg aatctgaatc agccagtctc agatgcccca   1920
aagtttcggt tcctatgagc ccggggcatg atctgatccc caagacatgt ggaggggcag   1980
cctgtgcctg cctttgtgtc agaaaaagga accacagtg agcctgagag agacggcgat   2040
tttcgggctg agaaggcagt agttttcaaa acacatagtt aaaaaagaaa caaatgaaaa   2100
aaattttaga acagtccagc aaattgctag tcagggtgaa ttgtgaaatt gggtgaagag   2160
cttaggattc taatctcatg ttttttcctt ttcacatttt taaaagaaca atgacaaaca   2220
cccacttatt tttcaaggtt ttaaaacagt ctacattgag catttgaaag gtgtgctaga   2280
acaaggtctc ctgatccgtc cgaggctgct tcccagagga gcagctctcc ccaggcattt   2340
gccaagggag gcggatttcc ctggtagtgt agctgtgtgg cttccttcc tgaagagtcc   2400
gtggttgccc tagaacctaa cacccctag caaaactcac agagctttcc gttttttct   2460
ttcctgtaaa gaaacatttc ctttgaactt gattgcctat ggatcaaaga aattcagaac   2520
agcctgcctg tccccccgca cttttacat atatttgttt catttctgca gatggaaagt   2580
tgacatgggt ggggtgtccc catccagcga gagagtttca aaagcaaaac atctctgcag   2640
ttttccccaa gtaccctgag atacttccca aagcccttat gtttaatcag cgatgtatat   2700
aagccagttc acttagacaa ctttacccctt cttgtccaat gtacaggaag tagttctaaa   2760
aaaaatgcat attaatttct tccccaaag ccggattctt aattctctgc aacactttga   2820
ggacatttat gattgtccct ctgggccaat gcttatacc agtgaggatg ctgcagtgag   2880
gctgtaaagt ggcccctgc ggcctagcc tgacccggag gaaggatgg tagattctgt   2940
taactcttga agactccagt atgaaaatca gcatgcccgc ctagttacct accggagagt   3000
tatcctgata aattaacctc tcacagttag tgatcctgtc cttttaacac cttttttgtg   3060
gggttctctc tgacctttca tcgtaaagtg ctggggacct taagtgattt gcctgtaatt   3120
ttggatgatt aaaaaatgtg tatatatatt agctaattag aaatattcta cttctctgtt   3180
gtcaaactga aattcagagc aagttcctga gtgcgtggat ctgggtctta gttctggttg   3240
```

```
attcactcaa gagttcagtg ctcatacgta tctgctcatt ttgacaaagt gcctcatgca    3300
accgggccct ctctctgcgg cagagtcctt agtggagggg tttacctgga acattagtag    3360
ttaccacaga atacggaaga gcaggtgact gtgctgtgca gctctctaaa tgggaattct    3420
caggtaggaa gcaacagctt cagaaagagc tcaaaataaa ttggaaatgt gaatcgcagc    3480
tgtgggtttt accaccgtct gtctcagagt cccaggacct tgagtgtcat tagttacttt    3540
attgaaggtt ttagacccat agcagctttg tctctgtcac atcagcaatt tcagaaccaa    3600
aagggaggct ctctgtaggc acagagctgc actatcacga gcctttgttt ttctccacaa    3660
agtatctaac aaaaccaatg tgcagactga ttggcctggt cattggtctc cgagagagga    3720
ggtttgcctg tgatttccta attatcgcta gggccaaggt gggatttgta aagctttaca    3780
ataatcattc tggatagagt cctgggaggt ccttggcaga actcagttaa atctttgaag    3840
aatatttgta gttatcttag aagatagcat gggaggtgag gattccaaaa acattttatt    3900
tttaaaatat cctgtgtaac acttggctct tggtacctgt gggttagcat caagttctcc    3960
ccagggtaga attcaatcag agctccagtt tgcatttgga tgtgtaaatt acagtaatcc    4020
catttcccaa acctaaaatc tgttttctc atcagactct gagtaactgg ttgctgtgtc    4080
ataacttcat agatgcagga ggctcaggtg atctgtttga ggagagcacc ctaggcagcc    4140
tgcagggaat aacatactgg ccgttctgac ctgttgccag cagatacaca ggacatggat    4200
gaaattcccg tttcctctag tttcttcctg tagtactcct cttttagatc ctaagtctct    4260
tacaaaagct tgaatactg tgaaaatgtt ttacattcca tttcatttgt gttgtttttt    4320
taactgcatt ttaccagatg ttttgatgtt atcgcttatg ttaatagtaa ttcccgtacg    4380
tgttcatttt attttcatgc ttttcagcc atgtatcaat attcacttga ctaaaatcac    4440
tcaattaatc aatgaaaaaa aaaaa                                          4465

<210> SEQ ID NO 5
<211> LENGTH: 314
<212> TYPE: PRT
<213> ORGANISM: Homo sapiens

<400> SEQUENCE: 5

Met Gly Ile Gly Arg Ser Glu Gly Gly Arg Gly Ala Ala Leu Gly
1               5                   10                  15

Val Leu Leu Ala Leu Gly Ala Ala Leu Leu Ala Val Gly Ser Ala Ser
            20                  25                  30

Glu Tyr Asp Tyr Val Ser Phe Gln Ser Asp Ile Gly Pro Tyr Gln Ser
        35                  40                  45

Gly Arg Phe Tyr Thr Lys Pro Pro Gln Cys Val Asp Ile Pro Ala Asp
    50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gln Gln Ala Ser Ser
                85                  90                  95

Trp Val Pro Leu Leu Asn Lys Asn Cys His Ala Gly Thr Gln Val Phe
            100                 105                 110

Leu Cys Ser Leu Phe Ala Pro Val Cys Leu Asp Arg Pro Ile Tyr Pro
        115                 120                 125

Cys Arg Trp Leu Cys Glu Ala Val Arg Asp Ser Cys Glu Pro Val Met
    130                 135                 140

Gln Phe Phe Gly Phe Tyr Trp Pro Glu Met Leu Lys Cys Asp Lys Phe
145                 150                 155                 160
```

```
Pro Glu Gly Asp Val Cys Ile Ala Met Thr Pro Pro Asn Ala Thr Glu
            165                 170                 175
Ala Ser Lys Pro Gln Gly Thr Thr Val Cys Pro Pro Cys Asp Asn Glu
        180                 185                 190
Leu Lys Ser Glu Ala Ile Ile Glu His Leu Cys Ala Ser Glu Phe Ala
    195                 200                 205
Leu Arg Met Lys Ile Lys Glu Val Lys Glu Asn Gly Asp Lys Lys
210                 215                 220
Ile Val Pro Lys Lys Lys Pro Leu Lys Leu Gly Pro Ile Lys Lys
225                 230                 235                 240
Lys Asp Leu Lys Lys Leu Val Leu Tyr Leu Lys Asn Gly Ala Asp Cys
            245                 250                 255
Pro Cys His Gln Leu Asp Asn Leu Ser His His Phe Leu Ile Met Gly
        260                 265                 270
Arg Lys Val Lys Ser Gln Tyr Leu Leu Thr Ala Ile His Lys Trp Asp
    275                 280                 285
Lys Lys Asn Lys Glu Phe Lys Asn Phe Met Lys Met Lys Asn His
    290                 295                 300
Glu Cys Pro Thr Phe Gln Ser Val Phe Lys
305                 310

<210> SEQ ID NO 6
<211> LENGTH: 2005
<212> TYPE: DNA
<213> ORGANISM: Homo sapiens

<400> SEQUENCE: 6
caacggctca ttctgctccc ccgggtcgga gccccccgga gctgcgcgcg ggcttgcagc      60
gcctcgcccg cgctgtcctc ccggtgtccc gcttctccgc gccccagccg ccggctgcca     120
gcttttcggg gccccgagtc gcacccagcg aagagagcgg gcccgggaca agctcgaact     180
ccggccgcct cgcccttccc cggctccgct ccctctgccc cctcggggtc gcgcgcccac     240
gatgctgcag ggcctggct cgctgctgct gtcttcctc gcctcgcact gctgcctggg     300
ctcggcgcgc gggctcttcc tctttggcca gcccgacttc tcctacaagc gcagcaattg     360
caagcccatc cctgccaacc tgcagctgtg ccacggcatc gaataccaga acatgcggct     420
gcccaacctg ctgggccacg agaccatgaa ggaggtgctg agcaggccg cgcttggat     480
cccgctggtc atgaagcagt gccacccgga caccaagaag ttcctgtgct cgctcttcgc     540
ccccgtctgc ctcgatgacc tagacgagac catccagcca tgccactcgc tctgcgtgca     600
ggtgaaggac cgctgcgccc cggtcatgtc cgccttcggc ttccctggc ccgacatgct     660
tgagtgcgac cgtttccccc aggacaacga cctttgcatc cccctcgcta gcagcgacca     720
cctcctgcca gccaccgagg aagctccaaa ggtatgtgaa gcctgcaaaa ataaaaatga     780
tgatgacaac gacataatgg aaacgctttg taaaaatgat tttgcactga aaataaaagt     840
gaaggagata acctacatca accgagatac caaaatcatc ctggagacca agagcaagac     900
catttacaag ctgaacggtg tgtccgaaag ggacctgaag aaatcggtgc tgtggctcaa     960
agacagcttg cagtgcacct gtgaggagat gaacgacatc aacgcgccct atctggtcat    1020
gggacagaaa cagggtgggg agctggtgat cacctcggtg aagcggtggc agaagggggca    1080
gagagagttc aagcgcatct cccgcagcat ccgcaagctg cagtgctagt cccggcatcc    1140
tgatggctcc gacaggcctg ctccagagca cggctgacca tttctgctcc gggatctcag    1200
ctccccgttcc ccaagcacac tcctagctgc tccagtctca gcctgggcag cttccccctg   1260
```

```
cctttTgcac gtttgcatcc ccagcatttc ctgagttata aggccacagg agtggatagc    1320
tgttttcacc taaaggaaaa gcccacccga atcttgtaga aatattcaaa ctaataaaat    1380
catgaatatt tttatgaagt ttaaaaatag ctcactttaa agctagtttt gaataggtgc    1440
aactgtgact tgggtctggt tggttgttgt ttgttgtttt gagtcagctg attttcactt    1500
cccactgagg ttgtcataac atgcaaattg cttcaatttt ctctgtggcc caaacttgtg    1560
ggtcacaaac cctgttgaga taaagctggc tgttatctca acatcttcat cagctccaga    1620
ctgagactca gtgtctaagt cttacaacaa ttcatcattt tataccttca atggaacttt    1680
aaactgttac atgtatcaca ttccagctac aatacttcca tttattagaa gcacattaac    1740
catttctata gcatgatttc ttcaagtaaa aggcaaaaga tataaatttt ataattgact    1800
tgagtacttt aagccttgtt taaaacattt cttacttaac ttttgcaaat taaacccatt    1860
gtagcttacc tgtaatatac atagtagttt acctttaaaa gttgtaaaaa tattgcttta    1920
accaacactg taaatatttc agataaacat tatattcttg tatataaact ttacatcctg    1980
ttttacctat aaaaaaaaaa aaaaa                                          2005
```

<210> SEQ ID NO 7
<211> LENGTH: 295
<212> TYPE: PRT
<213> ORGANISM: Homo sapiens

<400> SEQUENCE: 7

```
Met Leu Gln Gly Pro Gly Ser Leu Leu Leu Phe Leu Ala Ser His
 1               5                  10                  15

Cys Cys Leu Gly Ser Ala Arg Gly Leu Phe Leu Phe Gly Gln Pro Asp
            20                  25                  30

Phe Ser Tyr Lys Arg Ser Asn Cys Lys Pro Ile Pro Ala Asn Leu Gln
        35                  40                  45

Leu Cys His Gly Ile Glu Tyr Gln Asn Met Arg Leu Pro Asn Leu Leu
    50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln
            100                 105                 110

Pro Cys His Ser Leu Cys Val Gln Val Lys Asp Arg Cys Ala Pro Val
        115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240
```

```
Asp Ser Leu Gln Cys Thr Cys Glu Glu Met Asn Asp Ile Asn Ala Pro
            245                 250                 255

Tyr Leu Val Met Gly Gln Lys Gln Gly Glu Leu Val Ile Thr Ser
        260                 265                 270

Val Lys Arg Trp Gln Lys Gly Gln Arg Glu Phe Lys Arg Ile Ser Arg
        275                 280                 285

Ser Ile Arg Lys Leu Gln Cys
        290                 295

<210> SEQ ID NO 8
<211> LENGTH: 2058
<212> TYPE: DNA
<213> ORGANISM: Homo sapiens

<400> SEQUENCE: 8
```

| | | | | | |
|---|---|---|---|---|---|
| gttgggaaag | agcagcctgg | gcggcagggg | cggtggctgg | agctcggtaa | agctcgtggg | 60 |
| accccattgg | gggaatttga | tccaaggaag | cggtgattgc | cggggagga | gaagctccca | 120 |
| gatccttgtg | tccacttgca | gcggggagg | cggagacggc | ggagcgggcc | ttttggcgtc | 180 |
| cactgcgcgg | ctgcaccctg | ccccatcctg | ccgggatcat | ggtctgcggc | agcccgggag | 240 |
| ggatgctgct | gctgcgggcc | gggctgcttg | ccctggctgc | tctctgcctg | ctccgggtgc | 300 |
| ccggggctcg | ggctgcagcc | tgtgagcccg | tccgcatccc | cctgtgcaag | tccctgccct | 360 |
| ggaacatgac | taagatgccc | aaccacctgc | accacagcac | tcaggccaac | gccatcctgg | 420 |
| ccatcgagca | gttcgaaggt | ctgctgggca | cccactgcag | ccccgatctg | ctcttcttcc | 480 |
| tctgtgccat | gtacgcgccc | atctgcacca | ttgacttcca | gcacgagccc | atcaagccct | 540 |
| gtaagtctgt | gtgcgagcgg | gcccggcagg | gctgtgagcc | catactcatc | aagtaccgcc | 600 |
| actcgtggcc | ggagaacctg | gcctgcgagg | agctgccagt | gtacgacagg | ggcgtgtgca | 660 |
| tctctcccga | ggccatcgtt | actgcggacg | gagctgattt | tcctatggat | tctagtaacg | 720 |
| gaaactgtag | aggggcaagc | agtgaacgct | gtaaatgtaa | gcctattaga | gctacacaga | 780 |
| agacctattt | ccggaacaat | tacaactatg | tcattcgggc | taaagttaaa | gagataaaga | 840 |
| ctaagtgcca | tgatgtgact | gcagtagtgg | aggtgaagga | gattctaaag | tcctctctgg | 900 |
| taaacattcc | acgggacact | gtcaacctct | ataccagctc | tggctgcctc | tgccctccac | 960 |
| ttaatgttaa | tgaggaatat | atcatcatgg | gctatgaaga | tgaggaacgt | tccagattac | 1020 |
| tcttggtgga | aggctctata | gctgagaagt | ggaaggatcg | actcggtaaa | aaagttaagc | 1080 |
| gctgggatat | gaagcttcgt | catcttggac | tcagtaaaag | tgattctagc | aatagtgatt | 1140 |
| ccactcagag | tcagaagtct | ggcaggaact | cgaaccccg | gcaagcacgc | aactaaatcc | 1200 |
| cgaaatacaa | aaagtaacac | agtggacttc | ctattaagac | ttacttgcat | tgctggacta | 1260 |
| gcaaaggaaa | attgcactat | tgcacatcat | attctattgt | ttactataaa | aatcatgtga | 1320 |
| taactgatta | ttacttctgt | ttctcttttg | gtttctgctt | ctctcttctc | tcaacccctt | 1380 |
| tgtaatggtt | tgggggcaga | ctcttaagta | tattgtgagt | tttctatttc | actaatcatg | 1440 |
| agaaaaactg | ttcttttgca | ataataataa | attaaacatg | ctgttaccag | agcctctttg | 1500 |
| ctggagtctc | cagatgttaa | tttacttttct | gcaccccaat | tgggaatgca | atattggatg | 1560 |
| aaaagagagg | tttctggtat | tcacagaaag | ctagatatgc | cttaaaacat | actctgccga | 1620 |
| tctaattaca | gccttatttt | tgtatgcctt | ttgggcattc | tcctcatgct | tagaaagttc | 1680 |
| caaatgttta | taaggtaaa | atggcagttt | gaagtcaaat | gtcacatagg | caaagcaatc | 1740 |
| aagcaccagg | aagtgtttat | gaggaaacaa | cacccaagat | gaattatttt | tgagactgtc | 1800 |

-continued

```
aggaagtaaa ataaatagga gcttaagaaa gaacattttg cctgattgag aagcacaact    1860
gaaaccagta gccgctgggg tgttaatggt agcattcttc ttttggcaat acatttgatt    1920
tgttcatgaa tatattaatc agcattagag aaatgaatta taactagaca tctgctgtta    1980
tcaccatagt tttgtttaat ttgcttcctt ttaaataaac ccattggtga aagtcccaaa    2040
aaaaaaaaaa aaaaaaa                                                   2058
```

<210> SEQ ID NO 9
<211> LENGTH: 325
<212> TYPE: PRT
<213> ORGANISM: Homo sapiens

<400> SEQUENCE: 9

```
Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
                20                  25                  30

Ala Ala Cys Glu Pro Val Arg Ile Pro Leu Cys Lys Ser Leu Pro Trp
            35                  40                  45

Asn Met Thr Lys Met Pro Asn His Leu His His Ser Thr Gln Ala Asn
50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Asn Leu Ala Cys Glu Glu Leu Pro Val Tyr Asp Arg
130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
        195                 200                 205

Lys Cys His Asp Val Thr Ala Val Val Glu Val Lys Glu Ile Leu Lys
    210                 215                 220

Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Glu Arg Ser Arg Leu Leu Leu Val Glu Gly
            260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Ser Lys Ser Asp Ser Ser
    290                 295                 300

Asn Ser Asp Ser Thr Gln Ser Gln Lys Ser Gly Arg Asn Ser Asn Pro
305                 310                 315                 320

Arg Gln Ala Arg Asn
                325
```

```
<210> SEQ ID NO 10
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 10
cggauuguaa agaacugcat t                                              21

<210> SEQ ID NO 11
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 11
ugcaguucuu uacaauccgt t                                              21

<210> SEQ ID NO 12
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 12
ggacgacaac gacaucaugt t                                              21

<210> SEQ ID NO 13
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 13
caugaugucg uugucgucct c                                              21

<210> SEQ ID NO 14
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 14
ccgucaaucu uuauaccact t                                              21

<210> SEQ ID NO 15
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 15
gugguauaaa gauugacggt g                                              21

<210> SEQ ID NO 16
<211> LENGTH: 4091
<212> TYPE: DNA
<213> ORGANISM: Homo sapiens

<400> SEQUENCE: 16
```

```
gccggagtcg gagggcgggg agctaggagg agggagctcg agagttgtgg agactagtga    60
ctgggagaag tcgcagcccg ctcaggcccg cgccttcccg ctccccgtct tcctctctca   120
cacacctact ccgccctccg ccccagcccg cgcgctagct ccttctctcg cccgggttc    180 ctgccggtag ctctccgggt cttggcgcgg cggggggcgcc ccggggtgc cctcgccctc   240 ccgttgcggg cgggcgggcg gtatgtggcg cctggtgccc ccgaagctgg gccgcctgtc   300
ccgctcgctg aagctggcgg cgctgggcag cctgttggtg ctgatggtgc tgcactcgcc   360
gtcgctgctc gcctcttggc agcgcaacga actgaccgac cggcgcttcc tgcagctcaa   420
taagtgcccg gcgtgcttcg gcacgagctg gtgccgccgc ttcctcaacg ggcaggtggt   480
attcgaggcg tggggccgct tgcgcctgct ggacttcctc aacgtgaaga acgtgtactt   540
cgcgcagtac ggcgagcccc gcgagggcgg ccgccgccga gtggtgctca agcgcctcgg   600
ctcgcagcgc gagctggcgc agctcgacca gagcatctgc aagcgggcca ccggccggcc   660
ccgctgcgac ctgctgcagg ccatgccccg gaccgagttc gcgcgcctca acggcgacgt   720
gcgtctgctc acgcccgagg cggtggaggg ctggtcggac ctggtgcact gccccctcgca   780 gcgccttctc gaccgcctgg tgcgccgcta cgcggagacc aaggactcgg gcagcttcct   840
gcttcgcaac ctcaaggact cggagcgcat gcagctgctg ctgaccctgg ccttcaaccc   900
cgagccgctg tgctacaga gttttccgtc tgatgaaggt tggccatttg caaagtatct   960
tggagcttgt ggaagaatgg tggctgtaaa ttatgttgga aagaactgt ggagttactt  1020 taatgcgcca tgggaaaaac gagttgacct cgcttggcaa ttaatggaaa tagcagaaca  1080
gcttacaaac aatgactttg aatttgcact ctacctcctg gacgtcagct ttgacaattt  1140
tgcagttggt cctagagatg ggaaggtaat cattgtggat gctgaaaatg ttttggttgc  1200
tgacaaaaga ttaattagac aaaataaacc tgaaaattgg gatgtatggt atgaaagcaa  1260
gtttgatgac tgtgataagg aggcttgctt atcatttcca aaagaaattc tttgtgctcg  1320
tgccactgtg gaccacaatt actatgctgt ttgtcagaac ctcttatcca gacatgccac  1380
ctggcgtggc acttctggag gactccttca tgatccacca agtgaaattg ccaaagatgg  1440
ccggctcgag gccttgctgg atgagtgtgc caacccaaag aagcgctatg gcagattcca  1500
ggctgcaaaa gaactgcgtg aatacctagc acaattaagt aacaacgtga ggtagtctat  1560
ggtgaacttt tcttttttc tccatttaaa cagcactggc taaaactaaa ccaccaaaaa  1620
acgatctgaa aaaatgaaat ttggaagtgt tacattcaga ggatgataaa cttgcactga  1680
tagatcttaa tgttaacatc catcaaaata agacattact tcaaaaatca catgatgctt  1740
ctgcaaataa gtatgttctt atactttgga ggcttgagct gtcatcagct gctccccact  1800
accccggaat gcttgagtgg attaatgaat attgttaagc tattggaaat gagtctgata  1860
gtacattggc ttgtgtatca aagggtactt ggtacttagt ttgcatttac tatcatgatt  1920
ttgtgaatct cttgcattta ctttgaatgt caagtcagat tggtctgttt tataggccgc  1980
tttttccttc tgatgtgtag ggttttttcc ccctttttt ttttaattaa attttgaaaa  2040
ttcaggttac tgtaggtgtt catttaaatt tttaatagtt gtcattcagt gctatttggt  2100
acatatttac tgttagggca ggattcccag gtttactgtg ttttttttt ttttttttta  2160 aagaaagcta aatattacat tatgtaaata cttcttttca ccaacttctg tagtttcacc  2220
attgcatggt gtcatttcag gttatttaac agttatatcc ctctatgcca ataattagaa  2280
gtgtacacta acatgaagt ttggcatatg ttgcaaaatg tcattttatc tttctaaagg   2340 cttaagaag aatatactag aatctatata ttgatgttaa ttttgattca gaaaaaaat   2400
```

```
acaacccagt atctaaaaag tgttaactag tccaagatag taatgcatat gccaaagaaa    2460
tattacacct aatctcatgt ttagaattta aaatagaatt ggtcagctac ttattcttac    2520
caccctactt ccagtatttt agctctgtca ttattaaatt cagatcttcc tgattatttt    2580
ttctgttgaa agttaaacta ctgctttcaa gtaatttaaa gttatcctac cttttattca    2640
tgggtagttt tgcaaaatta acatggtagc cattgtttga atttaatcgg gcatcataac    2700
ttttcattta ttgaggaact aatcattatt actataaagc atacaaatta gccagtcagc    2760
acactttggt cttctttacc taagggttaa acatcagaac atcaaattta attatttgca    2820
tagaaatgtg tgggctcttt atataagttg actatcacta acaggtaata ttttctgtt     2880 tgaagttgtt acttttgttt acagcaaagt ttgatgtagt gtgcagtagt gagctctaga    2940
ctgatctttt tctaaatcag aaagtgatta agtatgcac aaccaaaggc aggttttct      3000 ttttcattta ttcagcaact atttattaag catcaactct gtgccaggca cgttactagc    3060
tgctacatac tgtctgaaca tgacatacgg ttaagtaact ttacaattat tatcaaatac    3120
ttcaatgtag atatttctta agttgaaata gcattaacta ggataatgct ttcatgttat    3180
tttattgtct tgtgatagaa attcaacttg taccatctaa aactaggttg ctataaaaat    3240
aggaggatga agtcaataaa gtttatgcca gtttaaaaac tggaaggaaa aggtaagagc    3300
tctccattat aaaatagttg cattcggtta attttacac attagtgcat gcgtatatc      3360 aactggccct caatgaagca tttaagtgct tggaatttta ctaaactgac ttttttgcaa    3420
ctttgggaga ttttttgaggg gagtgttgaa aattgccaaa cactcacctc ttactcaaaa    3480
cttcaaataa aatacacatt ttcaagaggg agcacctttt atatttgata agtttttcatt  3540 ataaaccta taataccagt cacaaagagg ttgtctgtct atggtttagc aaacatttgc     3600 ttttctttt ggaagtgtga ttgcaattgc agaacagaaa gtgagaaaac actgccagcg     3660
gtgattgcta cttgaggtag ttttttacaa ctaccattc ccctccatga aattatgtga     3720
aatttatttt atctttggga aaagttgaga agatagtaaa agaattagga atttaaaatt    3780
acagggaaaa atatgtaagt gaaaagcaat aaatattttg ttcactttgc tatcaagatg    3840
ttcactatca gatatttatt atatggcagc aatttatatt tttaatcatt gcccattaat    3900
agacgcagta aaatatttt gaatcagaca tttgggggttt gtatgtgcat taaaattgtc    3960
ttttgtactg taagttactg ttaatttgaa tattttattg aactgtctcc ctgtgccttt    4020
ataatataaa gttgtttcta caacttttaa tgatcttaat aaagaatact ttaggaaaaa    4080 aaaaaaaaa a                                                         4091
```

<210> SEQ ID NO 17
<211> LENGTH: 430
<212> TYPE: PRT
<213> ORGANISM: Homo sapiens

<400> SEQUENCE: 17

```
Met Trp Arg Leu Val Pro Pro Lys Leu Gly Arg Leu Ser Arg Ser Leu
1               5                   10                  15

Lys Leu Ala Ala Leu Gly Ser Leu Leu Val Leu Met Val Leu His Ser
            20                  25                  30

Pro Ser Leu Leu Ala Ser Trp Gln Arg Asn Glu Leu Thr Asp Arg Arg
        35                  40                  45

Phe Leu Gln Leu Asn Lys Cys Pro Ala Cys Phe Gly Thr Ser Trp Cys
    50                  55                  60

Arg Arg Phe Leu Asn Gly Gln Val Val Phe Glu Ala Trp Gly Arg Leu
```

|   |   |   |   |   |   |   |   |   |   |   |   |   |   |   |   |
|---|---|---|---|---|---|---|---|---|---|---|---|---|---|---|---|
| | | | 65 | | | | 70 | | | | 75 | | | | 80 |
| Arg | Leu | Leu | Asp | Phe | Leu | Asn | Val | Lys | Asn | Val | Tyr | Phe | Ala | Gln | Tyr |
| | | | | 85 | | | | 90 | | | | 95 | | | |
| Gly | Glu | Pro | Arg | Glu | Gly | Arg | Arg | Val | Val | Leu | Lys | Arg | Leu | | |
| | | | 100 | | | | 105 | | | | 110 | | | | |
| Gly | Ser | Gln | Arg | Glu | Leu | Ala | Gln | Leu | Asp | Gln | Ser | Ile | Cys | Lys | Arg |
| | | 115 | | | | 120 | | | | 125 | | | | | |
| Ala | Thr | Gly | Arg | Pro | Arg | Cys | Asp | Leu | Leu | Gln | Ala | Met | Pro | Arg | Thr |
| 130 | | | | | 135 | | | | | 140 | | | | | |
| Glu | Phe | Ala | Arg | Leu | Asn | Gly | Asp | Val | Arg | Leu | Leu | Thr | Pro | Glu | Ala |
| 145 | | | | | 150 | | | | | 155 | | | | | 160 |
| Val | Glu | Gly | Trp | Ser | Asp | Leu | Val | His | Cys | Pro | Ser | Gln | Arg | Leu | Leu |
| | | | | 165 | | | | | 170 | | | | | 175 | |
| Asp | Arg | Leu | Val | Arg | Arg | Tyr | Ala | Glu | Thr | Lys | Asp | Ser | Gly | Ser | Phe |
| | | | 180 | | | | | 185 | | | | | 190 | | |
| Leu | Leu | Arg | Asn | Leu | Lys | Asp | Ser | Glu | Arg | Met | Gln | Leu | Leu | Leu | Thr |
| | | | 195 | | | | | 200 | | | | | 205 | | |
| Leu | Ala | Phe | Asn | Pro | Glu | Pro | Leu | Val | Leu | Gln | Ser | Phe | Pro | Ser | Asp |
| 210 | | | | | 215 | | | | | 220 | | | | | |
| Glu | Gly | Trp | Pro | Phe | Ala | Lys | Tyr | Leu | Gly | Ala | Cys | Gly | Arg | Met | Val |
| 225 | | | | 230 | | | | | 235 | | | | | 240 | |
| Ala | Val | Asn | Tyr | Val | Gly | Glu | Glu | Leu | Trp | Ser | Tyr | Phe | Asn | Ala | Pro |
| | | | | 245 | | | | | 250 | | | | | 255 | |
| Trp | Glu | Lys | Arg | Val | Asp | Leu | Ala | Trp | Gln | Leu | Met | Glu | Ile | Ala | Glu |
| | | | 260 | | | | | 265 | | | | | 270 | | |
| Gln | Leu | Thr | Asn | Asn | Asp | Phe | Glu | Phe | Ala | Leu | Tyr | Leu | Leu | Asp | Val |
| | | | 275 | | | | | 280 | | | | | 285 | | |
| Ser | Phe | Asp | Asn | Phe | Ala | Val | Gly | Pro | Arg | Asp | Gly | Lys | Val | Ile | Ile |
| | 290 | | | | | 295 | | | | | 300 | | | | |
| Val | Asp | Ala | Glu | Asn | Val | Leu | Val | Ala | Asp | Lys | Arg | Leu | Ile | Arg | Gln |
| 305 | | | | | 310 | | | | | 315 | | | | | 320 |
| Asn | Lys | Pro | Glu | Asn | Trp | Asp | Val | Trp | Tyr | Glu | Ser | Lys | Phe | Asp | Asp |
| | | | | 325 | | | | | 330 | | | | | 335 | |
| Cys | Asp | Lys | Glu | Ala | Cys | Leu | Ser | Phe | Ser | Lys | Glu | Ile | Leu | Cys | Ala |
| | | | 340 | | | | | 345 | | | | | 350 | | |
| Arg | Ala | Thr | Val | Asp | His | Asn | Tyr | Tyr | Ala | Val | Cys | Gln | Asn | Leu | Leu |
| | | | 355 | | | | | 360 | | | | | 365 | | |
| Ser | Arg | His | Ala | Thr | Trp | Arg | Gly | Thr | Ser | Gly | Gly | Leu | Leu | His | Asp |
| | | | 370 | | | | | 375 | | | | | 380 | | |
| Pro | Pro | Ser | Glu | Ile | Ala | Lys | Asp | Gly | Arg | Leu | Glu | Ala | Leu | Leu | Asp |
| 385 | | | | | 390 | | | | | 395 | | | | | 400 |
| Glu | Cys | Ala | Asn | Pro | Lys | Lys | Arg | Tyr | Gly | Arg | Phe | Gln | Ala | Ala | Lys |
| | | | | 405 | | | | | 410 | | | | | 415 | |
| Glu | Leu | Arg | Glu | Tyr | Leu | Ala | Gln | Leu | Ser | Asn | Asn | Val | Arg | | |
| | | | 420 | | | | | 425 | | | | | 430 | | |

<210> SEQ ID NO 18
<211> LENGTH: 2437
<212> TYPE: DNA
<213> ORGANISM: Homo sapiens

<400> SEQUENCE: 18

```
gcatcttggc agggtccggg gacgtggact atttcgcaca ccacaccacg gggagggatt      60
ttttctatt ttccctacga aaacagatc tttttaagga tggtgctgct ccactggtgc      120
```

```
ctgctgtggc tcctgtttcc actcagctca aggacccaga agttacccac ccgggatgag    180
gaacttttc agatgcagat ccgggacaag gcattttttc atgattcgtc agtaattcca    240
gatggagctg aaattagcag ttatctcttt agagatacac ctaaaaggta tttctttgtg    300
gttgaagaag acaatactcc attatcagtc acagtgacgc cctgtgatgc gcctttggag    360
tggaagctga gcctccagga gctgccagag acaggagcg gggaaggctc aggtgatctg    420
gaacctcttg agcagcagaa gcagcagatc attaatgagg aaggcactga gttattctcc    480
tacaaaggca atgatgttga gtattttata tcgtctagtt ccccatccgg tttgtatcag    540
ttggatcttc tttcaacaga gaaagacaca catttcaaag tatatgccac cacaactcca    600
gaatctgatc agccataccc tgagttaccc tatgacccaa gagtagatgt gacctcactg    660
gggcgcacca cggtcacttt ggcctggaaa ccaagcccca ctgcctcttt gctgaaacaa    720
cccattcagt actgtgtggt catcaacaaa gagcacaatt tcaaaagtct ctgtgcagtg    780
gaagcaaaac tgagtgcaga tgatgctttt atgatggcac cgaaacctgg tctggacttc    840
agcccctttg actttgccca ctttggattt ccttctgata attcaggtaa agaacgcagt    900
ttccaggcaa agccttctcc aaaactgggg cgtcatgtct actccaggcc caaggttgat    960
attcagaaaa tctgcatagg aaacaagaac atcttcaccg tctctgatct gaaacccgac   1020
acgcagtact actttgatgt atttgtggtc aacatcaaca gcaacatgag caccgcttat   1080
gtaggtacct tgccaggac caaggaagaa gccaaacaga agacagtcga gctaaaagat   1140
gggaagataa cagatgtatt tgttaaaagg aagggagcaa agtttctacg gtttgctcca   1200
gtctcttctc accaaaaagt caccttcttt attcactctt gtctggatgc tgtccaaatc   1260
caagtgagaa gagatgggaa acttcttctg tctcagaatg tggaaggcat tcagcagttt   1320
cagcttagag gaaaacctaa agctaaatac ctcgttcgac tgaaaggaaa caagaaagga   1380
gcatctatgt tgaaaattct agctaccaca aggcctacta gcagtcatt tccctctctt   1440
cctgaagaca caagaatcaa agcctttgac aagctccgta cctgttcctc ggccaccgtg   1500
gcttggctag gcactcagga aaggaacaag ttttgcatct acaaaaaaga agtggatgat   1560
aactacaatg aagaccagaa gaaaagagag caaaaccaat gtctaggacc agatataagg   1620
aagaagtcag aaaaggtcct ctgtaaatat ttccacagtc aaaacttgca gaaagcagtg   1680
accacagaaa caattaaagg tcttcagcct ggcaaatctt acctgctgga tgtttatgtc   1740
ataggacatg gggggcactc tgtaaagtat cagagtaagg ttgtgaaaac tagaaagttc   1800
tgttagttac cttcttatag agatatatta tgtagaactc caggagggac attaaatcac   1860
tttaagtata aactgactac tcccacagtt gagagaagtt gtgacctgta cttgtactat   1920
ggaaggaagg atatcaacgt gtgtatattg atgtttatat aagtaactct tgaaggagac   1980
ttgttctagc gtgccccatg gtacctagtg tgtgtctgat gccggttggt gtcaaagata   2040
gagggcttct tgaaggaact tgccattcct tgctttgacc actgcatgaa ctgcttctaa   2100
attattttat tacctaaaaa tttaaaatat gccattcatt gcacacaccc acaaatgcaa   2160
atcattcctc tctatagatg ctaggatata tataaattat tttataaatt cttgttttaa   2220
atgtcagtgt ttctatgatt gtaaactatt aaattctttt cctattaaag tacagatcta   2280
atctaagtat tattaagttg atagccctct agtcagttat attgctattg taaattcttg   2340
tttgttgagt aaaatgttta aatactatat gtatctcatg tacaaagttg acatacatta   2400
tattcatgta cataaaatta aagagattag attataa                            2437
```

<210> SEQ ID NO 19

<211> LENGTH: 568
<212> TYPE: PRT
<213> ORGANISM: Homo sapiens

<400> SEQUENCE: 19

```
Met Val Leu Leu His Trp Cys Leu Leu Trp Leu Leu Phe Pro Leu Ser
1               5                   10                  15

Ser Arg Thr Gln Lys Leu Pro Thr Arg Asp Glu Glu Leu Phe Gln Met
            20                  25                  30

Gln Ile Arg Asp Lys Ala Phe Phe His Asp Ser Ser Val Ile Pro Asp
        35                  40                  45

Gly Ala Glu Ile Ser Ser Tyr Leu Phe Arg Asp Thr Pro Lys Arg Tyr
    50                  55                  60

Phe Phe Val Val Glu Glu Asp Asn Thr Pro Leu Ser Val Thr Val Thr
65                  70                  75                  80

Pro Cys Asp Ala Pro Leu Glu Trp Lys Leu Ser Leu Gln Glu Leu Pro
                85                  90                  95

Glu Asp Arg Ser Gly Glu Gly Ser Gly Asp Leu Glu Pro Leu Glu Gln
            100                 105                 110

Gln Lys Gln Gln Ile Ile Asn Glu Glu Gly Thr Glu Leu Phe Ser Tyr
        115                 120                 125

Lys Gly Asn Asp Val Gly Tyr Phe Ile Ser Ser Ser Pro Ser Gly
    130                 135                 140

Leu Tyr Gln Leu Asp Leu Leu Ser Thr Glu Lys Asp Thr His Phe Lys
145                 150                 155                 160

Val Tyr Ala Thr Thr Thr Pro Glu Ser Asp Gln Pro Tyr Pro Glu Leu
                165                 170                 175

Pro Tyr Asp Pro Arg Val Asp Val Thr Ser Leu Gly Arg Thr Thr Val
            180                 185                 190

Thr Leu Ala Trp Lys Pro Ser Pro Thr Ala Ser Leu Leu Lys Gln Pro
        195                 200                 205

Ile Gln Tyr Cys Val Val Ile Asn Lys Glu His Asn Phe Lys Ser Leu
    210                 215                 220

Cys Ala Val Glu Ala Lys Leu Ser Ala Asp Ala Phe Met Met Ala
225                 230                 235                 240

Pro Lys Pro Gly Leu Asp Phe Ser Pro Phe Asp Phe Ala His Phe Gly
                245                 250                 255

Phe Pro Ser Asp Asn Ser Gly Lys Glu Arg Ser Phe Gln Ala Lys Pro
            260                 265                 270

Ser Pro Lys Leu Gly Arg His Val Tyr Ser Arg Pro Lys Val Asp Ile
        275                 280                 285

Gln Lys Ile Cys Ile Gly Asn Lys Asn Ile Phe Thr Val Ser Asp Leu
    290                 295                 300

Lys Pro Asp Thr Gln Tyr Tyr Phe Asp Val Phe Val Val Asn Ile Asn
305                 310                 315                 320

Ser Asn Met Ser Thr Ala Tyr Val Gly Thr Phe Ala Arg Thr Lys Glu
                325                 330                 335

Glu Ala Lys Gln Lys Thr Val Glu Leu Lys Asp Gly Lys Ile Thr Asp
            340                 345                 350

Val Phe Val Lys Arg Lys Gly Ala Lys Phe Leu Arg Phe Ala Pro Val
        355                 360                 365

Ser Ser His Gln Lys Val Thr Phe Phe Ile His Ser Cys Leu Asp Ala
    370                 375                 380

Val Gln Ile Gln Val Arg Arg Asp Gly Lys Leu Leu Leu Ser Gln Asn
385                 390                 395                 400
```

```
Val Glu Gly Ile Gln Gln Phe Gln Leu Arg Gly Lys Pro Lys Ala Lys
                405                 410                 415

Tyr Leu Val Arg Leu Lys Gly Asn Lys Gly Ala Ser Met Leu Lys
                420                 425                 430

Ile Leu Ala Thr Thr Arg Pro Thr Lys Gln Ser Phe Pro Ser Leu Pro
                435                 440                 445

Glu Asp Thr Arg Ile Lys Ala Phe Asp Lys Leu Arg Thr Cys Ser Ser
450                 455                 460

Ala Thr Val Ala Trp Leu Gly Thr Gln Glu Arg Asn Lys Phe Cys Ile
465                 470                 475                 480

Tyr Lys Lys Glu Val Asp Asp Asn Tyr Asn Glu Asp Gln Lys Lys Arg
                485                 490                 495

Glu Gln Asn Gln Cys Leu Gly Pro Asp Ile Arg Lys Lys Ser Glu Lys
                500                 505                 510

Val Leu Cys Lys Tyr Phe His Ser Gln Asn Leu Gln Lys Ala Val Thr
                515                 520                 525

Thr Glu Thr Ile Lys Gly Leu Gln Pro Gly Lys Ser Tyr Leu Leu Asp
                530                 535                 540

Val Tyr Val Ile Gly His Gly Gly His Ser Val Lys Tyr Gln Ser Lys
545                 550                 555                 560

Val Val Lys Thr Arg Lys Phe Cys
                565

<210> SEQ ID NO 20
<211> LENGTH: 800
<212> TYPE: DNA
<213> ORGANISM: Homo sapiens

<400> SEQUENCE: 20
agcgggatag cccgcggccg cgcctgcccg ctcgcacccc tctcccgcgc ccggttctcc      60
ctcgcagcac ctcgaagtgc gcccctcgcc ctcctgctcg cgccccgccg ccatggctgc     120
ctcccccgcg cggcctgctg tcctggccct gaccgggctg gcgctgctcc tgctcctgtg     180
ctggggccca ggtggcataa gtggaaataa actcaagctg atgcttcaaa acgagaagc     240 acctgttcca actaagacta aagtggccgt tgatgagaat aaagccaaag aattccttgg     300
cagcctgaag cgccagaagc ggcagctgtg ggaccggact cggcccgagg tgcagcagtg     360
gtaccagcag tttctctaca tgggctttga cgaagcgaaa tttgaagatg acatcaccta     420
ttggcttaac agagatcgaa atggacatga atactatggc gattactacc aacgtcacta     480
tgatgaagac tctgcaattg gtccccggag ccctacggc tttaggcatg agccagcgt      540 caactacgat gactactaac catgacttgc cacacgctgt acaagaagca aatagcgatt     600
ctcttcatgt atctcctaat gccttacact acttggtttc tgatttgctc tatttcagca     660
gatcttttct acctactttg tgtgatcaaa aagaagagt taaacaaca catgtaaatg      720 cctttgata tttcatggga atgcctctca tttaaaaata gaaataaagc attttgttaa      780
aaagaaaaaa aaaaaaaaaa                                                 800

<210> SEQ ID NO 21
<211> LENGTH: 148
<212> TYPE: PRT
<213> ORGANISM: Homo sapiens

<400> SEQUENCE: 21

Met Ala Ala Ser Pro Ala Arg Pro Ala Val Leu Ala Leu Thr Gly Leu
1               5                   10                  15
```

Ala Leu Leu Leu Leu Cys Trp Gly Pro Gly Gly Ile Ser Gly Asn
            20                  25                  30

Lys Leu Lys Leu Met Leu Gln Lys Arg Glu Ala Pro Val Pro Thr Lys
            35                  40                  45

Thr Lys Val Ala Val Asp Glu Asn Lys Ala Lys Glu Phe Leu Gly Ser
        50                  55                  60

Leu Lys Arg Gln Lys Arg Gln Leu Trp Asp Arg Thr Arg Pro Glu Val
65                  70                  75                  80

Gln Gln Trp Tyr Gln Gln Phe Leu Tyr Met Gly Phe Asp Glu Ala Lys
                85                  90                  95

Phe Glu Asp Asp Ile Thr Tyr Trp Leu Asn Arg Asp Arg Asn Gly His
            100                 105                 110

Glu Tyr Tyr Gly Asp Tyr Gln Arg His Tyr Asp Glu Asp Ser Ala
            115                 120                 125

Ile Gly Pro Arg Ser Pro Tyr Gly Phe Arg His Gly Ala Ser Val Asn
        130                 135                 140

Tyr Asp Asp Tyr
145

<210> SEQ ID NO 22
<211> LENGTH: 4533
<212> TYPE: DNA
<213> ORGANISM: Homo sapiens

<400> SEQUENCE: 22

```
cactgggaga cagtccactt aaatgcagct ccagggttgc gaggcaccca ccagcatcat      60
tccccatgcg aggtggcaaa tgcaacatgc tctccagttt ggggtgtcta cttctctgtg     120
gaagtattac actagccctg ggaaatgcac agaaattgcc aaaaggtaaa aggccaaacc     180
tcaaagtcca catcaatacc acaagtgact ccatcctctt gaagttcttg cgtccaagtc     240
caaatgtaaa gcttgaaggt cttctcctgg gatatggcag caatgtatca ccaaaccagt     300
acttccctct tcccgctgaa gggaaattca cagaagctat agttgatgca gagccgaaat     360
atctgatagt tgtgcgacct gctccacctc caagtcaaaa gaagtcatgt tcaggtaaaa     420
ctcgttctcg caaacctctg cagctggtgg ttggcactct gacaccgagc tcagtcttcc     480
tgtcctgggg tttcctcatc aacccacacc atgactggac attgccaagt cactgtccca     540
atgacagatt ttatacaatt cgctatcgag aaaaggataa agaaagaag tggattttc       600 aaatctgtcc agccactgaa acaattgtgg aaaacctaaa gcccaacaca gtttatgaat     660
ttggagtgaa agacaatgtg gaaggtggaa tttggagtaa gattttcaat cacaagactg     720
ttgttggaag taaaaaagta aatgggaaaa tccaaagtac ctatgaccaa gaccacacag     780
tgccagcata tgtcccaagg aaactaatcc aataacaat catcaagcaa gtgattcaga     840
atgttactca caaggattca gctaaatccc cagaaaaagc tccactggga ggagtgatac     900
tagtccacct tattattcca ggtcttaatg aaactactgt aaaacttcct gcatccctaa     960
tgtttgagat tcagatgca ctcaagacac aattagctaa gaatgaaacc ttggcattac     1020
ctgccgaatc taaaacacca gaggttgaaa aaatctcagc acgacccaca acagtgactc     1080
ctgaaacagt tccaagaagc actaaaccca ctacgtctag tgcattagat gtttcagaaa     1140
caacactggc ttcaagtgaa agccatggat tgtgcctac agctaaaata tctgaagatt     1200
ccaaagttct gcagcctcaa actgcaactt atgatgtttt ctcaagccct acaacatcag     1260
atgagcctga gatatcagat tcctacacag caacaagtga tcgtattctg gattctatcc     1320
```

```
cacctaaaac ttctagaact cttgaacagc caagggcaac actggctcca agtgaaacac    1380
catttgttcc tcaaaaactg gaaatcttta ccagtccaga aatgcagcct acgacacctg    1440
ctccccagca aactacatct atcccttcta cacctaaacg acgcccccgg cccaaaccgc    1500
caagaaccaa acctgaaaga accacaagtg ccggaacaat tacacctaaa atttctaaaa    1560
gccctgaacc tacatggaca acaccggctc ccggtaaaac acaatttatt tctctgaaac    1620
ctaaaatccc tctcagccca gaagtgacac acaccaaacc tgctcccaag cagacaccac    1680
gtgctcctcc taagccaaaa acatcaccac gcccaagaat cccacaaaca caaccagttc    1740
ctaaggtgcc ccagcgtgtt actgcaaaac caaaaacgtc accaagtcca gaagtgtcat    1800
acaccacacc tgctccaaaa gatgtgctcc ttcctcataa accatacccct gaggtctctc    1860 agagcgaacc tgctcctcta gagacacgag gcatccctttt tatacccatg atttccccaa    1920
gtcctagtca agaggaacta cagaccactc tggaagaaac agaccaatcc acccaagaac    1980
ctttcacaac taagattcca cgaacaactg aactagcaaa gacaactcag gcgccacaca    2040
gattttatac tactgtgagg cccagaacat ctgacaagcc acacatcaga cctggggtca    2100
agcaagcacc caggccatca ggtgctgata gaaatgtatc agtggactct acccacccca    2160
ctaaaaagcc agggactcgc cgcccaccct tgccacccag acctacacac ccacgaagaa    2220
aacctttacc accaaataat gtcactggaa agccaggaag tgcaggaatc atttcatcag    2280
gcccaataac tacaccaccc ctgaggtcaa cacccaggcc tactggaact cccttggaga    2340
gaatagagac agatataaag caaccaacag ttcctgcctc tggagaagaa ctggaaaata    2400
taactgactt tagctcaagc ccaacaagag aaactgatcc tcttgggaag ccaagattca    2460
aaggacctca tgtgcgatac atccaaaagc ctgacaacag tccctgctcc attactgact    2520
ctgtcaaacg gttccccaaa gaggaggcca cagagggaa tgccaccagc ccaccacaga    2580
acccacccac caacctcact gtggtcaccg tggaagggtg cccctcattt gtcatcttgg    2640
actgggaaaa gccactaaat gacactgtca ctgaatatga agttatatcc agagaaaatg    2700
ggtcattcag tgggaagaac aagtccattc aaatgacaaa tcagacattt tccacagtag    2760
aaaatctgaa accaaacacg agttatgaat tccaggtgaa acccaaaaac ccgcttggtg    2820
aaggcccggt cagcaacaca gtggcattca gtactgaatc agcggaccca agagtgagtg    2880
agccagtttc tgcaggaaga gatgccatct ggactgaaag accctttaat tcagactctt    2940
actcagagtg taagggcaaa caatatgtca aaaggacatg gtataaaaaa tttgtaggag    3000
tgcagctgtg caactctctc agatacaaga tttacttgag cgactccctc acaggaaaat    3060
tttataacat aggtgatcag aggggccatg gagaagatca ctgccagttt gtggattcat    3120
ttttagatgg acgcactggg cagcaactca cttctgacca gttaccaatc aaagaaggtt    3180
atttcagagc agttcgccag gaacctgtcc aatttggaga aataggtggt cacacccaaa    3240
tcaattatgt tcagtggtat gaatgtggga ctacaattcc tggaaaatgg tagatgctgc    3300
acaaagttac cttctgtttc atcattgcaa acaaaaatca ttgaaaatac tatgccgcat    3360
tcatttaaag ctattttgtt tactatgtat aaaagtctac aatctaatta atagcaatac    3420
tagatgttta ttattagaaa agattgctga gagtatttat caggttttac aaagtcattt    3480
taagaaagca agatactgat gttaacagaa taacattttt ggggaagctg gctccctatt    3540
catggtattt taagagatca tttgtatatt atttatcaca ctgttgtaat gatgttttga    3600 gatacttta taacaaaatt aacatcaaaa aggtatatac ttttttaaaaa aaatttactt    3660 ttattgatgt gtactcttcc tattgatgag ttaattccat aaatctctac ttagtttaac    3720
```

```
ttattggatc aaattatctt cagcatgtat atctggggaa aaaaggtccg aatttttcaca    3780 tttatattta aacttcaatt ttttatattt aaacttcaat tttttagcaa cagctgaata    3840
gctttgcgga ggagtttaat agttacacat tcatgctaat atacatttcc tttaaacatc    3900
cacaaattct taaaaagatt gaatcagtaa atttcatttc agctaaaaat ggagtctaat    3960
atattgtttc aaaagataca ttttttaccca ccataaatgt tacaatatct gaatatgctt    4020
tgtcaaacta tcccttttatg caatcgtctt catattgttt ttatgattct aatcaagctg    4080
tatgtagaga ctgaatgtga agtcaagtct gagcacaaaa agataatgca caatgagatt    4140
gcctaccatt ttataggata tttactatgt atttatacgt taagacctct atgaatgaat    4200
gtatcagaga atgtctttgt aactaactgt ttaattcaat ctgtaataaa aatctaacta    4260
actaactcat ttatttctat taaaaaggta ttgtcccttta ggcggggaat gggaatcctt    4320
gctgcactgt tgcagtcatt ctgaaaggac ctttccctgt acttacctttt caacatgctt    4380 caatcttatc aacgctacat tttgtatttt tcaaacaggt ataaattctg caataaagag    4440
atgtagtttt tttttaaaaa aaaaaaaaaa aaaaaaaaaa aaaaaaaaaa aaaaaaaaaa    4500
aaaaaaaaaa aaaaaaaaaa aaaaaaaaaa aaa                                 4533

<210> SEQ ID NO 23
<211> LENGTH: 1075
<212> TYPE: PRT
<213> ORGANISM: Homo sapiens

<400> SEQUENCE: 23

Met Arg Gly Gly Lys Cys Asn Met Leu Ser Ser Leu Gly Cys Leu Leu
1               5                   10                  15

Leu Cys Gly Ser Ile Thr Leu Ala Leu Gly Asn Ala Gln Lys Leu Pro
            20                  25                  30

Lys Gly Lys Arg Pro Asn Leu Lys Val His Ile Asn Thr Thr Ser Asp
        35                  40                  45

Ser Ile Leu Leu Lys Phe Leu Arg Pro Ser Pro Asn Val Lys Leu Glu
    50                  55                  60

Gly Leu Leu Leu Gly Tyr Gly Ser Asn Val Ser Pro Asn Gln Tyr Phe
65                  70                  75                  80

Pro Leu Pro Ala Glu Gly Lys Phe Thr Glu Ala Ile Val Asp Ala Glu
                85                  90                  95

Pro Lys Tyr Leu Ile Val Val Arg Pro Ala Pro Pro Ser Gln Lys
            100                 105                 110

Lys Ser Cys Ser Gly Lys Thr Arg Ser Arg Lys Pro Leu Gln Leu Val
        115                 120                 125

Val Gly Thr Leu Thr Pro Ser Ser Val Phe Leu Ser Trp Gly Phe Leu
    130                 135                 140

Ile Asn Pro His His Asp Trp Thr Leu Pro Ser His Cys Pro Asn Asp
145                 150                 155                 160

Arg Phe Tyr Thr Ile Arg Tyr Arg Glu Lys Asp Lys Glu Lys Lys Trp
                165                 170                 175

Ile Phe Gln Ile Cys Pro Ala Thr Glu Thr Ile Val Glu Asn Leu Lys
            180                 185                 190

Pro Asn Thr Val Tyr Glu Phe Gly Val Lys Asp Asn Val Glu Gly Gly
        195                 200                 205

Ile Trp Ser Lys Ile Phe Asn His Lys Thr Val Val Gly Ser Lys Lys
    210                 215                 220

Val Asn Gly Lys Ile Gln Ser Thr Tyr Asp Gln Asp His Thr Val Pro
225                 230                 235                 240
```

```
Ala Tyr Val Pro Arg Lys Leu Ile Pro Ile Thr Ile Lys Gln Val
                245                 250                 255

Ile Gln Asn Val Thr His Lys Asp Ser Ala Lys Ser Pro Glu Lys Ala
            260                 265                 270

Pro Leu Gly Gly Val Ile Leu Val His Leu Ile Ile Pro Gly Leu Asn
            275                 280                 285

Glu Thr Thr Val Lys Leu Pro Ala Ser Leu Met Phe Glu Ile Ser Asp
    290                 295                 300

Ala Leu Lys Thr Gln Leu Ala Lys Asn Glu Thr Leu Ala Leu Pro Ala
305                 310                 315                 320

Glu Ser Lys Thr Pro Glu Val Glu Lys Ile Ser Ala Arg Pro Thr Thr
                325                 330                 335

Val Thr Pro Glu Thr Val Pro Arg Ser Thr Lys Pro Thr Thr Ser Ser
            340                 345                 350

Ala Leu Asp Val Ser Glu Thr Thr Leu Ala Ser Ser Glu Lys Pro Trp
        355                 360                 365

Ile Val Pro Thr Ala Lys Ile Ser Glu Asp Ser Lys Val Leu Gln Pro
    370                 375                 380

Gln Thr Ala Thr Tyr Asp Val Phe Ser Ser Pro Thr Thr Ser Asp Glu
385                 390                 395                 400

Pro Glu Ile Ser Asp Ser Tyr Thr Ala Thr Ser Asp Arg Ile Leu Asp
                405                 410                 415

Ser Ile Pro Pro Lys Thr Ser Arg Thr Leu Glu Gln Pro Arg Ala Thr
            420                 425                 430

Leu Ala Pro Ser Glu Thr Pro Phe Val Pro Gln Lys Leu Glu Ile Phe
        435                 440                 445

Thr Ser Pro Glu Met Gln Pro Thr Thr Pro Ala Pro Gln Gln Thr Thr
    450                 455                 460

Ser Ile Pro Ser Thr Pro Lys Arg Arg Pro Arg Pro Lys Pro Pro Arg
465                 470                 475                 480

Thr Lys Pro Glu Arg Thr Thr Ser Ala Gly Thr Ile Thr Pro Lys Ile
                485                 490                 495

Ser Lys Ser Pro Glu Pro Thr Trp Thr Thr Pro Ala Pro Gly Lys Thr
            500                 505                 510

Gln Phe Ile Ser Leu Lys Pro Lys Ile Pro Leu Ser Pro Glu Val Thr
        515                 520                 525

His Thr Lys Pro Ala Pro Lys Gln Thr Pro Arg Ala Pro Pro Lys Pro
    530                 535                 540

Lys Thr Ser Pro Arg Pro Arg Ile Pro Gln Thr Gln Pro Val Pro Lys
545                 550                 555                 560

Val Pro Gln Arg Val Thr Ala Lys Pro Lys Thr Ser Pro Ser Pro Glu
                565                 570                 575

Val Ser Tyr Thr Thr Pro Ala Pro Lys Asp Val Leu Leu Pro His Lys
            580                 585                 590

Pro Tyr Pro Glu Val Ser Gln Ser Glu Pro Ala Pro Leu Gly Thr Arg
        595                 600                 605

Gly Ile Pro Phe Ile Pro Met Ile Ser Pro Ser Gln Glu Glu
    610                 615                 620

Leu Gln Thr Thr Leu Glu Glu Thr Asp Gln Ser Thr Gln Glu Pro Phe
625                 630                 635                 640

Thr Thr Lys Ile Pro Arg Thr Thr Glu Leu Ala Lys Thr Thr Gln Ala
                645                 650                 655

Pro His Arg Phe Tyr Thr Thr Val Arg Pro Arg Thr Ser Asp Lys Pro
```

```
                    660             665                 670
His Ile Arg Pro Gly Val Lys Gln Ala Pro Arg Pro Ser Gly Ala Asp
                675             680              685

Arg Asn Val Ser Val Asp Ser Thr His Pro Thr Lys Lys Pro Gly Thr
        690                 695                 700

Arg Arg Pro Pro Leu Pro Pro Arg Pro Thr His Pro Arg Arg Lys Pro
705                 710                 715                 720

Leu Pro Pro Asn Asn Val Thr Gly Lys Pro Gly Ser Ala Gly Ile Ile
                725                 730                 735

Ser Ser Gly Pro Ile Thr Thr Pro Pro Leu Arg Ser Thr Ser Arg Pro
            740                 745                 750

Thr Gly Thr Pro Leu Glu Arg Ile Glu Thr Asp Ile Lys Gln Pro Thr
                755                 760             765

Val Pro Ala Ser Gly Glu Glu Leu Glu Asn Ile Thr Asp Phe Ser Ser
        770                 775                 780

Ser Pro Thr Arg Glu Thr Asp Pro Leu Gly Lys Pro Arg Phe Lys Gly
785                 790                 795                 800

Pro His Val Arg Tyr Ile Gln Lys Pro Asp Asn Ser Pro Cys Ser Ile
                805             810                 815

Thr Asp Ser Val Lys Arg Phe Pro Lys Glu Glu Ala Thr Glu Gly Asn
                820             825                 830

Ala Thr Ser Pro Pro Gln Asn Pro Thr Asn Leu Thr Val Val Thr
                835                 840             845

Val Glu Gly Cys Pro Ser Phe Val Ile Leu Asp Trp Glu Lys Pro Leu
        850                 855                 860

Asn Asp Thr Val Thr Glu Tyr Glu Val Ile Ser Arg Glu Asn Gly Ser
865                 870                 875                 880

Phe Ser Gly Lys Asn Lys Ser Ile Gln Met Thr Asn Gln Thr Phe Ser
                885                 890                 895

Thr Val Glu Asn Leu Lys Pro Asn Thr Ser Tyr Glu Phe Gln Val Lys
                900                 905                 910

Pro Lys Asn Pro Leu Gly Glu Gly Pro Val Ser Asn Thr Val Ala Phe
            915                 920                 925

Ser Thr Glu Ser Ala Asp Pro Arg Val Ser Glu Pro Val Ser Ala Gly
930                 935                 940

Arg Asp Ala Ile Trp Thr Glu Arg Pro Phe Asn Ser Asp Ser Tyr Ser
945                 950                 955                 960

Glu Cys Lys Gly Lys Gln Tyr Val Lys Arg Thr Trp Tyr Lys Lys Phe
                965                 970                 975

Val Gly Val Gln Leu Cys Asn Ser Leu Arg Tyr Lys Ile Tyr Leu Ser
            980                 985                 990

Asp Ser Leu Thr Gly Lys Phe Tyr Asn Ile Gly Asp Gln Arg Gly His
            995                 1000                1005

Gly Glu Asp His Cys Gln Phe Val Asp Ser Phe Leu Asp Gly Arg
            1010                1015                1020

Thr Gly Gln Gln Leu Thr Ser Asp Gln Leu Pro Ile Lys Glu Gly
            1025                1030                1035

Tyr Phe Arg Ala Val Arg Gln Glu Pro Val Gln Phe Gly Glu Ile
            1040                1045                1050

Gly Gly His Thr Gln Ile Asn Tyr Val Gln Trp Tyr Glu Cys Gly
            1055                1060                1065

Thr Thr Ile Pro Gly Lys Trp
            1070                1075
```

```
<210> SEQ ID NO 24
<211> LENGTH: 859
<212> TYPE: DNA
<213> ORGANISM: Homo sapiens

<400> SEQUENCE: 24
ctccggtgag ttttgtggcg ggaagcttct gcgctggtgc ttagtaaccg actttcctcc      60
ggactcctgc acgacctgct cctacagccg gcgatccact cccggctgtt cccccggagg     120
gtccagaggc ctttcagaag gagaaggcag ctctgtttct ctgcagagga gtagggtcct     180
ttcagccatg aagcatgtgt tgaacctcta cctgttaggt gtggtactga ccctactctc     240
catcttcgtt agagtgatgg agtccctaga gggcttacta gagagcccat cgcctgggac     300
ctcctggacc accagaagcc aactagccaa cacagagccc accaagggcc ttccagacca     360
tccatccaga agcatgtgat aagacctcct tccatactgg ccatattttg gaacactgac     420
ctagacatgt ccagatggga gtcccattcc tagcagacaa gctgagcacc gttgtaacca     480
gagaactatt actaggcctt gaagaacctg tctaactgga tgctcattgc ctgggcaagg     540
cctgtttagg ccggttgcgg tggctcatgc ctgtaatcct agcactttgg gaggctgagg     600
tgggtggatc acctgaggtc aggagttcga gaccagcctc gccaacatgg cgaaacccca     660
tctctactaa aaatacaaaa gttagctggg tgtggtggca gaggcctgta atcccagctc     720
cttgggaggc tgaggcggga gaattgcttg aacccgggga cggaggttgc agtgagccga     780
gatcgcactg ctgtacccag cctgggccac agtgcaagac tccatctcaa aaaaaaaaa     840 aaaaaaaaaa aaaaaaaa                                                  859

<210> SEQ ID NO 25
<211> LENGTH: 63
<212> TYPE: PRT
<213> ORGANISM: Homo sapiens

<400> SEQUENCE: 25

Met Lys His Val Leu Asn Leu Tyr Leu Leu Gly Val Val Leu Thr Leu
1               5                   10                  15

Leu Ser Ile Phe Val Arg Val Met Glu Ser Leu Glu Gly Leu Leu Glu
            20                  25                  30

Ser Pro Ser Pro Gly Thr Ser Trp Thr Thr Arg Ser Gln Leu Ala Asn
        35                  40                  45

Thr Glu Pro Thr Lys Gly Leu Pro Asp His Pro Ser Arg Ser Met
    50                  55                  60
```